(12) United States Patent
Loque et al.

(10) Patent No.: US 10,774,338 B2
(45) Date of Patent: Sep. 15, 2020

(54) GENERATION OF HERITABLE CHIMERIC PLANT TRAITS

(71) Applicant: The Regents of the University of California, Oakland, CA (US)

(72) Inventors: Dominique Loque, Albany, CA (US); Yan Liang, Emeryville, CA (US)

(73) Assignee: The Regents of the University of California, Oakland, CA (US)

( * ) Notice: Subject to any disclaimer, the term of this patent is extended or adjusted under 35 U.S.C. 154(b) by 8 days.

(21) Appl. No.: 14/598,599

(22) Filed: Jan. 16, 2015

(65) Prior Publication Data

US 2015/0218573 A1    Aug. 6, 2015

Related U.S. Application Data

(60) Provisional application No. 61/928,216, filed on Jan. 16, 2014.

(51) Int. Cl.
    *C12N 15/82* (2006.01)

(52) U.S. Cl.
    CPC ..... *C12N 15/8255* (2013.01); *C12N 15/8216* (2013.01); *C12N 15/8246* (2013.01)

(58) Field of Classification Search
    None
    See application file for complete search history.

(56) References Cited

U.S. PATENT DOCUMENTS

| | | | |
|---|---|---|---|
| 6,140,081 A | 10/2000 | Barbas | |
| 6,453,242 B1 | 9/2002 | Eisenberg et al. | |
| 6,534,261 B1 | 3/2003 | Cox, III et al. | |
| 7,799,906 B1 * | 9/2010 | Rottmann | C07K 14/415 435/320.1 |
| 8,932,814 B2 * | 1/2015 | Cong | C12N 15/63 424/94.1 |
| 2003/0232410 A1 | 12/2003 | Liljedahl et al. | |
| 2005/0026157 A1 | 2/2005 | Baltimore et al. | |
| 2005/0064474 A1 | 3/2005 | Urnov et al. | |
| 2005/0208489 A1 | 9/2005 | Carroll et al. | |
| 2006/0188987 A1 | 8/2006 | Guschin et al. | |
| 2008/0182332 A1 | 7/2008 | Cai et al. | |
| 2009/0117617 A1 | 5/2009 | Holmes et al. | |
| 2009/0205083 A1 | 8/2009 | Gupta et al. | |
| 2009/0263900 A1 | 10/2009 | Dekelver et al. | |
| 2010/0047805 A1 | 2/2010 | Wang | |
| 2010/0199389 A1 | 8/2010 | Butler et al. | |
| 2011/0167521 A1 | 7/2011 | Dekelver et al. | |
| 2011/0189775 A1 | 8/2011 | Ainley et al. | |
| 2011/0207221 A1 | 8/2011 | Cost et al. | |
| 2011/0239315 A1 | 9/2011 | Bonas et al. | |
| 2011/0301073 A1 | 12/2011 | Gregory et al. | |

FOREIGN PATENT DOCUMENTS

| | | |
|---|---|---|
| WO | 98/53058 A1 | 11/1998 |
| WO | 98/53059 A1 | 11/1998 |
| WO | 98/53060 A1 | 11/1998 |
| WO | 03/016496 A2 | 2/2003 |
| WO | 2007/014275 A2 | 2/2007 |
| WO | 2010/079430 A1 | 7/2010 |
| WO | 2012/103555 A2 | 8/2012 |

OTHER PUBLICATIONS

Mitsuda et al 2005 The Plant Cell 17:2993-3006.*
Boch et al. "Breaking the code of DNA binding specificity of TAL-type III effectors", *Science*, vol. 326, No. 5959, pp. 1509-1512 (2009).
Caroll, "Genome Engineering With Zinc-Finger Nucleases", *Genetics*, 188(4), 773-782 (2011).
Cermak et al., "Efficient design and assembly of custom TALEN and other TAL effector-based constructs for DNA targeting", *Nucleic Acids Research*, vol. 39, No. 12, e82, 11 pages (2011).
Curtin et al., "Targeted Mutagenesis of Duplicated Genes in Soybean with Zinc-Finger Nucleases", *Plant Physiology*, vol. 156, pp. 466-473 (2011).
De Pater et al., "ZFN-induced mutagenesis and gene-targeting in Arabidopsis through Agrobacterium-mediated floral dip transformation", *Plant Biotechnology Journal*, vol. 7, pp. 821-835 (2009).
Durai et al., "Zinc finger nucleases: custom-designed molecular scissors for genome engineering of plant and mammalian cells", *Nucleic Acids Research*, 33(18), 5978-5990 (2005).
Gaj et al., "ZFN, TALEN, and CRISPR/Cas-based methods for genome engineering", *Trends in Biotechnology*, vol. 31, No. 7, pp. 397-405 (2013).
Heigwer et al., "E-TALEN: a web tool to design TALENs for genome engineering", *Nucleic Acids Research*, 41(20), e190, 2013.
Jiang et al., "Demonstration of CRISPR/Cas9/sgRNA-mediated targeted gene modification in Arabidopsis, tobacco, sorghum and rice", *Nucleic Acids Research*, 41(20), e188 (2013).
Kim et al., "Targeted genome engineering via zinc finger nucleases", *Plant Biotechnol Rep*, vol. 5, pp. 9-17 (2011).
Li et al., "High-efficiency TALEN-based gene editing produces disease-resistant rice", *Nat Biotechnol*, vol. 30, No. 5, pp. 390-392 (2012).
Moscou et a., "A Simple Cipher Governs DNA Recognition by TAL Effectors", *Science*, vol. 326, pp. 1501 ( 2009).
Nekrasov et al., "Targeted mutagenesis in the model plant Nicotiana benthamiana using Cas9 RNA-guided endonuclease", *Nature Biotechnology*, vol. 31, No. 8, pp. 691-693 (2013)
Urnov et al., "Highly efficient endogenous human gene correction using designed zinc-finger nucleases", *Nature*, vol. 435, No. 7042, pp. 646-651 (2005).

(Continued)

*Primary Examiner* — Brent T Page

(74) *Attorney, Agent, or Firm* — Kilpatrick Townsend & Stockton LLP

(57) ABSTRACT

The present invention provides methods and compositions for targeting enzymes involved in lignin or xylan biosynthesis using genome editing nucleases to specifically reduce content in a desired plant cell type(s).

8 Claims, 3 Drawing Sheets

Specification includes a Sequence Listing.

(56) References Cited

OTHER PUBLICATIONS

Urnov et al., "Genome editing with engineered zinc finger nucleases", *Nature Reviews Genetics*, 11(9), 636-646 (2010).
Wang et al., "Hairpin RNAs derived from RNA polymerase II and polymerase III promoter-directed transgenes are processed differently in plants", *RNA*, vol. 14, pp. 903-913 (2008).
Wendt et al., "TAL effector uncleases induce mutations ata pre-selected location in the genome of primary barley transformants", *Plant Mol Biol*, vol. 83, pp. 279-285 (2013).
Xie et al., "RNA-guided Genome Editing in Plants Using a CRISPR-Cas System", *Molecular Plant Advance Access*, pp. 1-29 (2013).
Zeevi et al., "Zinc Finger Nuclease and homing Endonuclease-Mediated Assembly of Multigene Plant Transformation Vectors", *Plant Physiology*, vol. 158, pp. 132-144 (2012).

\* cited by examiner

GENERATION OF HERITABLE CHIMERIC PLANT TRAITS

CROSS-REFERENCE TO RELATED APPLICATIONS

This applications claims priority benefit of U.S. provisional application No. 61/928,216, filed Jan. 16, 2014, which application is herein incorporated by reference.

STATEMENT AS TO RIGHTS TO INVENTIONS MADE UNDER FEDERALLY SPONSORED RESEARCH AND DEVELOPMENT

This invention was made with government support under Contract No. DE-AC02-05CH11231 awarded by the U.S. Department of Energy. The government has certain rights in this invention.

REFERENCE TO A "SEQUENCE LISTING" SUBMITTED AS AN ASCII TEXT FILE

This application includes a Sequence Listing as a text file named "Sequence Listing 77429-012010US-930131" created on Apr. 15, 2015 and containing 57,156 bytes. The material contained in this text file is hereby incorporated by reference in its entirety for all purposes.

BACKGROUND OF THE INVENTION

Lignin, a major component of cell walls, is the third most-abundant biopolymer and the largest available resource of natural aromatic polymers. It is mainly composed of the monolignols p-coumaryl, coniferyl, and sinapyl alcohols which give rise to the p-hydroxyphenyl (H), guaiacyl (G) and syringyl (S) lignin units (e.g., Bocrjan et al, *Annual Review of Plant Biology* 54:519-546, 2003). Unfortunately, it is also the primary contributor to the high cost of lignocellulosic sugar production, because cell wall polysaccharides are encrusted with lignin, which make them highly resistant to extraction and enzymatic hydrolysis. Moreover, lignin has almost no commercial value aside from its role as a source of heat, and it is generally treated as a waste product.

Lignin has been a target of genetic manipulation for several decades because its content in biomass is inversely correlated with its forage digestibility and kappa value in the pulping industry. Lignin biosynthesis is well-characterized and all the enzymes required for the synthesis of its three major building blocks—called monolignols—are well-known and highly-conserved in all vascular plants. However, lignin cannot be readily removed from growing plants without causing deleterious developmental effects (e.g., Bonawitz & Chapple, *Curr Opin Biotechnol* 24:336-343, 2013). Genetic manipulation trials using natural mutants or silencing strategies have failed because they drastically reduced lignin content in a non-selective way. Although there are cases in which mild genetic manipulations have been used to moderately reduce lignin content or modify its composition in biomass, modestly improving saccharification efficiency, forage digestibility, and pulping yield (e.g., Li et al., *Plant Journal* 54:569-581, 2008), these approaches are still rather limited.

Classical lignin-modification methods typically repress the expression or activity of lignin biosynthetic genes. They require identification of natural defective alleles, the screening of single-nucleotide polymorphisms (SNPs) from mutant populations (usually a labor-intensive process) or the development of RNAi-based gene-silencing approaches. A limitation to these approaches is the lack of tissue specificity because every cell carries the same defective allele or silenced gene because RNAi moves from cell-to-cell and affect most of the tissues in the plant (Brosnan & Voinnet, *Curr Opin Plant Biol* 14:580-587, 2011). Moreover, they affect not only the lignin biosynthesis pathway, but also have indirect effects on other metabolic routes connected to the phenylpropanoid and monolignol pathways. The phenylpropanoid pathway, for example, generates a wide array of secondary metabolites that contribute to all aspects of plant development and plant responses to biotic and abiotic stresses (e.g., Vogt, *Molecular Plant* 3:2-20, 2010).

There is a need for new methods to reduce lignin content further, without altering plant development or causing undesirable effects. This invention addresses that need.

BRIEF SUMMARY OF THE INVENTION

In one aspect, the present invention provides methods of engineering a plant to have reduced lignin, xylan, or acetate content comprising introducing into the plant a genome editing construct comprising a polynucleotide that encodes a TALEN, ZNF, or nuclear-targeted Cas9 nuclease that is operably linked to a fiber-specific promoter wherein the genome editing construct is targeted to cleave one or more lignin or xylan biosynthesis genes. In further aspects, the invention also provides genome editing compositions, plants having reduced lignin, xylan, or acetate content generated in accordance with the invention, and methods of using such plants.

Thus, in one aspect, the invention provides a method of engineering a plant having reduced lignin and/or xylan content, the method comprising:

introducing into the plant a nucleic acid construct that encodes a first and a second gene editing nuclease that together dimerize and cleave a target site in a gene that encodes a lignin or xylan biosynthesis gene, wherein the polynucleotide encoding the first nuclease is operably linked to a first fiber-specific promoter; and wherein the gene editing nuclease comprises a ZFN DNA binding domain or a TALE DNA binding domain that specifically binds to a sequence at the target site fused to a nuclease domain; and the polynucleotide encoding the second nuclease comprises a ZFN DNA binding domain or TALE DNA binding domain that specifically binds to a sequence at the target sited fused to a nuclease domain that dimerizes to the nuclease domain in the first gene editing nuclease that is operably linked to a second fiber-specific promoter different from the first;

culturing the plant under conditions in which the first and the second gene editing nucleases are expressed and cleave the gene at the target site; and selecting a plant that has reduced expression of the lignin or xylan biosynthesis gene. In some embodiments, the nuclease domain in the first gene editing nuclease and the nuclease domain in the second gene editing domain are each FokI nuclease domains. In some embodiments, the first and second fiber-specific promoters are each a different NST promoter selected from NST1, NST2, or NST3. In some embodiments, the first fiber-specific promoter is an NST1 promoter and the second fiber-specific promoter is an NST3 promoter. In some embodiments, the lignin biosynthesis gene is a C4H gene, a C3H gene, an HCT gene, a CCR gene, or a Myb63 gene; or the xylan biosynthesis gene is an IRX7 gene or an IRX8 gene.

In a further aspect, the invention provides a method of engineering a plant having reduced lignin and/or xylan content, the method comprising:

introducing into a plant nucleic acid construct encoding a gene editing nuclease, wherein the construct comprises a polynucleotide encoding a Cas9 domain operably linked to a fiber-specific promoter, and a sequence encoding at least a first chimeric RNA comprising a targeting region that selectively hybridizes to a target site in a lignin or xylan biosynthesis gene linked to a Cas9 handle;

culturing the plant under conditions in which the nucleic acid construct is expressed and the Cas9 domain cleaves the gene at the target site; and selecting a plant that has reduced expression of the lignin or xylan biosynthesis gene. In some embodiments, the fiber-specific promoter is an NST1 promoter. In some embodiments, the lignin or xylan biosynthesis gene is a C4H gene, a C3H gene, an HCT gene, a CCR gene, a Myb63 gene, an IRX7 gene or an IRX8 gene. In some embodiments, the targeting region comprises a sequence selected from the group consisting of SEQ ID NOs. 1 to 21. In some embodiments, the nucleic acid construct comprises a polynucleotide where the nuclear-targeted Cas9 protein is encoded by the corresponding region of SEQ ID NO:31. In some embodiments, the nucleic acid construct comprises a polynucleotide having a sequence of SEQ ID NO:31. In some embodiments, the nucleic acid construct further comprises a sequence encoding a second chimeric RNA that comprises a targeting region that selectively hybridizes to a site in the lignin or xylan biosynthesis gene different from the site targeted by the first chimeric RNA. In some embodiments, the sequence encoding the targeting region in the first chimeric RNA and the sequence encoding the targeting region in the second chimeric RNA are each selected from the group consisting of SEQ ID NOs. 1 to 21. In some embodiments, the nucleic acid construct comprises a polynucleotide having a sequence of SEQ ID NO:32. In some embodiments, the nucleic acid construct further comprises a sequence encoding a second chimeric RNA that comprises a targeting region that selectively hybridizes to a site in a second lignin or xylan biosynthesis gene where the second lignin or xylan biosynthesis gene is different from the first lignin or xylan biosynthesis gene targeted by the first chimeric RNA. In some embodiments the nucleic acid construct comprises a sequence that encodes a first chimeric RNA that targets a lignin biosynthesis gene and a sequence that encodes a second chimeric RNA that targets a xylan biosynthesis gene. In some embodiments, the first gene and the second gene is selected from a C4H gene, a C3H gene, an HCT gene, a CCR gene, a Myb63 gene, an IRX7 gene or an IRX8 gene. In some embodiments, the sequence encoding the targeting region in the first chimeric RNA and the sequence encoding targeting region in the second chimeric RNA are each selected from the group consisting of SEQ ID NOs. 1 to 21. In some embodiments, the nucleic acid construct comprises a polynucleotide having a sequence of SEQ ID NO:33.

In a further aspect, the invention provides a plant having reduced lignin and/or xylan content, or reduced acetate content, engineered by the methods described herein, and a cell form the plant or part of a plant. In some embodiments, the invention provides a seed, flower, leaf, or fruit from the plant. In some embodiments, the invention provides biomass comprising a plant or part of a plant, engineered as described herein to have reduced lignin and/or xylan content or reduced acetate content.

In some embodiments, the invention provides a plant cell comprising a nucleic acid construct that encodes a first and a second gene editing nuclease that together dimerize and cleave a target site in a gene that encodes a lignin or xylan biosynthesis gene, wherein the polynucleotide encoding the first nuclease is operably linked to a first fiber-specific promoter; and wherein the gene editing nuclease comprises a ZFN DNA binding domain or a TALE DNA binding domain that specifically binds to a sequence at the target site fused to a nuclease domain; and the polynucleotide encoding the second nuclease comprises a ZFN DNA binding domain or TALE DNA binding domain that specifically binds to a sequence at the target sited fused to a nuclease domain that dimerizes to the nuclease domain in the first gene editing nuclease that is operably linked to a second fiber-specific promoter different from the first. In some embodiments, the first gene editing nuclease and the nuclease domain in the second gene editing domain are each FokI nuclease domains. In some embodiments, the first and second fiber-specific promoters are each a different NST promoter selected from NST1, NST2, or NST3. In some embodiments, the first fiber-specific promoter is an NST1 promoter and the second fiber-specific promoter is an NST3 promoter. In some embodiments, the lignin biosynthesis gene is a C4H gene, a C3H gene, an HCT gene, a CCR gene, or a Myb63 gene; or the xylan biosynthesis gene is an IRX7 gene or an IRX8 gene.

In a further aspect, the invention provides a plant cell comprising a nucleic acid construct encoding a gene editing nuclease, wherein the construct comprises a polynucleotide encoding a Cas9 domain operably linked to a fiber-specific promoter, and a sequence encoding at least a first chimeric RNA comprising a targeting region that selectively hybridizes to a target site in a lignin or xylan biosynthesis gene linked to a Cas9 handle. In some embodiments, the fiber-specific promoter is an NST1 promoter. In some embodiments, the lignin or xylan biosynthesis gene is a C4H gene, a C3H gene, an HCT gene, a CCR gene, a Myb63 gene, an IRX7 gene or an IRX8 gene. In some embodiments, the sequence encoding the targeting region comprises a sequence selected from the group consisting of SEQ ID NOs. 1 to 21. In some embodiments, the nucleic acid construct comprises a polynucleotide having a sequence of SEQ ID NO:31. In some embodiments, the nucleic acid construct further comprises a sequence encoding a second chimeric RNA that comprises a targeting region that selectively hybridizes to a site in the lignin or xylan biosynthesis gene different from the site targeted by the first chimeric RNA. In some embodiments, the sequence encoding the targeting region in the first chimeric RNA and the sequence encoding the targeting region in the second chimeric RNA are each selected from the group consisting of SEQ ID NOs. 1 to 21. In some embodiments, the nucleic acid construct comprises a polynucleotide having a sequence of SEQ ID NO:32. In some embodiments, the nucleic acid construct further comprises a sequence encoding a second chimeric RNA that comprises a targeting region that selectively hybridizes to a site in a second lignin or xylan biosynthesis gene where the second lignin or xylan biosynthesis gene is different from the first lignin or xylan biosynthesis gene targeted by the first chimeric RNA. In some embodiments the nucleic acid construct comprises a sequence that encodes a first chimeric RNA that targets a lignin biosynthesis gene and a sequence that encodes a second chimeric RNA that targets a xylan biosynthesis gene. In some embodiments, the first gene and the second gene is selected from a C4H gene, a C3H gene, an HCT gene, a CCR gene, a Myb63 gene, an IRX7 gene or an IRX8 gene. In some embodiments, the sequence encoding the targeting region in the first chimeric RNA and the sequence encoding targeting region in the second chimeric RNA are each selected from the group consisting of SEQ ID NOs. 1 to 21. In some embodiments, the nucleic acid construct comprises a polynucleotide having a sequence of SEQ ID NO:33.

In a further aspect, the invention provides a plant, or part of a plant, comprising a plant cell comprising a genome editing nucleic acid construct as described herein; or biomass comprising a such a plant or part of the plant. In typical embodiments, the plant has reduced lignin or xylan content that is substantially localized to the fiber cells of the plant. In some embodiments, the plant has increased digestibility for ruminants as compared to a wild-type plant. In some embodiments, the plant has reduced xylan (C5-sugar) content.

In a further aspect, the invention provides a method of obtaining an increased amount of soluble sugars from a plant in a saccharification reaction, the method comprising subjecting a plant engineered to have fiber-specific reduction in the activity of a lignin or xylan biosynthesis gene as described herein to a saccharification reaction, thereby increasing the amount of soluble sugars that can be obtained from the plant as compared to a wild-type plant.

In some embodiments, the plant (or plant part, or seed, flower, leaf, or fruit from the plant) is selected from the group consisting of Arabidopsis, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, and Brachypodium.

In still another aspect, the present invention provides biomass comprising plant tissue from a plant or part of a plant as described herein.

In another aspect, the present invention provides methods of obtaining an increased C6/C5 ratio (e.g., glucose/xylose) in a plant secondary cell walls resulting in an increase C6/C5 ratio in a saccharification reaction. In some embodiments, the method comprises subjecting a plant that is engineered to have reduced xylan content as described herein to a saccharification reaction, thereby increasing the amount of soluble sugars or C6/C5 ratio that can be obtained from the plant as compared to a wild-type plant.

In still another aspect, the present invention provides methods of increasing the digestibility of the biomass for ruminants. In some embodiments, the method comprises introducing an expression cassette as described herein into a plant; culturing the plant under conditions in which the protein that diverts the monolignol precursor from the lignin biosynthesis pathway is expressed; and obtaining biomass from the plant, thereby increasing the digestibility of the biomass for ruminants.

DETAILED DESCRIPTION OF THE INVENTION

I. Definitions

Figure 1:
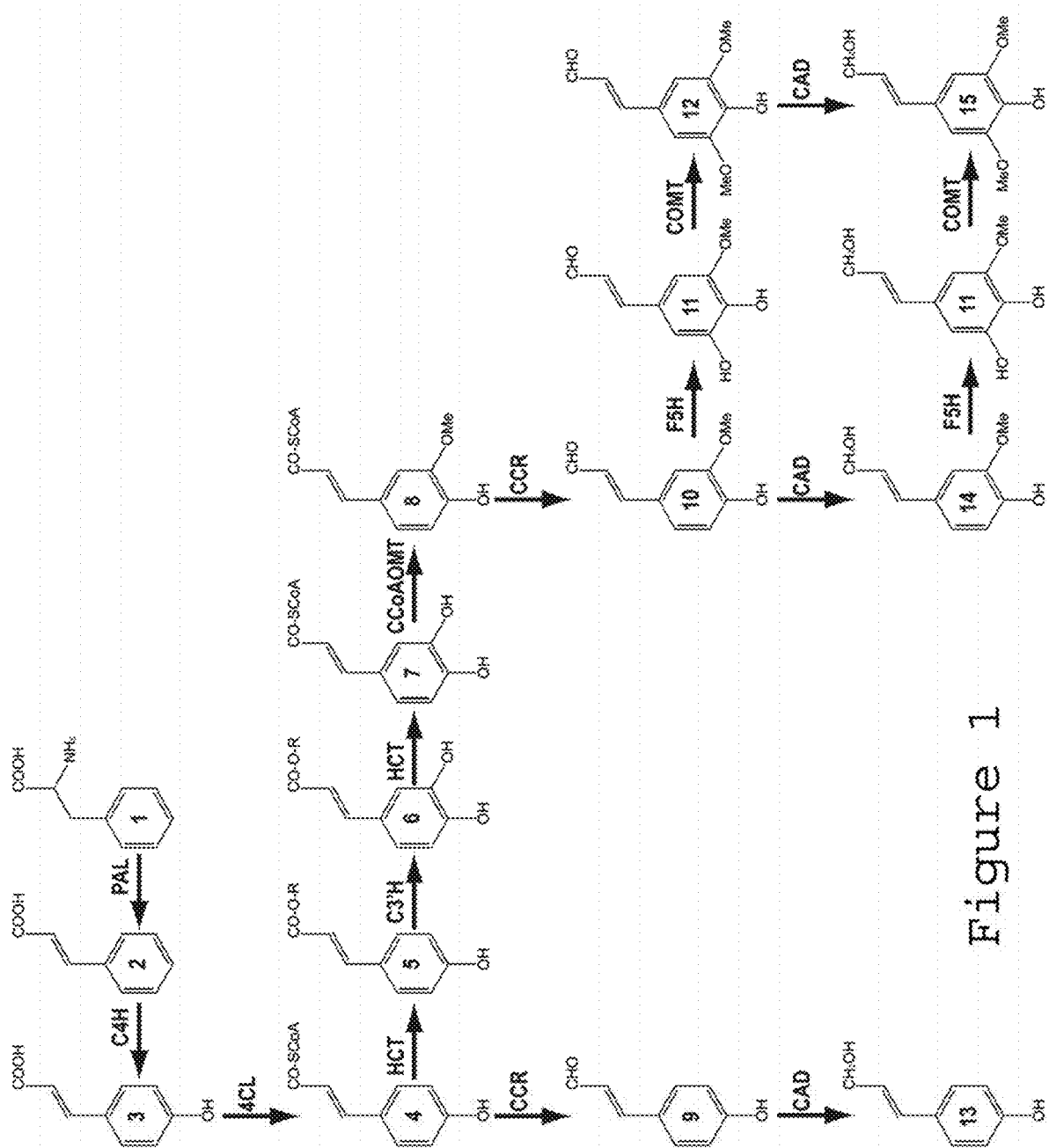
FIG. 1. Representation of the lignin biosynthesis pathway. Modified lignin biosynthesis pathway from Fraser and Chapple (2011). Enzyme descriptions: PAL: phenylalanine ammonia-lyase; C4H: cinnamate-4-hydroxylase; 4CL: 4-hydroxycinnamate CoA-ligase; HCT: hydroxycinnamoyl-CoA shikimate/quinate hydroxycinnamoyltransferase; C3'H: 4-hydroxycinnamate 3-hydroxylase; CCoAOMT: caffeoyl-CoA O-methyltransferase; CCR: hydroxycinnamoyl-CoA NADPH oxidoreductase; COMT: caffeate O-methyltransferase; CAD: hydroxycinnamyl alcohol dehydrogenase; FSH: ferulate 5-hydroxylase.

As used herein, the term "lignin biosynthesis pathway" refers to an enzymatic pathway (the phenylpropanoid pathway) in plants in which the lignin monomers (p-coumaryl (4-hydroxycinnamyl) alcohol, coniferyl (3-methoxy 4-hydroxycinnamyl) alcohol, and sinapyl (3,5-dimethoxy 4-hydroxycinnamyl) alcohol) are synthesized from phenylalanine.

A "lignin biosynthesis gene" as used herein refers to a gene involved in lignin production. Such genes include both enzymes and regulatory proteins such as the lignin master regulatory protein Myb63. The term encompasses polymorphic variants, alleles, mutants, and interspecies homologs to the specific illustrative gene accession numbers provided herein.

As used herein, the term "xylan biosynthesis enzyme" refers an enzyme that is involved in xylan synthesis. The term as used herein can also relate to an enzyme that modifies xylan, e.g., enzymes that acetylate xylan. The term encompasses polymorphic variants, alleles, mutants, and interspecies homologs to the specific illustrative gene accession numbers provided herein.

The term "sequence-specific endonuclease" or "sequence-specific nuclease," as used herein, refers to a protein that recognizes and binds to a polynucleotide, e.g., a target gene, at a specific nucleotide sequence and catalyzes a single- or double-strand break in the polynucleotide.

The term "RNA-guided DNA nuclease" or "RNA-guided endonuclease," as used herein, refers to a protein that is linked to a guide RNA sequence that binds to a specific nucleotide sequence and catalyzes a single- or double-strand break in the polynucleotide.

A "zinc finger nuclease", as used herein, is a polypeptide that contains a domain that binds to DNA in a sequence specific manner through one or more zinc fingers fused to an endonuclease domain, e.g., Fok1 endonuclease domain.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Patent Publication No. 20110301073, incorporated by reference. A "TALEN" comprises a TALE DNA binding domain fused to an endonuclease domain, e.g., a Fok1 endonuclease domain.

A "genome editing construct" or "genome editing nuclease construct" as used herein refers to a construct encoding both the DNA binding and recognition domain as well as the targeting sequence, i.e., for ZFN and TALEN constructs, the targeting sequence is contained within the DNA binding domain; for Cas9 constructs, the targeting sequence is an RNA targeting site.

The terms "polynucleotide" and "nucleic acid" are used interchangeably and refer to a single or double-stranded polymer of deoxyribonucleotide or ribonucleotide bases read from the 5' to the 3' end. A nucleic acid of the present invention will generally contain phosphodiester bonds, although in some cases, nucleic acid analogs may be used that may have alternate backbones, comprising, e.g., phosphoramidate, phosphorothioate, phosphorodithioate, or O-methylphophoroamidite linkages (see Eckstein, Oligonucleotides and Analogues: A Practical Approach, Oxford University Press); positive backbones; non-ionic backbones, and non-ribose backbones. Thus, nucleic acids or polynucleotides may also include modified nucleotides that permit correct read-through by a polymerase. "Polynucleotide sequence" or "nucleic acid sequence" includes both the sense and antisense strands of a nucleic acid as either individual single strands or in a duplex. As will be appreciated by those in the art, the depiction of a single strand also defines the sequence of the complementary strand; thus the sequences described herein also provide the complement of the sequence. Unless otherwise indicated, a particular nucleic acid sequence also implicitly encompasses variants thereof (e.g., degenerate codon substitutions) and complementary sequences, as well as the sequence explicitly indicated. The nucleic acid may be DNA, both genomic and cDNA, RNA or a hybrid, where the nucleic acid may contain combinations of deoxyribo- and ribo-nucleotides, and combinations of bases, including uracil, adenine, thymine, cytosine, guanine, inosine, xanthine hypoxanthine, isocytosine, isoguanine, etc.

The term "substantially identical," used in the context of two nucleic acids or polypeptides, refers to a sequence that has at least 50% sequence identity with a reference sequence. Percent identity can be any integer from 50% to 100%. Some embodiments include at least: 50%, 55%, 60%, 65%, 70%, 75%, 80%, 85%, 90%, 91%, 92%, 93%, 94%, 95%, 96%, 97%, 98%, or 99%, compared to a reference sequence using the programs described herein; preferably BLAST using standard parameters, as described below. For example, a first polynucleotide is substantially identical to a second polynucleotide sequence if the first polynucleotide sequence is at least 50%, 55%, 60%, 65%, 70%, 75%, 80%, 85%, 90%, 91%, 92%, 93%, 94%, 95%, 96%, 97%, 98%, or 99% identical to the second polynucleotide sequence.

Two nucleic acid sequences or polypeptide sequences are said to be "identical" if the sequence of nucleotides or amino acid residues, respectively, in the two sequences is the same when aligned for maximum correspondence as described below. The terms "identical" or percent "identity," in the context of two or more nucleic acids or polypeptide sequences, refer to two or more sequences or subsequences that are the same or have a specified percentage of amino acid residues or nucleotides that are the same, when compared and aligned for maximum correspondence over a comparison window, as measured using one of the following sequence comparison algorithms or by manual alignment and visual inspection. When percentage of sequence identity is used in reference to proteins or peptides, it is recognized that residue positions that are not identical often differ by conservative amino acid substitutions, where amino acids residues are substituted for other amino acid residues with similar chemical properties (e.g., charge or hydrophobicity) and therefore do not change the functional properties of the molecule. Where sequences differ in conservative substitutions, the percent sequence identity may be adjusted upwards to correct for the conservative nature of the substitution. Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated according to, e.g., the algorithm of Meyers & Miller, *Computer Applic. Biol. Sci.* 4:11-17 (1988) e.g., as implemented in the program PC/GENE (Intelligenetics, Mountain View, Calif., USA).

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window," as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection.

Algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (NCBI) web site. The algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits acts as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word size (W) of 28, an expectation (E) of 10, M=1, N=−2, and a comparison of both strands. For amino acid sequences, the BLASTP program uses as defaults a word size (W) of 3, an expectation (E) of 10, and the BLOSUM62 scoring matrix (see Henikoff & Henikoff, *Proc. Natl. Acad. Sci. USA* 89:10915 (1989)).

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.01, more preferably less than about $10^{-5}$, and most preferably less than about $10^{-20}$.

Nucleic acid or protein sequences that are substantially identical to a reference sequence include "conservatively modified variants." With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine) can be modified to yield a functionally identical molecule. Accordingly, each silent variation of a nucleic acid which encodes a polypeptide is implicit in each described sequence.

As to amino acid sequences, one of skill will recognize that individual substitutions, in a nucleic acid, peptide, polypeptide, or protein sequence which alters a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another:
1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).
(see, e.g., Creighton, *Proteins* (1984)).

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. For example, stringent conditions for hybridization, such as RNA-DNA hybridizations in a blotting technique are those which include at least one wash in 0.2×SSC at 55° C. for 20 minutes, or equivalent conditions.

As used herein, the term "promoter" refers to a polynucleotide sequence capable of driving transcription of a DNA sequence in a cell. Thus, promoters used in the polynucleotide constructs of the invention include transcriptional control elements and regulatory sequences that are involved in regulating or modulating the timing and/or rate of transcription of a gene. For example, a promoter can be a cis-acting transcriptional control element, optionally including an enhancer, involved in transcriptional regulation. These cis-acting sequences typically interact with proteins or other biomolecules to carry out (turn on/off, regulate, modulate, etc.) gene transcription. Promoters are located 5' to the transcribed gene, and as used herein, typically include the sequence 5' from the translation start codon (i.e., including the 5' untranslated region of the mRNA, typically comprising 100-200 bp). Most often the core promoter sequences lie within 1-5 kb of the translation start site, more often within 1 kbp and often within 500 bp of the translation start site. By convention, the promoter sequence is usually provided as the sequence on the coding strand of the gene it controls.

A "cell type-specific promoter" initiates transcription only in one or a few particular cell types or groups of cells forming a tissue. In some embodiments, the promoter is fiber cell-specific. A "fiber cell-specific promoter" refers to a promoter that initiates substantially higher levels of transcription in fiber cells as compared to other non-fiber cells of the plant. In some embodiments, a promoter is fiber cell-specific if the transcription levels initiated by the promoter in fiber cells are at least 3-fold, 4-fold, 5-fold, 6-fold, 7-fold, 8-fold, 9-fold, 10-fold, 50-fold, 100-fold, 500-fold, 1000-fold higher or more as compared to the transcription levels initiated by the promoter in other tissues, resulting in the encoded protein substantially localized in plant cells that possess fiber cells e.g., the stem of a plant. Non-limiting examples of fiber cell specific promoters include the promoters directing expression of the genes NST1, NST2, NST3 and Lac17. See, e.g., Mitsuda et al., *Plant Cell* 17:2993-3006 (2005); Mitsuda et al., *Plant Cell* 19:270-280 (2007); Zhong et al., *Plant Cell* 18:3158-3170, 2006; Berthet et al., The *Plant Cell* 23:1124-37, 2011. A promoter originated from one plant species may be used to direct gene expression in another plant species.

A polynucleotide is "heterologous" to an organism or a second polynucleotide sequence if it originates from a foreign species, or, if from the same species, is modified from its original form. For example, when a polynucleotide encoding a polypeptide sequence is said to be operably linked to a heterologous promoter, it means that the polynucleotide coding sequence encoding the polypeptide is derived from one species whereas the promoter sequence is derived from another, different species; or, if both are derived from the same species, the coding sequence is not naturally associated with the promoter (e.g., is a genetically engineered coding sequence, e.g., from a different gene in the same species, or an allele from a different ecotype or variety, or a gene that is not naturally expressed in the target tissue).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a DNA or RNA sequence if it stimulates or modulates the transcription of the DNA or RNA sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

The term "expression cassette" refers to a nucleic acid construct that, when introduced into a host cell, results in transcription and/or translation of an RNA or polypeptide, respectively. Constructs that are not or cannot be translated are expressly included by this definition The term "plant," as used herein, refers to whole plants and includes plants of a variety of a ploidy levels, including aneuploid, polyploid, diploid, and haploid. The term "plant part," as used herein, refers to shoot vegetative organs and/or structures (e.g., leaves, stems and tubers), branches, roots, flowers and floral organs (e.g., bracts, sepals, petals, stamens, carpels, anthers), ovules (including egg and central cells), seed (including zygote, embryo, endosperm, and seed coat), fruit (e.g., the mature ovary), seedlings, and plant tissue (e.g., vascular tissue, ground tissue, and the like), as well as individual plant cells, groups of plant cells (e.g., cultured plant cells), protoplasts, plant extracts, and seeds. The class of plants that can be used in the methods of the invention is generally as broad as the class of higher and lower plants amenable to transformation techniques, including angiosperms (monocotyledonous and dicotyledonous plants), gymnosperms, ferns, and multicellular algae.

The term "biomass," as used herein, refers to plant material that is processed to provide a product, e.g., a biofuel such as ethanol, or livestock feed, or a cellulose for paper and pulp industry products. Such plant material can include whole plants, or parts of plants, e.g., stems, leaves, branches, shoots, roots, tubers, and the like.

The term "reduced lignin content" encompasses reduced amount of lignin polymer, reduced amount of either or both of the guaiacyl (G) and/or syringyl (S) lignin units, reduced size of a lignin polymer, e.g., a shorter lignin polymer chain due to a smaller number of monolignols being incorporated into the polymer, a reduced degree of branching of the lignin polymer, or a reduced space filling (also called a reduced pervaded volume). In some embodiments, a reduced lignin polymer can be shown by detecting a decrease in the molecular weight of the polymer or a decrease in the number of monolignols by at least 2%, 5%, 10%, 20%, 25%, 30%, 40%, 50%, or more, when compared to the average lignin molecule in a control plant (e.g., a non-transgenic plant). In some embodiments, reduced lignin content can be shown by detecting a decrease in the number or amount of guaiacyl (G) and/or syringyl (S) lignin units in the plant as compared to a control plant (e.g., a non-transgenic plant). In some embodiments, a plant as described herein has reduced lignin content if the amount of guaiacyl (G) and/or syringyl (S) lignin units in the plant is decreased by at least about 2%, 5%, 10%, 20%, 25%, 30%, 40%, 50% or more, as compared to a control plant. Methods for detecting reduced lignin content are described in detail below.

The terms "reduced level of activity," "reduced activity" and "decreased activity" refer interchangeably to a reduction in the amount of activity of a protein, e.g., a lignin biosynthesis protein of interest or a xylan biosynthesis protein of interest in fiber cells of an engineered plant as described herein as compared to the amount of activity in fiber cells in the plant that is not so-engineered. In some embodiments, reduced activity results from reduced expression levels. A reduced level of activity or a reduced level of expression can be a reduction in the amount of activity or expression of a protein, e.g., a lignin or xylan biosynthesis protein, of at least 10%, 20%, 30%, 40%, 50%, 60%, 70%, 80%, or 90% or greater. In some embodiments, the biosynthetic protein is not reduced in amount but is modified in amino acid sequence so that the activity is reduced. Reduction in the amount of expression of a gene or protein can be assessed by measuring decreases in the level of RNA encoded by the gene of interest and/or decreases in the level of protein expression or activity for the protein of interest.

II. Introduction

This invention relates, in part, to generating in vivo small DNA damages in specific cell types in plants at specific locus/loci in order to generate mutations (e.g. single-nucleotide polymorphisms, small deletions) in target gene(s) in the lignin biosynthesis pathway to reduce lignin content in target cell types and/or in the xylan biosynthsesis pathway to reduce xylan (C5 sugar) content in target cell types. In the present invention, this approach is employed to inactivate key lignin genes and genes controlling xylan biosynthesis in target fiber cells. The present invention employs fiber or secondary wall-specific promoter(s) to control the expression of a nuclease designed to target a specific locus/loci. The specificity for the target is achieved by using a Zinc finger nuclease, TALENs, or Cas/CRISPR system.

In the current invention, gene-specific nuclease constructs are employed to disrupt function of a gene in fiber cells that encode a gene in the lignin or xylan biosynthesis pathway. As noted above, such nucleases include zinc-finger nucleases (ZFNs), transcription activator-like effector nucleases (TALENs), and the clustered, regularly interspaced, short palindromic repeats (CRISPR)/CRISPR-associated (CAS) system (see, e.g., Gaj et al., *Trends Biotechnol* 31:397-405, 2013). These nucleases are engineered to be targeted to the gene of interest by employing DNA binding elements specific for the target gene. Directed by the DNA binding elements, endonucleases cleave at the target loci and generate DNA double-strand breaks (DSBs). DSBs are subsequently repaired by one of the two cellular DNA repair mechanisms: non-homologous end joining (NHEJ), or homologous recombination (HR). Repair by NHEJ frequently introduces mutations, resulting in gene interruption at the target loci.

The nuclease employed in accordance with the invention can be a dimerizing pair of zinc-finger nucleases (ZFNs) fusion protein comprising a zinc finger binding domain, which is engineered to bind a sequence within the region of interest, and a cleavage domain. In other embodiments, nuclease is created by one or more TALE DNA-binding domains fused to a nuclease domain (TALEN). In a further embodiment, cleavage is performed using a nuclease system such as CRISPR/Cas with an engineered crRNA/tracr RNA.

DNA-binding elements in ZFNs and TALENs are composed of modular protein motifs (e.g., Boch et al., *Science* 326:1509-1512, 2009; Moore et al., *Proceedings of the National Academy of Sciences* 98:1437-1441, 2001; Moscou, et al., *Science* 326:1501, 2009) An individual ZF primarily recognizes DNA sites of 3 bp. To establish recognition specificity, arrays of ZF units connected by linker sequences recognize DNA sequences 9-18 bp in length (e.g., Moore et al., supra). The DNA-binding motifs in TALEs present as near-perfect repeats, typically 34 amino acids in length. Repeat-variable di-residues (RVDs), usually occurring at residues 12 and 13, designate the base pair or nucleotide recognition code in a one-to-one manner (e.g., Boch et al., Moore et al., Mouscou et al., supra].

Figure 2:
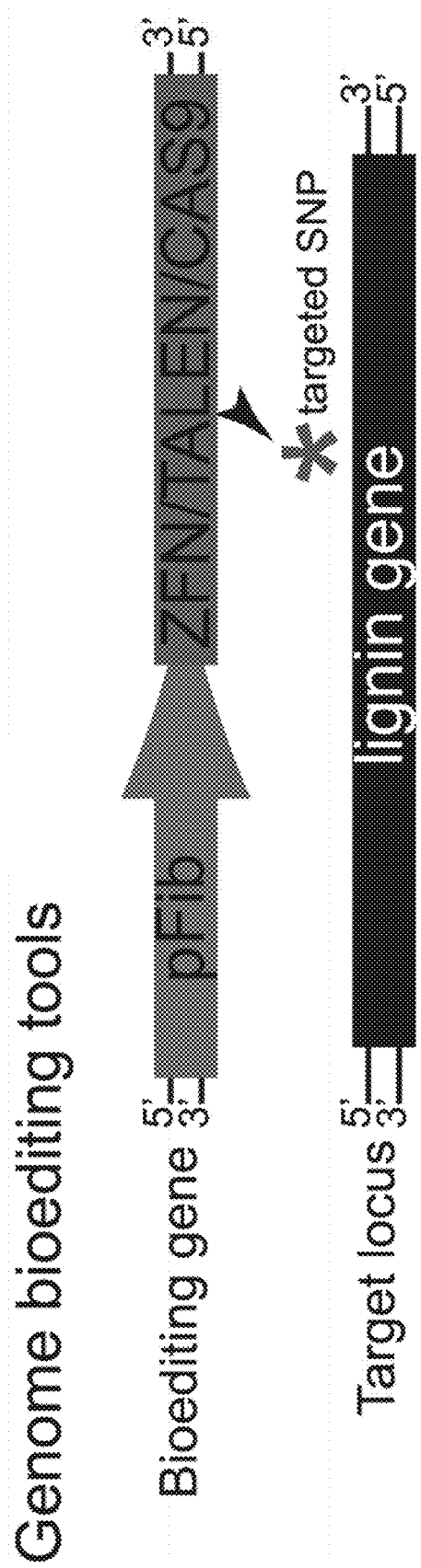
FIG. 2. Strategies for mutifaceted genetic engineering of plants. A) Genome bioediting tools showing target lignin locus (target of editing); grey arrow, fiber specific promoter used to drive the expression of the bioediting gene; bioediting gene: ZFNs, TALENs or CRISPR/CAS9; star, SNP generated when the genome bioediting gene is expressed.

These target-specific nuclease are used to introduce SNPs into essential lignin or xylan synthesis genes in targeted tissue such as fiber (FIG. 2). For example, using a fiber-specific promoter (e.g., pNST, pLAC17) to drive the expression of ZFNs, TALENs or CAS9 designed to recognize the genomic sequence of a key lignin biosynthetic gene (e.g., C4H, C3H, HCT, or CCR1) represses lignin biosynthesis only in fiber cells without affecting the lignification of vessel cells and other phenylpropanoid-derived pathways active in non-lignified tissues.

Methods and compositions for targeted cleavage of genomic DNA to introduce mutations have been described. See, for example, Urnov et al. (2010) Nature 435(7042): 646-51; United States Patent Publications 20030232410; 20050208489; 20050026157; 20050064474; 20060188987; 20090263900; 20090117617; 20100047805; 20110207221; 20110301073; 2011089775 and International Publication WO 2007/014275, the disclosures of which are incorporated by reference in their entireties for all purposes. Cleavage can occur through the use of specific nucleases such as engineered zinc finger nucleases (ZFNs), transcription-activator like effector nucleases (TALENs), or using the CRISPR/Cas system with an engineered crRNA/tracr RNA ('single guide RNA') to guide specific cleavage. U.S. Patent Publication No. 20080182332 describes the use of non-canonical zinc finger nucleases (ZFNs) for targeted modification of plant genomes; U.S. Patent Publication No. 20090205083 describes ZFN-mediated targeted modification of a plant EPSPS locus; U.S. Patent Publication No. 20100199389 describes targeted modification of a plant Zp15 locus and U.S. Patent Publication No. 20110167521 describes targeted modification of plant genes involved in fatty acid biosynthesis. Additional publications regarding use of Cas9, ZNF, and TALEN use in plants include Cermak, et al, *Nucleic Acids Research,* 39(12), e82, 2011; Curtin, et al., *Plant Physiology,* 156(2), 466-473, 2011; de Pater, et al., *Plant Biotechnology Journal,* 7(8), 821-835, 2009; Jiang, et at *Nucleic Acids Research,* 41(20), e188, 2013; Kim & Kim, (2011). *Plant Biotechnology Reports,* 5(1), 9-17, 2011; Li et al., *Nature Biotechnology,* 30(5), 390-392, 2012; Nekrasov, et al., *Nature Biotechnology,* 31(8), 691-693, 2013; Wang, et al., *RNA* (New York, N.Y.), 14(5), 903-913, 2008; Wendt et al., *Plant Molecular Biology,* 83(3), 279-285, 2013; Xie & Yang, RNA-guided Genome Editing in Plants Using A CRISPR-Cas System, *Molecular Plant,* 2013; and Zeevi et al., *Plant Physiology,* 158(1), 132-144, 2012). Each of the references is herein incorporated by reference.

Genome Editing Construct Components
CRISPR/CAS9 Constructs

In some embodiments, the genome editing nuclease system for targeting an enzyme to reduce lignin or xylan (C5 sugar) content in fiber cells in plants is a system comprising the CRISPR (Clustered Regularly Interspaced Short Palindromic Repeats)/Cas (CRISPR Associated) nuclease system. The CRISPR/Cas system is an engineered nuclease system based on a bacterial system that can be used for genome engineering. The CRISPR locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

Some bacteria and archaea genomes contain the CAS protein operon followed by CRISPR arrays, which are composed of direct repeats interspersed by small segments (protospacers) adopted from invading DNAs. Transcription of a CRISPR array, followed by enzymatic cleavage, yields short mature CRISPR RNA (crRNA). Through base pairing with a protospacer sequence in the invading DNA, crRNA guides the targeted degradation of invading DNA by recruiting CAS nucleases. A CRISPR/CAS genome bioediting system was developed based on the Type II CRISPR system from *Streptococcus pyogenes*, which contains the minimal CRISPR machinery composed of a single CAS9 protein, a crRNA with complementary sequence to the target site, and a trans-activating RNA (tracrRNA) that forms a hairpin with crRNA. A modified CRISPR/CAS9 system has been shown to drive targeted DNA cleavage in vitro (e.g., Gasiunas et al., *Proc. Natl. Acad. Sci. USA* 109:E2579-E2586, 2012; Jinek et al., Science 2012, 337:816-821, 2012) and was also used to induce mutations and edit genetic loci of interest in eukaryotes such as mouse and human cell lines (e.g., Cong et al., *Science* 2013, 339:819-823, Mali et al., *Science* 2013, 339:823-826, 2013). RNA-guided genome editing avoids intrinsic limitations in protein-guided genome editing, such as off-target mutagenesis activity due to imperfect protein-DNA recognition. RNA-guiding sequence in crRNA is readily programmable compared to the substantial effort required to generate customized DNA binding proteins. CRISPR/CAS9 also provides for multiplex genome bioediting. In addition, the CAS9 protein can be mutated to DNA nickase (e.g., Gasiunas, 2012, supra) to promote precise genome editing through HR. When a homology repair template was provided, a pair of restriction sites was inserted precisely into the target loci with the CRISPR/CAS nickase system (e.g., Gasiunas, 2012, supra).

As noted above, the Cas9 related CRISPR/Cas system comprises two RNA non-coding components: tracrRNA and a crRNA guide. To use a CRISPR/Cas system to accomplish genome editing in accordance with the invention, both functions of these RNAs are present (see Cong et al, 2013, supra. In some embodiments, the tracrRNA and pre-crRNAs are supplied via separate expression constructs or as separate RNAs. In typical embodiments of the present invention, a chimeric RNA is constructed where a sequence that targets an engineered mature crRNA (conferring target specificity) is fused to a tracrRNA (supplying interaction with the Cas9, also referred to herein as a Cas9 "handle") to create a chimeric cr-RNA-tracrRNA hybrid (also termed a single guide RNA). (see Jinek ibid and Cong, supra). In typical embodiments, the RNA guide as provided as a chimeric RNA that comprises the RNA targeting region and the Cas9-handle, which is the RNA that binds to Cas9.

In certain embodiments, Cas protein may be a variant of a naturally occurring Cas protein. That has the functional activity of a naturally occurring Cas protein, e.g., in the present invention, cleaving a DNA substrate and the ability to interact with the tracrRNA. The term "variants" as used herein includes biologically active fragments as well as sequences variants that differ from the native sequence of a Cas protein.

As used herein, a "nuclear-targeted Cas protein" or a "nuclear-targeted Cas domain" refers to a Cas protein fused to a nuclear localization signal.

ZFN and TALEN Constructs

ZFN and TALEN constructs each comprise a nucleic acid sequence encoding a cleavage domain fused to nucleic acid sequence encoding a DNA binding domain. The cleavage domain is heterologous to the DNA-binding domain, i.e., it is from a different protein, and is typically an endonuclease domain.

Restriction endonucleases (restriction enzymes) are present in many species and are capable of sequence-specific binding to DNA (at a recognition site), and cleaving DNA at or near the site of binding. Type IIS enzymes cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269: 31,978-31,982. Thus, in typical embodiments, a ZFN or TALEN genome editing construct of the invention comprises a cleavage domain from a Type IIS restriction enzyme.

Examples of Type IIS restriction enzymes are described in International Publication WO 07/014,275, which is incorporated by reference. Additional restriction enzymes also contain separable binding and cleavage domains (see, e.g., Roberts et al., *Nucleic Acids Res.* 31:418-420, 2003).

In some embodiments, the cleavage domain is from the Type IIS restriction FokI or Sts1. FokI dimerizes in order to cleave DNA and thus a pair of ZFNs or TALENS are typically used to target non-palindromic DNA sites. In typical embodiments, the cleavage domain is joined to the C-terminus of the zinc finger domain (for ZFNs) or TALE DNA binding domain (for TALENS).

Cleavage domains for use in a pair of ZFNs or TALENS can be obtained from any nuclease that requires dimerization for cleavage activity. The two domains are typically obtained from the same endonuclease, although they can be derived from different endonucleases, so long as the domains are capable of dimerizing.

In certain embodiments, the cleavage domain employed in each member of the ZFN or TALEN pair is engineered to reduce homodimerization in order to reduce the number of off-target cleavage events. Examples of FokI domain mutants engineered to minimize or prevent homodimerization, are, for example, in U.S. Patent Publication Nos. 20050064474; 20060188987; 20070305346 and 20080131962, the disclosures of all of which are incorporated by reference in their entireties herein.

Design of ZFNs and TALENs to Produce Double Stranded DNA Breaks within the Target Genes.

Zinc finger and TALE binding domains are "engineered" to bind to a predetermined nucleotide sequence, for example via engineering (altering one or more amino acids) of the recognition helix region of a naturally occurring zinc finger. Similarly, TALEs can be "engineered" to bind to a predetermined nucleotide sequence, for example by engineering of the amino acids involved in DNA binding (the repeat variable diresidue or RVD region). Therefore, engineered DNA binding proteins (zinc fingers or TALEs) are proteins that are non-naturally occurring.

As noted above, in order to generate double stranded DNA breaks within a target DNA sequence, ZFNs or TALENs are expressed by pairs: ZFN-left/ZFN-right and TALEN-left/TALEN-right.

In certain embodiments, proteins encoding for ZFNs and TALENs are composed of 3 parts: Nuclear localization signal; DNA-binding domain and a nuclease (e.g., FokI). Such proteins can be designed based on known parameters or customized by different companies. In both cases, the first step is to identify a target DNA site within the gene of interest to which ZFNs or TALENs will bind and cleave. The second step is to design and/or select various DNA-binding peptides that will bind to the chosen target site with high specificity and affinity. The DNA coding sequence for the designed DNA-binding peptides are then fused in frame to the sequence encoding the cleavage domain, e.g., a Fok1 cleavage domain, and a nuclear localization signal peptide. In order design ZFNs and TALENs (ZFN: Carroll, *Genetics*, 188(4), 773-782, 2011; Urnov, et al., *Nature Reviews Genetics*, 11(9), 636-646, 2010; Kandavelou & Chandrasegaran, *Methods in Molecular Biology* (Clifton, N.J.), 544, 617-636, 2009; Durai, et al., *Nucleic Acids Research*, 33(18), 5978-5990, 2005; TALEN: Cermak, et al, *Nucleic Acids Research*, 39(12), e82, 2011; Heigwer, et al., *Nucleic Acids Research*, 41(20), e190, 2013), highly specific DNA binding peptides are generated that recognize specific sites with the target DNA. The encoding sequence of DNA binding domains of ZFNs are designed to recognize specific sites with the target DNA sequence, e.g., with the support of online tools using http www site scripps.edu/mb/barbas/zfdesign/zfdesign-home.php; and http site bindr.gdcb.iastate.edu:88/. The same approach can be employed for designing DNA binding domains of the TALEN proteins using online tools, e.g., http site zifit.partners.org/ZiFiT/ChoiceMenu.aspx; and http www site talen-design.de/.

Alternatively, ZFNs and TALENs can be directly custom-designed commercially. For example, ZFNs can be designed and obtained from Sangamo Biosciences (Richmond, Calif., USA), http www site sangamo.com/technology/zf-nuclease-s.html; and Sigma-Aldrich (St. Louis, Mo., USA), http www site sigmaaldrich.com/life-science/zinc-finger-nuclease-technology.html. TALENs can be designed and obtained from Cellectis Bioresearch (Paris, France), http www site cellectis-bioresearch.com/products/talen-basic; Transposagen Biopharmaceuticals (Lex ington, Ky., USA), http site transposagenbio.com/gene-modification-tools/xtn-talens/; Life Technologies (Grand Island, N.Y., USA), http www site lifetechnologies.com/us/en/home/life-science/cloning/gene-synthesis/geneart-precision-tals.html?s_kwcid=AL!3652!3!27458483601!b!!g!!+zinc%20+finger&ef_id=UeJPbgAAAQOPs jpF:20140114113126:s.

Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534, 261; see also WO 98/53058; WO 98/53059; WO 98/53060; WO 02/016536 and WO 03/016496 and U.S. Publication Nos. 20110301073, 20110239315 and 20119145940.

The invention thus provides a DNA-binding domain (e.g., zinc finger protein (ZFP) or TALE domain) that specifically binds to a gene encoding a protein involved in lignin or xylan production. The zinc finger protein can comprise one or more zinc fingers (e.g., 2, 3, 4, 5, 6, 7, 8, 9 or more zinc fingers), and can be engineered as described above to bind to a target sequence within any lignin or xylan biosynthesis gene. The target sequence may be within the coding region of the gene or in a non-coding region within or adjacent to a gene, such as a promoter or other expression element, so long as the expression of the gene is inhibited. One or more of the component zinc finger binding domains of the zinc finger protein can be a canonical (C2H2) zinc finger or a non-canonical (e.g., C3H) zinc finger (e.g., the N-terminal and/or C-terminal zinc finger can be a non-canonical finger).

A TALE domain comprises a TAL effector DNA binding domain. See, e.g., U.S. Patent Application Publication No. 20110301073, incorporated by reference. One of the most well characterized TAL-effectors is AvrBs3 from Xanthomonas campestris pv. Vesicatoria (Bonas et al., *Mol Gen Genet.* 218: 127-136, 2989 and WO2010079430). TAL-effectors contain a centralized domain of tandem repeats, each repeat containing approximately 34 amino acids, which are important to the DNA binding specificity of these proteins. Specificity of these TAL effectors depends on the sequences found in the tandem repeats. The repeated sequence comprises approximately 102 bp and the repeats are typically 91-100% homologous with each other (Bonas et al., supra). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, *Science* 326:1501, 2009 and Boch et al. *Science* 326:1509-1512, 2009). TALE domains that target genes encoding lignin or xylan synthesis genes in accordance with the invention are engineered as noted above using known methods.

Plants Having Reduced Lignin, C5-Sugar Rich Polymers (Xylan), or Acetate Content In one aspect, the present invention provides a method of engineering a plant having reduced lignin content (e.g., reduced amount of lignin polymers, reduced size of lignin polymers, reduced degree of branching of lignin polymers, or reduced space filling) in a desired tissue, e.g., fiber cells or secondary walls. In the present invention a gene targeted by gene editing in accordance with the invention is a lignin biosynthesis gene. In some embodiments, the gene is phenylalanine ammonia lyase (PAL) (e.g., accession number NM_129260 or NP_181241), cinnamate 4-hydroxylase (C4H) (e.g.,I accession number NM_128601 or NP_180607), 4-coumarate-CoA ligase (4CL) (e.g., accession number NM_113019 or NP_188761), hydroxycinnamoyl CoA:shikimate hydroxycinnamoyl transferase (HCT) (e.g., accession number NM_124270 or NP_199704), coumaryol shikimate 3-hydroxylase (C3H) (e.g., accession number NM_119566 or NP_850337), or cinnamoyl-CoA reductase 1 (CCR1) (e.g., accession number NM_101463 or NP_173047). In some embodiments, the gene is a xylan biosynthesis gene. In some embodiments, the gene is irregular xylem 8 (IRX8), IRX14, IRX14-like, IRX9, IRX9-like, IRX7, IRX10, IRX10-like, IRX15, IRX15-like, F8H, or PARVUS. In some embodiments, the xylan biosynthesis enzyme is IRX9. In some embodiments, the gene is a Myb gene. In some embodiments, the targeted gene is involved in xylan 0-acetylation and thus can be targeted to reduce acetate content. In some embodiments the gene is RWA or TBL (e.g., Grille & Pauly, *Frontiers in Plant Science* 3:12, 2012; Pawar et al, *Frontiers in Plant Science* 4:118, 2013). In some embodiments, the xylan O-acetylation enzyme is a member of the Trichome Birefringence Like family of proteins (PF03005 family also known as Domain of Unknown Function 231). Illustrative accession numbers for xylan biosynthesis genes and genes involved in acetate production are provided in WO2012/103555. The accession numbers listed herein and provided in WO2012/103555 are examples. One of skill understands that corresponding genes in other plant types can be easily identified.

As appreciated by one of skill in the art, the isoforms that are highly expressed in and fibers are targeted. For example, using *Arabidopsis* for illustration purposes, IRX7, IRX8, IRX9, PARVUS, IRX15 are highly expressed in fibers and would therefore be targeted. Similarly, for making plants that are inhibited in Rwa expression, the isoforms that are expressed in fibers are targeted. For example, again using *Arabidopsis* for illustration, one of, typically two or more of, RWA1, RWA3 and RWA4 are targeted (RWA2 is not expressed in fibers).

Sequences within the gene of interest are identified for cleavage. The cleavage site can be anywhere within the gene or flanking the coding region, so long as cleavage results in reduced activity of the lignin or xylan biosynthesis gene.

Fiber and Secondary Wall-Specific Promoters

A nucleic acid encoding a nuclease editing construct in accordance with the invention is targeted to a fiber cell using a fiber-specific promoter. Examples of such promoters include a NAC secondary wall-thickening promoting factor 1 (NST1), NST2, or NST3 promoter; and Lac17. Illustrative NST1, NST2, and NST3 promoter sequences are provided in SEQ ID NOs. 22, 23, and 24, respectively. Such promoters are also described in the art. See, for example, Mitsuda et al., *Plant Cell* 17:2993-3006 (2005); Mitsuda et al., *Plant Cell* 19:270-280 (2007); Zhong et al., *Plant Cell* 18:3158-3170, 2006; and Berthet et al., *The Plant Cell* 23:1124-37, 2011.

In some embodiments, the promoter employed in the genome editing is heterologous relative to the target gene, e.g., the promoter and the target gene may be from two different species. A promoter is suitable for use as a fiber cell-specific promoter if the promoter is expressed strongly in fiber cells as compared to other non-fiber cells of the plant.

It will be appreciated by one of skill in the art that a promoter region can tolerate considerable variation without diminution of activity. Thus, in some embodiments, a promoter (e.g., a secondary cell wall-specific promoter, or a fiber cell-specific promoter) is substantially identical (e.g., at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or at least 99% identical) to an NST1, NST2, or NST3, polynucleotide sequence of any of SEQ ID NOs:22, 23, or 24. In some embodiments, a promoter comprises at least 200 nucleotides, or at leaset 300, 500, 750, 1000, 1250, 1500, or 2000 contiguous nucleotides of a sequence of SEQ ID NO:22, 23, or 24. The effectiveness of a promoter may be confirmed using a reporter gene (e.g., β-glucuronidase or GUS) assay known in the art.

As understood in the art, a promoter region, e.g, can be obtained from the 5' upstream region of a gene, e.g., a regions of anywhere from 100, 200, 300, 400, 500, 600, 750, or 1000 to 2000 bp is isolated upstream of the translation start site, or the transcription start site, and can be evaluated for fiber-specific promoter activity for use in the invention using well-known assays.

Additional Construct Components

As understood in the art, a genome editing construct to target a lignin biosynthesis gene or xylan biosynthesis gene in accordance with the invention also comprises additional sequences, which are well known in the art. For example, a Cas9 construct comprises one, or more, for example, where there are two target sites encoded by a single construct, ribosomal RNA promoters. Such promoters are well known in the art. Illustrative examples are a AtU6-26pG promoter, a pOsU6pG promoter, a pAt7SL-1pG promoter, a pAt7SL-2pG promoter, a pAtU3B-1pA promoter, and a pAtU3B-2pA promoter (see, for example, the illustrative sequences provided in SEQ ID NOs:25-30, respectively).

A genome editing construct of the invention also comprises a nuclear localization signal to target the nuclease to the nucleus. Nuclear localization signals are well known in the art. Examples include the sequences: GPKKKRKV (SEQ ID NO:34); APKKKRKVG (SEQ ID NO:35); and GPKKKRKVAAAAPKKKRKVG (SEQ ID NO:36). All three of these illustrative sequences contain a PKKKRKV (SEQ ID NO:37) domain (Kalderon, et al., *Cell,* 39:499-509, 1984). Other examples of sequences are described in Grebenok et al., *The Plant Journal: for Cell and Molecular Biology,* 11:573-586, 1997.

Illustrative Cas9, ZFN, and TALEN Genome Editing Constructs of the Invention.

In some embodiments, a CAS9 construct in accordance with the invention comprises a fiber-specific promoter such as an NST1 promoter operably linked to a sequence encoding a nuclear-targeted Cas9 nuclease. In certain embodiments, the construct comprises a sequence encoding an RNA guide sequence that target a CH4 gene, e.g., SEQ ID NO:1, 2, or 3. In some embodiments, a CAS9 construct in accordance with the invention has an NST1 promoter operably linked to a sequence encoding a nuclear-targeted Cas9 nuclease where the construct comprises a sequence encoding an RNA targeting sequence that targets a CH3 gene, e.g., SEQ ID NO:4, 5, or 6. In some embodiments, a CAS9 construct in accordance with the invention has an NST1 promoter operably linked to a sequence encoding a nuclear-targeted Cas9 nuclease where the construct comprises a sequence that encodes an RNA targeting sequence that targets an HCT gene, e.g., SEQ ID NO:7, 8, or 9. In some embodiments, a CAS9 construct in accordance with the invention has an NST1 promoter operably linked to a sequence encoding a nuclear targeted Cas9 nuclease where the construct comprises s sequence encoding an RNA targeting sequence that targets a CCR gene, e.g., SEQ ID NO:10, 11, or 12. In some embodiments, a CAS9 construct in accordance with the invention has an NST1 promoter operably linked to a sequence encoding a nuclear targeted Cas9 nuclease where the construct comprises a sequence encoding an RNA targeting sequence that targets a Myb gene, e.g., SEQ ID NO:13, 14, or 15. In some embodiments, a CAS9 construct in accordance with the invention has an NST1 promoter operably linked to a sequence encoding a nuclear-targeted Cas9 nuclease where the construct comprises a sequence encoding an RNA targeting sequence that targets an IRX7 gene, e.g., SEQ ID NO:16, 17, or 18. In some embodiments, a CAS9 construct in accordance with the invention has an NST1 promoter operably linked to a sequence encoding a nuclear-targeted Cas9 nuclease where the construct comprises a sequence encoding an RNA targeting sequence that targets an IRX8 gene, e.g., SEQ ID NO:19, 20, or 21. In the these embodiments, the RNA targeting sequence is present in a chimeric sequence that has a Cas9 "handle" that contains a hairpin region to which Cas proteins bind to either cut the target DNA sequence or silence it.

The sequence of an illustrative Cas9 construct that targets a CH4 gene is provided in SEQ ID NO:31.

In some embodiments, a CAS9 construct of the invention may comprise two, or more, RNA targeting sequences that target two or more sites on a single gene, or that target two or more sites where the sites are present on two genes or more. In some embodiments, such a construct comprises a promoter, e.g., an NST1 promoter, operably linked to a sequence encoding a CAS9 nuclease, and a sequence encoding a first RNA guide that targets a first site on a gene such as C4H, and a second RNA guide that targets a second site on a C4H gene. In some embodiments, a Cas9 construct comprises a promoter, e.g., an NST1 promoter, operably linked to a sequence encoding a CAS9 nuclease, and a sequence encoding a first RNA guide that targets a first site on a gene such as IRX7, and a second RNA guide that targets a site on a second gene, e.g., a C4H gene.

The sequence of an illustrative Cas9 construct that targets two sites in a C4H gene is provided in SEQ ID NO:32.

The sequence of an illustrative Cas9 construct that that targets a site in an IRX7 gene and a second site in a C4H gene is provided in SEQ ID NO:33.

In some embodiments, a genome editing construct of the invention is a TALEN construct. For example, in certain embodiments, a TALEN construct comprises: a fiber-specific promoter such as a NST1 promoter operably linked to a right TALEN nuclease that comprises a sequence encoding a binding domain to the target gene of interest, e.g., a C4H gene, fused to a nuclease domain, e.g., a Fok1 nuclease domain; and a second transcription unit in which a second promoter, typically a different fiber-specific promoter from the first promoter, e.g., in this example NST3, is operably linked to a left TALEN nuclease that comprises a sequence encoding a DNA binding domain that targets the gene of interest, in this example, C4H, fused to the nuclease domain, in this example, a Fok1 nuclease domain.

In some embodiments, a genome editing construct of the invention is a ZFN construct. For example, in certain embodiments, a ZFN construct comprises: a fiber-specific promoter such as a NST1 promoter operably linked to a right ZFN nuclease that comprises a sequence encoding a binding domain to the target gene of interest, e.g., a C4H gene, fused to a nuclease domain, e.g., a Fok1 nuclease domain; and a second transcription unit in which a second promoter, typically a different fiber-specific promoter from the first promoter, e.g., in this example NST3, is operably linked to a left ZFN that comprises a sequence encoding a DNA binding domain that targets the gene of interest, again in this example, C4H, fused to the nuclease domain, in this example, a Fok1 nuclease domain.

An expression cassette targeting as described herein, when introduced into a plant, results in reduced activity of a lignin or xylan biosynthesis gene targeted by the nuclease construct, and results in reduced lignin and/or xylan content, or where the xylan biosynthesis gene targets acetylation, reduced acetate content, that is specifically localized to fiber cells, thus reducing cell wall recalcitrance to enzymatic hydrolysis and/or C5-sugar content while avoiding defects in plant growth or reductions in biomass yield.

Preparation of Recombinant Expression Vectors

The sequences of the components of a genome editing construct in accordance with the invention are used to prepare an expression cassette for expressing constructs in a plant. Typically, plant transformation vectors in accordance with the invention include the promoters, nuclease cleavage domains and targeting regions as well as additional regulatory sequences and a dominant selectable marker. Such plant transformation vectors may also include RNA processing regulatory sequences from the 3'-untranslated region of plant genes, e.g., a 3' terminator region to increase RNA stability. Other modifications, e.g., in the 5' or 3' untranslated region or in the coding sequence, may also be made to reduce RNA stability in other cells than fiber cells.

Plant expression vectors routinely also include dominant selectable marker genes to allow for the ready selection of transformants. Such genes include those encoding antibiotic resistance genes (e.g., resistance to hygromycin, kanamycin, bleomycin, G418, streptomycin or spectinomycin), herbicide resistance genes (e.g., phosphinothricin acetyltransferase), and genes encoding positive selection enzymes (e.g. mannose isomerase).

Once a genome editing construct of the invention as described herein has been constructed, standard techniques may be used to introduce the polynucleotide into a plant in order to modify gene expression. See, e.g., protocols described in Ammirato et al. (1984) Handbook of Plant Cell Culture—Crop Species. Macmillan Publ. Co. Shimamoto et al. (1989) Nature 338:274-276; Fromm et al. (1990) Bio/Technology 8:833-839; and Vasil et al. (1990) Bio/Technology 8:429-434.

Transformation and regeneration of plants are known in the art, and the selection of the most appropriate transformation technique will be determined by the practitioner. Suitable methods may include, but are not limited to: electroporation of plant protoplasts; liposome-mediated transformation; polyethylene glycol (PEG) mediated transformation; transformation using viruses; micro-injection of plant cells; micro-projectile bombardment of plant cells; vacuum infiltration; and *Agrobacterium tumeficiens* and *rhizogenes* mediated transformation. In certain embodiments, the construct is expressed transiently. Examples of these methods in various plants include: U.S. Pat. Nos. 5,571,706; 5,677,175; 5,510,471; 5,750,386; 5,597,945; 5,589,615; 5,750,871; 5,268,526; 5,780,708; 5,538,880; 5,773,269; 5,736,369 and 5,610,042.

Following transformation, plants can be selected using a dominant selectable marker incorporated into the transformation vector. Typically, such a marker will confer antibiotic or herbicide resistance on the transformed plants or the ability to grow on a specific substrate, and selection of transformants can be accomplished by exposing the plants to appropriate concentrations of the antibiotic, herbicide, or substrate.

Plants in which Lignin, Xylan, or Acetate Content can be Reduced

A genome editing construct in accordance with the invention can be expressed in various kinds of plants. The plant may be a monocotyledonous plant or a dicotyledonous plant. In some embodiments of the invention, the plant is a green field plant. In some embodiments, the plant is a gymnosperm or conifer.

In some embodiments, the plant is a plant that is suitable for generating biomass. Examples of suitable plants include, but are not limited to, *Arabidopsis*, poplar, eucalyptus, rice, corn, switchgrass, sorghum, millet, miscanthus, sugarcane, pine, alfalfa, wheat, soy, barley, turfgrass, tobacco, hemp, bamboo, rape, sunflower, willow, Jatropha, and *Brachypodium*.

In some embodiments, the plant into which the genome editing construct is introduced is a species different from the plant from which the promoter was obtained. In some embodiments, the species is the same species from which the promoter was obtained. In typical embodiments, the targeting sequences that direct nuclease activity to the gene of interest is specific to a species, but in instance where the targeting sequence is highly conserved across species, may be employed in any of the species in which the sequence is conserved.

Screening for Plants Having Reduced Lignin, Xylan, or Acetate Content

After transformed plants are selected, the plants or parts of the plants can be evaluated to determine whether expression of the genome editing construct of the invention resulted in reduced activity of the targeted gene. This may be assessed using any number of methods, e.g., by evaluating the level of RNA or protein, by measuring enzymatic activity of the protein, and/or by evaluating the lignin content, xylan content, or acetate content, in the fiber cells in the plant. These analyses can be performed using any number of methods known in the art.

In some embodiments, plants are screened by evaluating the level of RNA or protein. Methods of measuring RNA expression are known in the art and include, for example, PCR, northern analysis, reverse-transcriptase polymerase chain reaction (RT-PCR), and microarrays. Methods of measuring protein levels are also known in the art and include, for example, mass spectroscopy or antibody-based techniques such as ELISA, Western blotting, flow cytometry, immunofluorescence, and immunohistochemistry.

In some embodiments, plants are screened by assessing for activity of a lignin biosynthesis target protein and by evaluating lignin content. Enzymatic assays for the lignin biosynthesis proteins are well known in the art. Lignin can be assessed, for example, by nuclear magnetic resonance (NMR), spectrophotometry, microscopy, klason lignin assays, thioacidolysis, acetyl-bromide reagent or by histochemical staining (e.g., with phloroglucinol). Xylan content can be assessed, for example, by immunohistochemistry (e.g., with LM10 monoclonal antibody). The amount of secondary cell wall deposition can be assessed, for example, by histochemical staining (e.g., phloroglucinol or Maule reagent) or enzymatic or chemical reaction (e.g., polysaccharide hydolysis or TFA hydrolysis). Illustrative methods of testing acetate levels are described in WO 2010/096488, incorporated by reference.

As a non-limiting example, any of several methods known in the art can be used for quantification and/or composition analysis of lignin in a plant or plant part as described herein. Lignin content can be determined from extract free cell wall residues using acetyl bromide or Klason methods. See, e.g., Eudes et al., *Plant Biotech. J.* 10:609-620 (2012); Yang et al., *Plant Biotech. J.* (2014); and Dence et al. (eds) *Lignin determination*. Berlin: SpringerVerlag (1992); each of which is incorporated by reference herein. Extract free cell wall residues correspond to raw biomass, which has been extensively washed to remove the ethanol soluble component. Eudes et al., *Plant Biotech. J.* 10:609-620 (2012); Yang et al., *Plant Biotech. J.* (2014); Sluiter et al., Determination of structural carbohydrates and lignin in biomass. In: Laboratory *Analytical Procedure*. National Renewable Energy Laboratory, Golden, Colo., USA; and Kim et al., *Bio. Res.* 1:56-66 (2008). Lignin composition analysis and G/S lignin subunit determination can be performed using any of various techniques known in the art such as 2D 13C-H1 HSQC NMR spectroscopy (Kim and Ralph, *Org. Biomol. Chem.* 8:576-591 (2010); Kim et al., *Bio. Res.* 1:56-66 (2008)); thioacidolysis method (Lapierre et al., *Plant Physiol.* 119:153-164 (1999); Lapierre et al., *Res. Chem. Intermed.* 21:397-412 (1995); Eudes et al., *Plant Biotech. J.* 10:609-620 (2012)); derivatization followed by reductive cleavage method (DFRC method; Lu and Ralph, *J. Agr. Food Chem* 46:547-552 (1998) and Lu and Ralph, *J. Agr. Food Chem* 45:2590-2592 (1997)) and pyrolysis-gas chromatograph method (Py-GC method; Sonoda et al., *Anal. Chem.* 73:5429-5435 (2001)) directly from extract free cell wall residues or from cellulolytic enzyme lignin (CEL lignin). CEL lignin derives from cell wall residues, which were hydrolyzed with crude cellulases to deplete the polysaccharide fraction and enrich the lignin one (Eudes et al., *Plant Biotech. J.* 10:609-620 (2012)).

Methods of Using Plants Having Reduced Lignin Content

Plants, parts of plants, or plant biomass material from plants having reduced lignification and/or reduced xylan (C5 sugar content) resulting from inhibition of one or more lignin or xylan synthesis genes in accordance with the invention, can be used for a variety of methods. In some embodiments, the plants, parts of plants, or plant biomass material generate less recalcitrant biomass for use in a conversion reaction as compared to wild-type plants. In some embodiments, the plants, parts of plants, or plant biomass material are used in a saccharification reaction, e.g., enzymatic saccharification, to generate soluble sugars at an increased level of efficiency as compared to wild-type plants. In some embodiments, the plants, parts of plants, or plant biomass material are used to increase biomass yield or simplify downstream processing for wood industries (such as paper, pulping, and construction) as compared to wild-type plants. In some embodiments, the plants, parts of plants, or plant biomass material are used to increase the quality of wood for construction purposes. In some embodiments the plants, parts of plants, or plant biomass material can be used in a combustion reaction, gasification, pyrolysis, or polysaccharide hydrolysis (enzymatic or chemical). In some embodiments, the plants, parts of plants, or plant biomass material are used as feed for animals (e.g., ruminants).

Methods of conversion, for example biomass gasification, are known in the art. Briefly, in gasification plants or plant biomass material (e.g., leaves and stems) are ground into small particles and enter the gasifier along with a controlled amount of air or oxygen and steam. The heat and pressure of the reaction break apart the chemical bonds of the biomass, forming syngas, which is subsequently cleaned to remove impurities such as sulfur, mercury, particulates, and trace materials. Syngas can then be converted to products such as ethanol or other biofuels.

Methods of enzymatic saccharification are also known in the art. Briefly, plants or plant biomass material (e.g., leaves and stems) are optionally pre-treated with hot water, dilute alkaline, AFEX (Ammonia Fiber Explosion), ionic liquid or dilute acid, followed by enzymatic saccharification using a mixture of cell wall hydrolytic enzymes (such as hemicellulases, cellulases and beta-glucosidases) in buffer and incubation of the plants or plant biomass material with the enzymatic mixture. Following incubation, the yield of the saccharification reaction can be readily determined by measuring the amount of reducing sugar released, using a standard method for sugar detection, e.g. the dinitrosalicylic acid method well known to those skilled in the art. Plants engineered in accordance with the invention provide a higher saccharificaton efficiency as compared to wild-type plants, while the plants' growth, development, or disease resistance is not negatively impacted.

EXAMPLES

The following examples are provided to illustrate, but not limited the claimed invention.

Example 1: Generation of Chimeric Plants

This example illustrates the generation of chimeric plants such that only specific cells/tissues will harbor new allelic variants for specific genes in contrast to the rest of the plant using bioediting tools that are genetically encoded. In other words these genome editing tools are used to cause in vivo mutagenesis in specific cell types. In this example, native alleles are converted into new ones that encode for truncated, unstable, non-functional or poorly active proteins. This can be achieved by expressing under tissue specific promoters DNase(s)—protein complex, chimeric protein, protein/RNA or DNA chimera—that are designed to recognize a specific sequence within the target gene and cause a double stranded DNA break within the target gene. These DNA breaks are "repaired" by the native DNA repair system of the cell, which is usually imperfect and is accompanied with point mutations or deletions at the repaired locus. There are 3 types of bioediting tools that can be genetically encoded: Zinc finger nucleases (ZFN), TALENs and CRISPR/Cas9. All of them can be designed to recognize and cleave defined DNA targets (Strauss et al. 2013).

The first illustrative application was to reduce lignin and xylan content independently or simultaneously in fiber tissues in order to improve biomass quality for bioenergy (reduction of biomass recalcitrance and increase of C6/C5-sugar ratio respectively). We generated several binary vectors that harbor within the tDNA a DNA fragment designed to express Cas9 protein fused to a nuclear localization sequence under the control of a fiber specific promoter and one or several DNA fragments encoding for one or several chimeric RNA (each composed of guide RNA and Cas9 handle), each under the control of ribosomal RNA promoters (e.g. pAtU6-26pG, pOsU6pG, pAt7SL-1pG, pAt7SL-2pG, pAtU3B-1pA, pAtU3B-2pA; Wang et al. 2008; Jiang et al. 2013). Each chimeric RNA is designed to recognize DNA sequence from a target locus/gene and is expressed at least at the same time and in the same cells/target cells (e.g. fiber cells) as a nuclear-targeted Cas9 protein. A complex Cas9 chimeric RNA is formed, recognizes the DNA target locus/loci, and causes a double stranded DNA break. A single locus or multiple loci can be targeted at the same time in the same cell. It requires that a single chimeric RNA designed to recognize the same sequence at multiple genomic loci or multiple chimeric RNAs each designed to recognize a specific sequence are expressed at the same time as a nuclear-targeted Cas9 protein.

The primary goal in this example was to reduce flux though the lignin biosynthesis pathway in order to reduce lignin and to disturb xylan biosynthesis to reduce xylan content specifically in fiber cells. We designed several chimeric RNAs such that they will target key genes in both pathways for example C4H, C3H and CCR1 for the lignin biosynthesis pathway and IRX7 and IRX8 for the xylan biosynthesis pathway. Some were also designed to target key transcription factor known to positively regulator of the lignin biosynthesis pathway such as Myb63. Each of them can be used alone or co-expressed together, but needs to be expressed at the same time and same cells as Cas9 protein. The ability to express several of them at once to target several loci in one gene or different genes increases the efficiency of metabolic pathway repression as it increases mutagenesis probability within the target pathway (e.g. lignin). Furthermore, it can be used to target multiple biosynthesis pathways in a single cell type such as lignin and xylan.

In other examples, competitive pathways in specific cell types can be eliminated or inhibited to enhance yield of a desired product.

Figure 3:
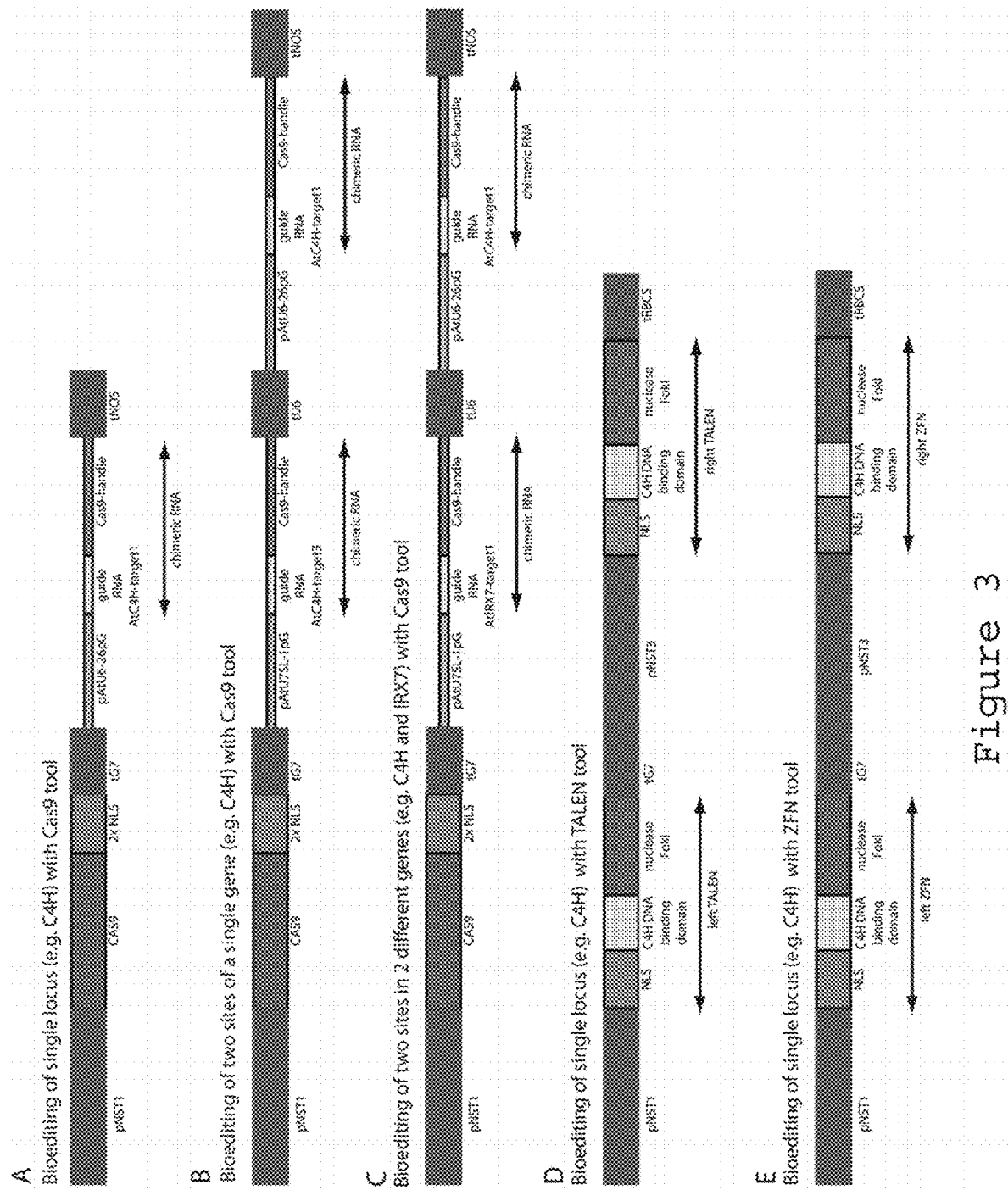
FIG. 3 provides illustrative genome editing construct schematics of the invention.

Examples of DNA construct designs for bioediting of lignin and xylan genes are shown in FIG. 3. A) DNA construct designed to bioedit a single site in the C4H lignin gene in fiber cells using Cas9 system approach. B) DNA construct designed to bioedit two sites in the C4H lignin gene in fiber cells using Cas9 system approach. C) DNA construct designed to bioedit two sites, one in xylan gene IRX7 and a second one in the lignin gene C4H in fiber cells using a Cas9 system approach. D) DNA construct designed to bioedit a single site in the C4H lignin gene in fiber cells using a TALEN approach. E) DNA construct designed to bioedit a single site in the C4H lignin gene in fiber cells using a ZFN system approach. A, B and C are composed of a single promoter for fiber specific expression (e.g. pNST1) to drive the expression of a nuclear-targeted CAS9 in fiber cells followed by a terminator and one or multiple chimeric RNA expression cassette. A chimeric RNA expression cassette is composed of a ribosomal promoter (e.g. pAtU6-26pG; pAtU7SL-1pG) followed by a chimeric RNA composed of a guide RNA (e.g. AtCH4 Target1; AtCH4 Target3; AtIRX7 Target1) and Cas9-handle, and a terminator (e.g. tU6; tNOS). D and E are composed of promoter for fiber specific expression (e.g. pNST1) to drive the expression of the right TALEN or right ZFN in fiber cells followed by a terminator and second promoter for pNST1 coexpression (e.g. pNST3) to drive the expression of the left TALEN or left ZFN followed by a terminator; both TALEN and ZFN are composed of a nuclear localization signal (NLS), a DNA binding domain designed to recognize the target locus and a nuclease such as FokI.

Example of Chimeric RNA Targeting Lignin Genes in Fiber Cells

C4H

```
>AtC4H-target1
                                                          (SEQ ID NO: 1)
gtcgattacgctaagaaattGTTTTAGAGCTAGAAATAGCAAGTTAAAATAAGGCTAGTCCGTTA

TCAACTTGAAAAAGTGGCACCGAGTCGGTG

>AtC4H-target2
                                                          (SEQ ID NO: 2)
gatctcttcctcctccgtatGTTTTAGAGCTAGAAATAGCAAGTTAAAATAAGGCTAGTCCGTTA

TCAACTTGAAAAAGTGGCACCGAGTCGGTG

>AtC4H-target3
                                                          (SEQ ID NO: 3)
gaatccagattctgctacgaaGTTTTAGAGCTAGAAATAGCAAGTTAAAATAAGGCTAGTCCGTT

ATCAACTTGAAAAAGTGGCACCGAGTCGGTG
```

C3H

```
>AtC3H-target1
                                                          (SEQ ID NO: 4)
gtaacctctacgacataaaacGTTTTAGAGCTAGAAATAGCAAGTTAAAATAAGGCTAGTCCGTT

ATCAACTTGAAAAAGTGGCACCGAGTCGGTG

>AtC3H-target2
                                                          (SEQ ID NO: 5)
gatcttatatgggccgattatGTTTTAGAGCTAGAAATAGCAAGTTAAAATAAGGCTAGTCCGTT

ATCAACTTGAAAAAGTGGCACCGAGTCGGTG

>AtC3H-target3
                                                          (SEQ ID NO: 6)
gattatgggcctcattacgtgaGTTTTAGAGCTAGAAATAGCAAGTTAAAATAAGGCTAGTCCGTT

ATCAACTTGAAAAAGTGGCACCGAGTCGGTG
```

HCT

```
>AtHCT-target1
                                                          (SEQ ID NO: 7)
gtcgcttgaagagagacgatgaGTTTTAGAGCTAGAAATAGCAAGTTAAAATAAGGCTAGTCCGT

TATCAACTTGAAAAAGTGGCACCGAGTCGGTG
```

-continued

>AtHCT-target2
(SEQ ID NO: 8)
gtctacttctacagacccacGTTTTAGAGCTAGAAATAGCAAGTTAAAATAAGGCTAGTCCGTTA

TCAACTTGAAAAAGTGGCACCGAGTCGGTG

>AtHCT-target3
(SEQ ID NO: 9)
gtccctttttaccctatggcGTTTTAGAGCTAGAAATAGCAAGTTAAAATAAGGCTAGTCCGTTA

TCAACTTGAAAAAGTGGCACCGAGTCGGTG

---
CCR
---

>AtCCR1-target1
(SEQ ID NO: 10)
gttgcgacggcgtctttcacaGTTTTAGAGCTAGAAATAGCAAGTTAAAATAAGGCTAGTCCGTT

ATCAACTTGAAAAAGTGGCACCGAGTCGGTG

>AtCCR1-target2
(SEQ ID NO: 11)
gcttctcctgtcaccgacgatcGTTTTAGAGCTAGAAATAGCAAGTTAAAATAAGGCTAGTCCGT

TATCAACTTGAAAAAGTGGCACCGAGTCGGTG

>AtCCR1-target3
(SEQ ID NO: 12)
gacttctgcaaaaacaccaGTTTTAGAGCTAGAAATAGCAAGTTAAAATAAGGCTAGTCCGTTA

TCAACTTGAAAAAGTGGCACCGAGTCGGTG

---
Myb
---

>AtMyb63-target1
(SEQ ID NO: 13)
ggaagagttgtcgtctaaggGTTTTAGAGCTAGAAATAGCAAGTTAAAATAAGGCTAGTCCGTT

ATCAACTTGAAAAAGTGGCACCGAGTCGGTG

>AtMyb63-target2
(SEQ ID NO: 14)
gtggcaacttcacttcagaggGTTTTAGAGCTAGAAATAGCAAGTTAAAATAAGGCTAGTCCGTT

ATCAACTTGAAAAAGTGGCACCGAGTCGGTG

>AtMyb63-target3
(SEQ ID NO: 15)
gataacgagatcaagaatgtgGTTTTAGAGCTAGAAATAGCAAGTTAAAATAAGGCTAGTCCGT

TATCAACTTGAAAAAGTGGCACCGAGTCGGTG

---
IRX7
---

>AtIRX7-target1
(SEQ ID NO: 16)
gacagggacaaagaagaaatGTTTTAGAGCTAGAAATAGCAAGTTAAAATAAGGCTAGTCCGT

TATCAACTTGAAAAAGTGGCACCGAGTCGGTG

>AtIRX7-target2
(SEQ ID NO: 17)
gaagttgcaagagacatagacaGTTTTAGAGCTAGAAATAGCAAGTTAAAATAAGGCTAGTCCG

TTATCAACTTGAAAAAGTGGCACCGAGTCGGTG

>AtIRX7-target3
(SEQ ID NO: 18)
ggatgaagttccatcttgccaGTTTTAGAGCTAGAAATAGCAAGTTAAAATAAGGCTAGTCCGTT

ATCAACTTGAAAAAGTGGCACCGAGTCGGTG

---
IRX8
---

>AtIRX8-target1
(SEQ ID NO: 19)
gatggaacagagaacaagaaGTTTTAGAGCTAGAAATAGCAAGTTAAAATAAGGCTAGTCCGT

TATCAACTTGAAAAAGTGGCACCGAGTCGGTG

-continued

\>AtIRX8-target2

(SEQ ID NO: 20)
gaagctgagcttgtccctatgtGTTTTAGAGCTAGAAATAGCAAGTTAAAATAAGGCTAGTCCGTT

ATCAACTTGAAAAAGTGGCACCGAGTCGGTG

\>AtIRX8-target3

(SEQ ID NO: 21)
gacaatattcttgcagcttGTTTTAGAGCTAGAAATAGCAAGTTAAAATAAGGCTAGTCCGTTAT

CAACTTGAAAAAGTGGCACCGAGTCGGTG

ILLUSTRATIVE EXAMPLES OF PROMOTER SEQUENCES

Fiber promoter

\>pAtNST1

(SEQ ID NO: 22)
GTTTGTAGAGTTGGATCAGCATCCAGATTTAAACCCTTATTTTTGTTTTTGCCAAGCATCCAGA

CTTAATCCTATATTAGATACTGTATATGCATCTTGATGGAATATAGACTATATAGAAAGACCAA

AAATGGAAGAGTACGAATAAAAATGCATAATATACCTTGGAAATTATTCTTGGTTATTGTGAAA

CTTAAAACATTTCAACGAAGTCATATACTATTATTTAATCATTGATTTAAAATTGCTAATCAAA

TCACGTGTTGTTGTTATATATGGATAAAGAGTTAAACTATAACACAACTGAGAAAAAAATAAAG

TTATCAATTTTGTTAAGAATCAATGAAGGTTTCACAAGACTGGGAAGAAAAAAAAATAGATATA

TGGAGTACATAAAACATTAAAATTTTGCTAAATTTTACTTTTGAACTCTATTGATTCGGGTTGA

CATGATGATAATGTTACATTCGTACAATTTCACAATGAAAAAAACGAGTACTAAATATTGTCAA

TCAAACATATGAATGTACAAAAATCCATAAACTCTACCAAAATAGAATGAAGATTCTGAAATCA

AACCTACTTTTTCTTTTTAATTATAAATTCAACTATATTATAAATTTATTTATCACAAATAATA

GAGGAGTGAGAATATTTTAGACAACGCAAATTTCTTTTATTTAGTTCTTATACTTTATTTTTA

CCAAACGTTAATTAAAAAAATCACACATACATAATTTCTAAAAAAAATGTATTCTTCAAGTAAT

ATATCTTTCTGAGTACTAGTTTATCTATTTATCTCCGTATTTAATAATCAAAAGTTACGTTTAA

AATAGAAACAACTTTTATCAAACAAAATATATTAGAAAACGCATGGTACTGGCTACTGGAAAGA

ATCATGACCTGTAAATTTCTACAGTTTTCCCGTTTTATATAGTACTTAGAAACTTTGGATTTTC

ATAGCGCAACCAATAAACACATGGACTTAAGACACAAAAAAAGTTGGGTGCAATGTCATTAATC

AAACTAAAAAAATAATGATTAAAAGCATGGAATTCCGAAAACGCAACAAAATGATTCTGTGTTT

AGACAAATGCAGAAAGGCCTCTTAACTAATCTTAAATAAAGTCTTAGTTCCAACCACATAAACA

CTCCTTAGCTCCATTAATTTTGGTTTTCTTAATTACGTTTCTACACAAGTACACGTACTTACAC

ATACAATTCCACAGTCTAAATGATAAAACTATGTGGTTTTTGACGTCATCGTTACCTTTCTGTC

GTCTCACCTTTATATAGTGTCTCTAACAGAACGTAACAACCAAATGTTTAAAAAAATAAAACA

GCACCCCTTAATTAGGCTCATTCGTTTTGCACTAACCATACTACAAATCATCTCGAACGATCGA

GCAAAGATTTGAAAAATAAATAAACGTATAACTCTAGAGATTTTCATTAGCTAAGAAAGTGAA

ATCGATTGTTAATCCTATTTCAGACGGGACAGGAACACTCATTACCCAACTCTATCATCTCTCG

AACACCAAACTATATCTACCGTTTGGGGCATTATTTCCCACTTTCTTTCGAAGCAATTTCCCA

TATATAACATATACACATTATTACTAATATATTTTTATAAATTTTCGTCACATCCCAAAAAAAA

ACACTCTTTGTCACATCAACTAGTTTTTTTGTAACGATCAAACCTTTTCGTTTAAAAAAAAAAA

ACTTTTGTAGTGTAAACGTTTATTTATCGATGAAAAAAGCCACATCTTCCGGAGGGAAACTTTT

TAAGACACCCTATTTCGACTTTATTTTGTAAATACAGTGTGCATGTGCATATAAAGAGAGATAT

CATTTGTATAAATATCAAGAATTAGAAGAGAAAAAGAGAGAAGAAGACAATCTATTACTATTAC

GATGTGTGGGTTGTTAATTTGTTTAAAGGGAGCTTTTCTATAGAGATTTTTAAGGTCAAGGGTC

ATCGTTCGATGTGGGCTTGCTTCCTACAATCTAGTTGCCTTACGGGGCCTACTCTTTTTCTTTT

```
GATAACTACATCACCTTTTTTTCTCCGACAACTATATATCACTTTTTTTATGTTTTCCTTTTT
TTCTTCACAATAATTCTTTACTCGTTGCAAATGTAAAGATACACAAAGTTACTTATTTTGTTTA
CGATGGTTCTTAGTAGTTTAAAGAATTAATGAATAAGATAAACCTAAACTTTGAAAAGACTAAA
AAAAATGTATAACAACATACATTATACGTATTTGAAATAGTCCAAGTGATATTATGTCATTGAT
ATTAGCACAAATAATTACGATGCCTGATATTGTCACATTTGATGATTTTAAGTTCTTGTAAAAG
ATAAGTGTAACTAAATCACTATAGTGAGGCCCACGTTTTAATTTCTAAACTAATTACAATGACA
ATAAAATAGCAAAACTATTTAAAACTAGACGCCAAAAAAAATTGAAACTAATAATTGTGAAAAA
AGAACAAGAGAATAATAATCATTAATAATTGACAAGTGAAATTAATATATTGCTCTTGGAGGGT
TATATTTTAATTTTCAAACTAAATAATGAATACAAATGGAAAAGCTAATGATAAGAGTTGAATT
TTAATAATTAAGAAAAACAAAAAAAGGTGTACAAGGAGACACATGCGTTTTCCTCATGCATCTT
GTTTTTATACAACAATATATATATATATATTGAGTCATTCTCTGCTAGCTCTCTCATCTCCAAC
TTTCAGTATGATATATAGTTACAATTAAATAAACCTCACATGCTCTATTCTTGCTTGATTTTTG
AGTTAATCTTGAATCTCTTTG
>pAtNST2                                                    (SEQ ID NO: 23)
AACGGTGGCGTGATGGAGCTTCATCCTCCCATCTTCGCCGAATTCATCACCAACGAATTTCCCG
GCCATGTCATCCACGACTCTTTAAGCCTCCGCCACTCATCTCCACCGCTTCTCCACGGCGAAGA
ACTCTTTCCCGGTAACATCTACTACCTCCTTCCTCTTTCTTCTTCCGCAGCCGCGACCGCTCAA
CTGGATTCCTCCGACCAACTATCAACGCCGTACAGAATGTCTTTCGGGAAGACGCCGATAATGG
CGGCTTTGAGTGGCGGTGGTTGTGGAGTGTGGAAGGTGAGGCTTGTGATAAGTCCGGAGCAGTT
GGCGGAAATTCTTGCGGAGGATGTGGAAACGGAAGCGTTGGTGGAAAGTGTGAGGACGGTGGCG
AAGTGTGGCGGTTACGGCTGCGGCGGAGGAGTTCATTCGAGAGCGAATTCAGACCAGCTAAGCG
TTACGAGTAGCTTTAAAGGGAAATTGTGGTAAAATTTCGAATTATGAATAAACTACGTTTATGT
TTTAATCTGTTTCACGATTTAAGCATTTAAATTAGTATGTTGATTTCCGTATTCATTGAAGACT
TGGAACGATTATATAAGTTTATCAACGTAGATATATTTGAAATATCATTGTTATCTCTCATGAA
ACAATTAATTTATGAAGTCGTAGACTCGTAGTTAGAGATTATTTAATCTTCCCTATTCAATGCC
AAAAGTCTAGAAGAGCAAACAAAAGGGAGAAACTCTTTTATTTCAGGCCCAATGACACAAAGC
TGGCCAGAAACAGTTTAAGATTAGGCTAAAGTTATAAGTCCGACAAGCACGAGTGCTAATATAT
ATAGTTATATGACGTCTCACCATTAAGGGTTTAATAAATTTTGAAACACCTCAAATTAAGATTG
CTTCCCATGCAAACTTCCTTCATCTTCTAGAAAAATTACGATTTGTAATACTTCAATTATATCA
TTTTAGTTTTTTGTCACTAATTATCATCAATTTATCATAGCTCCGTGCCGCAACAACGTTCGTT
TTAATCAGATTATATATTACTCTGCTATAAACTCAGAACCATGTTAGAAAAATGAAAAAGACAT
TTCAGAATATTCATTAACTCAAAATTTTAATCTCATGATTTAATTTTTTATTAACAATGTTATC
CTATAGCACATGGCAAATTTGAACGGCCCTTGCGTATTAATCTATTATAATCTCAAAACCATGT
GTAAGAAAAGGAAATTCAGAAAATAACCTTTTGTAAATAGGCCCCCACAAAATCTACAACATA
CGTAGATACCTCCTCGCTTACAGTTGTAAACAACTGTTCATCTAGATTCATGCCGTCATTCAAG
TTTAAATTAATACAATAATTTAAAATTTAATTTGGATGAATCGAATCCACCGTCGTTTCCTGA
ATACCAGATAGGTTAACTTTATGATTAGTTCGAGTGAACCACATGCACAATATTCGAATCTTAG
ACATTCGTTGCAATGTTAACTTCACATATATTTGATAAACGCTTCTTGAATCAGATCTTAATCT
CTTTCTTTCTCTCCATCTTCTAAGGAGGTTGTGGATTATCATGTAGTATATCATTATCTTCGCA
TCACCTTCAACAAGAACAAGCTACGAGCTTTAAAGTCGTATTTAACACAATAATGTATAAAGTC
```

-continued

TTTCTTCATCACATCACATACATTTTTTGTTGCCATCACCCTTCATTCACTTTTTTGTTAACA

CTATTCGTTTCTATATAAAATAAAAATAAAATGAGGAATGTCTTGTCCATAGAGATTTTTAAGG

TCGAGGGTCATCGGAGCGATGTGGGCTTGCTTCCTACATTATAGTTGATATGTGGATCCCGCGT

GGACCATATTTTTACCCAATAGCTACGTGCATGGTCCCACCGCTCTCTCTCACGCACTATTCCG

AAATTGCCATAAACAATTTCACCGGACAAAAAGAGCAAATAATTTCGATGTTTAATAAAGAGAC

CATTAGTATATTTGACCCAAAAAAAAATAAAAAAAAAAGAGAGACATTACTATAACTTTTATTA

GATGAAATATTGCAACATTGTATTTATAACGGATCTAATTTACTGAATCATATTTTTTTCTTT

GTTAAAGAGATACTGAATCATGCAGAAAAATAGATAGATTTTTAAATACTAGGTGAACTCATGA

CGAATCAACCATTACGAGAGATTTCTGGATAAAAGCAAAAACAAAACAAAACTAACATGCTAAT

CTAGGCAATTAGTAGAGCGAAAAGTCGGCAAAACCAAAGGCCGAAGAAGCTTGATCGATATACT

TTTTTTTTTTTGTTTTGGCTGGATATACTTGGTATGAACTAAGAATTAAGTAAAAACTCATAGG

GAGTAATTTTTCGAGAAGTGCATTCACTATGAGTATAAAACAGACATTTTCAAATTATTAAAAC

AAGCTCTTAGAGGCTCATATGTTTAATTGTAAGTGGCGGCTCATGCGAACTTATAATGAAAACA

TCAAATATTCGGAAAAATAATACTCCACTGTTAAAAAGAAAACTTAACAAAGGAATTAAAAATA

TGAGAGCAAAAGAACACATGCATTTTCTCATGCATGTACTATTATTTATTTTTTTGCAGAGTTG

ATGTAAAAAATATACACATATATATAGACATACTTTGGTTAGTTATAAACTCGTTCTATTTTCT

TCTCCTTTTTCTATCTTTAGCA

>pAtNST3

(SEQ ID NO: 24)

ATTCTACACATTCACAAAGTTTACTACACTATATATAATTTACCCAACAAACACTTATTTTACT

GCATTATTCAGTATATTATCTTACCTATAAATGTGTATCATCATCATCAATAACGCGATTATTT

GTGCTGAAGGATTATATATTCAAAATGATCTAGTTATATATGTCACATGATTGCCGTTAACAAG

ACACATTTGAAGAAGCTAAGCAAGAAAAACGGACACTTTTGCGACTTGTTACATAATTTAACTT

ATAGGTCAAAAGAATTTGATTAGTCATTGCAACTACGTGTGGATGTCACTTTCTATTCAACCAA

AACTCACAATATTATATGATCTAGTTTTGTCGTATTACTGATTTGTATTATAAAATGTTATTTA

ATTTGAATTCTACGTAGATATTGCTCATGCATGATAGTATGTATCTAAACTATTCAAATAACTA

ACTACGTGGATATTTTATAATCCAAGTAAAAAGCAGAAAGTGGGTAACTACGTCAGTATGACTA

TACTTTTATCGGAATTGCTTGACATCCAAACTTTTGCTATGCTTCACCAACCAATGCAGTTTCA

CTTAATTATTAACTATTGACTATGTCTTATTAAGTTAGCACTAATTCGTTAATCATTCAAAACG

TTATTTGATTGAATTACATATTACACTCTCTTTCTGCATCACCACTCACACCATATGCAACTAT

AACCAACTCATCACATTCAAATGTATTAATTGGATTTTGGTGCGAGATTAAAAATTGAAAGGAA

ACAAAATATGATAATGGGATAAAATCTTGAACGGAAACTCAAACTAATCCTCATAAGGTATAAC

AAAATAACAATTTAAGCTAAGCACAACAACATACAAGTTCGACCTTTTCCTTTGATGATCCAGC

CCAACAGTTCTCTTATATCTCAAACCATTCGACCATTTGAGCCAAACTAGCTAAACCTGCAGGA

ATCAAAACCAACAAAGATTCAGATTAGCTAAACCGGTTTCATCCCTTTGTCACATGACTCACAT

CCGTCTTCTACATAACGATTTCTAATGATGTGAGCTCTTAACTTGCTCCAGCAAGATCATCAAC

TTTGGAGCACCTTCAATGATTTAGTTAACATGTTAGATAAATTAAATATTCTTGTTTCAATATA

TATCAACTTTAGTGTAAAAGCCTTAACATTCTCTTGAATATTTAATTTATTTCTCCTTATTTCG

ATTTAATGACAAATGTGAATTAATTTTTGTGATATTTTTGTTCGAAATTAGTTTTCAGTTAATA

ACATACATGTGAGCATGGGACACACATGATTTAACAAAAGGGAATGACGAAATGATATATCAAA

ATATTAGTATGGGAACAAATTACGAGGTGAAACTTCACACTCAACTCAATTAAAACTAGAATAA

AGAAATGGAAAAAGTGAAAGAATGAGAGGTCAAATGTGGTTAATCATTATGTGGTATTAGTTAA

-continued

```
TCCATCAATTGTGTACCCAAAAGCATGATTAAGCATAGAATTTAGAGAAACAAAACATCATTAT

TAATGTTGAAACACAAAGATCCCATCAACAGACAAATGATAAGTACAGTGCATGTAGGGTAACA

ACTTTTATGTACATGTTATATACTTATATTATATAATAAGAAAACGATTAAAGTGTCATTGCTC

CAGCCTCTATTTGTAAATCATATTATATCAGTATGCTTAATTCCAATAATTAAGTCCATAACTA

AAATATATACACATATATGTATGTTAAATGGTTGAATATATACATATATTTTCATAAACAAATA

TTGCTAATTAATTCAGTTATTTGTGTACATAATCCAACTATCACCTTTTTAGCTGGAAGTGGAT

ATTCCAACATGTCAGTCTGTCACTCCCACATTCATACTCTCTATTCTTTTTAGCTATTTCAATA

TCTACGGTTAAATATTAATGGCTATATAGCCTTACCCTTCATTTTAGTTTTTTTTGGTATTCG

CATAACCATCGAATACTCAAACTTACTATGTAAGATGGTCTGAATAACTATTTCCGATTTAAGA

TGAATAGCTAGATTGAAATATACATGCACTAATTGGACATGCACTAAAGGCAGAGGTGAATTAA

ATGATGAAATGAAGATGAAGTGTCACACTTGTGCAAAAGCATGTCCCCTGCTCTTCTCCGCTT

GTTTCAATTTCTTTGACTTTCATCACGTTTTTGTCACTTAAATACACCAAAAAATATAGTACAA

TTAAACATCGAAAATCGTCCAAAAAGAAGAAAAAAAATCATGGAAAGTTCTTTCGTTAATGTTA

CACACATTATCTTGATTAGGTGACACCAGATATTAGAATAAAAATGATAGATTATGAAAAGAAA

AAAAAAATTGATGTATTTTTAGGATACATCGAAAGGAATGAACATACCAAAAACATGGGAAAAA

ATAGATAACTAATTAACATGGTAGAATGTAGATGACGTAGATCATGAAACGAGTGTGTGATATA

TTAATGAAAATTATTTTAATATACGTAGCTATATTAGAAAATAATTTACATTTATTTTCTTCTA

AACAAATCTATACTTTATATTTACATACATTAGTAAAGACCAAAACACATGGAATTCAAATTCT

GCAATAAGTAATTGCAAGAAAACACAAAGATTAATCCCCCACTAAACCCGTTTATTTACGTTAG

TATTTTTCCGTTTTATACATTACACATGACATGACATTACACGTCAAAAGAAATATGTCTTACG

TCAGAACTTACGTATGATCAAACTCGATTTAAACATAGAAACATCTGTTTACTAAATTATACTA

ATTTCATAAAGACACTTTAATGCATGAACTTCTTTGTTTAAATAACAATTTCCCCCTTTTGGGG

GCTATGTCTCGTCGAGTCCTACCACCATTATAAATTATCTCATCGTTTGCTTTCTTTTTTTAA

GTTGTAACCATTTCCACTCGTAATCATACAACTTCTCTACTCTTCTAGAGCAAAAACCCAAAAA

TATATTGCTATCTTCGTTA
```

Example of ribosomal RNA promoters

>pAtU6-26pG
                                                                      SEQ ID NO: 25)

```
AGCTTTCGTTGAACAACGGAAACTCGACTTGCCTTCCGCACAATACATCATTTCTTCTTAGCTT

TTTTTCTTCTTCTTCGTTCATACAGTTTTTTTTGTTTATCAGCTTACATTTTCTTGAACCGTA

GCTTTCGTTTTCTTCTTTTTAACTTTCCATTCGGAGTTTTTGTATCTTGTTTCATAGTTTGTCC

CAGGATTAGAATGATTAGGCATCGAACCTTCAAGAATTTGATTGAATAAAACATCTTCATTCTT

AAGATATGAAGATAATCTTCAAAAGGCCCCTGGGAATCTGAAAGAAGAGAAGCAGGCCCATTTA

TATGGGAAAGAACAATAGTATTTCTTATATAGGCCCCATTTAAGTTGAAAACAATCTTCAAAAGT

CCCACATCGCTTAGATAAGAAAACGAAGCTGAGTTTATATACAGCTAGAGTCGAAGTAGTGATT g
```

>pOsU6pG
                                                                       (SEQ ID NO: 26)

```
GGTTTGTGAAAGTTGAATTACGGCATAGCCGAAGGAATAACAGAATCGTTTCACACTTTCGTAA

CAAAGGTCTTCTTATCATGTTTCAGACGATGGAGGCAAGGCTGATCAAAGTGATCAAGCACATA

AACGCATTTTTTTACCATGTTTCACTCCATAAGCGTCTGAGATTATCACAAGTCACGTCTAGTA

GTTTGATGGTACACTAGTGACAATCAGTTCGTGCAGACAGAGCTCATACTTGACTACTTGAGCG
```

-continued

ATTACAGGCGAAAGTGTGAAACGCATGTGATGTGGGCTGGGAGGAGGAGAATATATACTAATGG

GCCGTATCCTGATTTGGGCTGCGTCGGAAGGTGCAGCCCACGCGCGCCGTACCGCGCGGGTGGC

GCTGCTACCCACTTTAGTCCGTTGGATGGGGATCCGATGGTTTGCGCGGTGGCGTTGCGGGGA

TGTTTAGTACCACATCGGAAACCGAAAGACGATGGAACCAGCTTATAAACCCGCGCGCTGTAGT

CAGCTTg

>pAt7SL-1pG (SEQ ID NO: 27)
CAATGACACTCACAAATCTAGTAGTGGCTGAATTGGCTCGATGTTAAATGCAAACTAACGAAGT

CTCATCAAATAATAACTCTTCTTCTTGCATTTGCTTTCTTTGCCCCTTTCTCTCTTCTTCCATC

TCAAATCTGTCTCTTCAATATTACTATTGGGCTTTTGGTTAGTCTATAATGGGACTCAAAATAA

GGCTTTGGCCCACATCATAAAAGATAAATTCACAAATCAAAACTAATTTTCAGAGTCTTTTGTC

CCACATCGGTCAATCTACTCGTTTTGTGTTTGTTTATATATTACACGAAACGATGTATTCAACg

>pAt7SL-2pG (SEQ ID NO: 28)
ATGTTGTTACCAGAAAGTAAATAAATGTTCAATCTCTGATGTTCTCAAGTAAGTGAGTCTTATT

GGGAATAATTTAAACTCATGTTCTTCTTGCATTTGATTTCTTTGCCACTCTCTTCTTCTATCTC

AAATCTGTCTATACTATCTCACTACTGGGCTTTTTATTAGTCTACAATGGGACTCAAAATAAGG

CTTTGGCCAACATCAAAAAGATAAGTCACAAACCAAAACTAAATTCAGAGTCTTTTCTCCCACA

TCGGTCACTGTACTCATTTTGTGTTTGTTTATATATTACACGAACCGATCTTTGTTACg

>pAtU3B-1pA (SEQ ID NO: 29)
TTCTTATGGCTCAGCCTGTGATGGATAACTGAATCAAACAAATGGCGTCTGGGTTTAAGAAGAT

CTGTTTTGGCTATGTTGGACGAAACAAGTGAACTTTTAGGATCAACTTCCGTTTATATACGGAG

CTTATATCGAGCAATAAGATAAGTGGGCTTTTTATGTAATTTAATGGGCTATCGTCCATATATT

CACTAATACCCATGCCCAGTACCCATGTATGCGTTTCATATAAGCTCCTAATTTCTCCCACATC

GCTCAAATCTAAACAAATCTTGTTGTATATATAACACTGAGGGAGCACCATTGGTCa

>pAtU3B-2pA (SEQ ID NO: 30)
TTTACTTTAAATTTTTTCTTATGCAGCCTGTGATGGATAACTGAATCAAACAAATGGCGTCTGG

GTTTAAGAAGATCTGTTTTGGCTATGTTGGACGAAACAAGTGAACTTTTAGGATCAACTTCAGT

TTATATATGGAGCTTATATCGAGCAATAAGATAAGTGGGCTTTTTATGTAATTTAATGGGCTAT

CGTCCATAGATTCACTAATACCCATGCCCAGTACCCATGTATGCGTTTCATATAAGCTCCTAAT

TTCTCCCACATCGCTCAAATCTAAACAAATCTTGTTGTATATATAACACTGAGGGAGCAACATT

GGTCa

>single-C4H-locus-target (figure Bioediting
constructs A)

(SEQ ID NO: 31)
GTACCGAGCTCGGATCCACTAGTAACGGCCGCCAGTGTGCTGGAATTCAGGCGGCCGCGTTTGT

AGAGTTGGATCAGCATCCAGATTTAAACCCTTATTTTTGTTTTTGCCAAGCATCCAGACTTAAT

CCTATATTAGATACTGTATATGCATCTTGATGGAATATAGACTATATAGAAAGACCAAAAATGG

AAGAGTACGAATAAAAATGCATAATATACCTTGGAAATTATTCTTGGTTATTGTGAAACTTAAA

ACATTTCAACGAAGTCATATACTATTATTTAATCATTGATTTAAAATTGCTAATCAAATCACGT

GTTGTTGTTATATATGGATAAAGAGTTAAACTATAACACAACTGAGAAAAAAATAAAGTTATCA

ATTTTGTTAAGAATCAATGAAGGTTTCACAAGACTGGGAAGAAAAAAAAATAGATATATGGAGT

ACATAAAACATTAAAATTTGCTAAATTTTACTTTTGAACTCTATTGATTCGGGTTGACATGAT

GATAATGTTACATTCGTACAATTTCACAATGAAAAAAACGAGTACTAAATATTGTCAATCAAAC

-continued

```
ATATGAATGTACAAAAATCCATAAACTCTACCAAAATAGAATGAAGATTCTGAAATCAAACCTA

CTTTTTCTTTTTAATTATAAATTCAACTATATTATAAATTTATTTATCACAAATAATAGAGGAG

TGAGAATATTTTAGACAACGCAAATTTCTTTTATTTAGTTCTTATACTTTATTTTTTACCAAAC

GTTAATTAAAAAAATCACACATACATAATTTCTAAAAAAAATGTATTCTTCAAGTAATATATCT

TTCTGAGTACTAGTTTATCTATTTATCTCCGTATTTAATAATCAAAAGTTACGTTTAAAATAGA

AACAACTTTTATCAAACAAAATATATTAGAAAACGCATGGTACTGGCTACTGGAAAGAATCATG

ACCTGTAAATTTCTACAGTTTTCCCGTTTTATATAGTACTTAGAAACTTTGGATTTTCATAGCG

CAACCAATAAACACATGGACTTAAGACACAAAAAAAGTTGGGTGCAATGTCATTAATCAAACTA

AAAAAATAATGATTAAAAGCATGGAATTCCGAAAACGCAACAAAATGATTCTGTGTTTAGACAA

ATGCAGAAAGGCCTCTTAACTAATCTTAAATAAAGTCTTAGTTCCAACCACATAAACACTCCTT

AGCTCCATTAATTTTGGTTTTCTTAATTACGTTTCTACACAAGTACACGTACTTACACATACAA

TTCCACAGTCTAAATGATAAAACTATGTGGTTTTTGACGTCATCGTTACCTTTCTGTCGTCTCA

CCTTTATATAGTGTCTCTAACAGAACGTAACAACCAAATGTTTAAAAAAATAAAAACAGCACCC

CTTAATTAGGCTCATTCGTTTTGCACTAACCATACTACAAATCATCTCGAACGATCGAGCAAAG

ATTTGAAAAATAAATAAACGTATAACTCTAGAGATTTTCATTAGCTAAGAAAAGTGAAATCGAT

TGTTAATCCTATTTCAGACGGGACAGGAACACTCATTACCCAACTCTATCATCTCTCGAACACC

AAACTATATCTACCGTTTGGGGCATTATTTCCCACTTTCTTTCGAAGACAATTTCCCATATATA

ACATATACACATTATTACTAATATATTTTATAAATTTTCGTCACATCCCAAAAAAAAACACTC

TTTGTCACATCAACTAGTTTTTTTGTAACGATCAAACCTTTTCGTTTAAAAAAAAAAAACTTTT

GTAGTGTAAACGTTTATTTATCGATGAAAAAAGCCACATCTTCCGGAGGGAAACTTTTTAAGAC

ACCCTATTTCGACTTTATTTTGTAAATACAGTGTGCATGTGCATATAAAGAGAGATATCATTTG

TATAAATATCAAGAATTAGAAGAGAAAAAGAGAGAAGAAGACAATCTATTACTATTACGATGTG

TGGGTTGTTAATTTGTTTAAAGGGAGCTTTTCTATAGAGATTTTTAAGGTCAAGGGTCATCGTT

CGATGTGGGCTTGCTTCCTACAATCTAGTTGCCTTACGGGGCCTACTCTTTTCTTTTGATAAC

TACATCACCTTTTTTTTCTCCGACAACTATATATCACTTTTTTTATGTTTTCCTTTTTTCTTC

ACAATAATTCTTTACTCGTTGCAAATGTAAAGATACACAAAGTTACTTATTTTGTTTACGATGG

TTCTTAGTAGTTTAAAGAATTAATGAATAAGATAAACCTAAACTTTGAAAAGACTAAAAAAAAT

GTATAACAACATACATTATACGTATTTGAAATAGTCCAAGTGATATTATGTCATTGATATTAGC

ACAAATAATTACGATGCCTGATATTGTCACATTTGATGATTTTAAGTTCTTGTAAAGATAAGT

GTAACTAAATCACTATAGTGAGGCCCACGTTTTAATTTCTAAACTAATTACAATGACAATAAAA

TAGCAAAACTATTTAAAACTAGACGCCAAAAAAAATTGAAACTAATAATTGTGAAAAAGAACA

AGAGAATAATAATCATTAATAATTGACAAGTGAAATTAATATATTGCTCTTGGAGGGTTATATT

TTAATTTTCAAACTAAATAATGAATACAAATGGAAAAGCTAATGATAAGAGTTGAATTTTAATA

ATTAAGAAAACAAAAAAAGGTGTACAAGGAGACACATGCGTTTTCCTCATGCATCTTGTTTTT

ATACAACAATATATATATATATATTGAGTCATTCTCTGCTAGCTCTCTCATCTCCAACTTTCAG

TATGATATATAGTTACAATTAAATAAACCTCACATGCTCTATTCTTGCTTGATTTTTGAGTTAA

TCTTGAATCTCTTTGCCTAGCCTGTTATCAACAAGTTTGTACAAAAAAGCAGGCTTCATGGATA

AGAAATACTCAATAGGTTTGGACATAGGAACTAACTCCGTTGGTTGGGCAGTGATAACAGACGA

ATATAAAGTGCCATCTAAAAAGTTCAAAGTTTTAGGTAATACAGATAGACATTCTATTAAGAAA

AATTTGATTGGTGCTTTGTTATTTGATTCCGGAGAAACCGCTGAGGCAACTAGATTGAAGAGGA

CTGCAAGAAGGAGATACACAAGGAGAAAGAATAGAATCTGTTATTTGCAAGAAATCTTTTCTAA
```

-continued

```
TGAGATGGCTAAAGTTGATGACTCTTTCTTTCATAGGCTTGAAGAGTCATTTTTGGTGGAAGAG

GATAAAAAGCATGAAAGACACCCAATCTTCGGTAATATAGTTGATGAAGTGGCTTATCATGAGA

AGTACCCTACCATCTATCACTTAAGAAAGAAATTGGTTGATTCTACTGACAAGGCAGATTTGAG

GTTAATATACCTTGCTTTGGCACATATGATAAAGTTTAGAGGTCACTTCTTAATCGAAGGAGAC

CTTAATCCAGATAACTCAGACGTTGATAAATTGTTTATTCAACTTGTGCAGACATACAACCAAT

TGTTCGAAGAGAATCCTATCAACGCTAGTGGTGTTGATGCTAAGGCAATACTTTCCGCAAGATT

GTCTAAGTCAAGGAGATTAGAAAATCTTATAGCTCAGTTGCCAGGAGAGAAAAGAATGGTTTA

TTCGGAAACCTTATCGCATTATCTCTTGGATTGACCCCTAATTTTAAATCAAACTTCGACTTGG

CTGAAGATGCAAAGTTACAACTTTCAAAGGATACTTACGATGACGATTTGGACAATCTTTTGGC

TCAGATTGGAGACCAATATGCAGATTTGTTTTTAGCTGCAAAGAACTTGAGTGATGCTATCCTT

CTTTCCGACATCCTTAGAGTTAACACTGAAATAACAAAGGCTCCACTTAGTGCATCCATGATCA

AAAGATACGATGAACATCACCAAGACTTGACTTTGTTAAAAGCATTGGTTAGACAACAGCTTCC

TGAAAAGTACAAGGAGATCTTTTTCGATCAGTCTAAGAACGGTTATGCTGGATACATAGATGGT

GGAGCATCACAAGAAGAGTTCTACAAATTCATCAAGCCAATCTTGGAAAAGATGGATGGTACAG

AAGAGCTTTTGGTTAAGTTAAACAGAGAAGATTTGCTTAGAAAACAGAGGACCTTCGACAATGG

TTCTATTCCACATCAAATCCACTTGGGAGAATTACATGCTATTCTTAGGAGACAAGAGGATTTT

TATCCTTTCTTGAAGGACAATAGAGAAAAGATTGAGAAGATCCTTACTTTTAGAATTCCATACT

ACGTTGGTCCTTTGGCTAGAGGAAACAGTAGGTTCGCATGGATGACCAGAAAGTCCGAAGAGAC

CATAACTCCATGGAATTTTGAAGAGGTTGTGGATAAAGGTGCTTCTGCACAATCTTTTATTGAA

AGAATGACAAACTTCGATAAGAATTTGCCAAACGAAAAGGTTCTTCCTAAGCATTCTTTGCTTT

ACGAATACTTCACCGTGTACAACGAGCTTACTAAGGTTAAGTACGTGACAGAGGGTATGAGAAA

ACCTGCTTTTCTTTCAGGAGAGCAGAAAAAGGCAATTGTTGATCTTTTGTTCAAGACAAACAGA

AAGGTTACCGTGAAGCAATTGAAGGAAGATTACTTCAAAAAGATAGAGTGCTTCGATAGTGTTG

AAATTTCCGGTGTGGAGGATAGATTCAATGCTTCTTTGGGAACTTACCATGATTTGCTTAAGAT

TATCAAAGACAAGGATTTTCTTGATAATGAAGAGAACGAAGACATATTGGAGGATATTGTTCTT

ACATTGACCTTATTCGAAGATAGAGAGATGATTGAAGAGAGGCTTAAGACTTACGCTCACTTGT

TTGACGATAAAGTGATGAAGCAATTGAAAAGGAGAAGGTATACAGGTTGGGGAAGATTGTCTAG

GAAATTGATTAATGGTATTAGAGATAAGCAGTCTGGAAAAACTATACTTGATTTCTTGAAGTCA

GACGGTTTCGCTAACAGAAACTTCATGCAACTTATCCATGACGATAGTCTTACTTTTAAAGAAG

ATATCCAAAAGGCTCAGGTTTCTGGTCAGGGAGATTCATTGCATGAACACATTGCTAATTTGGC

AGGTTCTCCAGCAATCAAAAAGGGAATATTACAAACTGTTAAGGTTGTGGATGAACTTGTTAAA

GTTATGGGTAGACACAAACCTGAGAATATAGTGATTGAAATGGCTAGGGAGAACCAAACTACAC

AGAAGGGACAAAAGAATTCTAGAGAAAGGATGAAGAGAATTGAAGAGGGTATCAAAGAGCTTGG

TTCTCAAATTTTGAAGGAACATCCAGTTGAGAATACCCAACTTCAGAACGAAAAACTTTACTTG

TACTACCTTCAGAACGGTAGAGACATGTATGTGGATCAAGAATTAGACATCAATAGGCTTTCAG

ACTATGATGTTGACCACATAGTGCCTCAATCTTTCTTGAAGGACGATTCAATTGATAATAAGGT

TCTTACTAGAAGTGATAAGAATAGGGGAAAATCCGACAACGTGCCTAGTGAGGAGGTGGTTAAA

AAGATGAAAAATTATTGGAGACAGTTATTGAACGCAAAGCTTATTACACAGAGGAAGTTCGACA

ATTTGACTAAGGCTGAGAGGGGAGGTTTATCTGAGTTGGACAAGGCTGGATTCATTAAGAGACA

ACTTGTTGAAACCAGACAAATAACTAAGCATGTGGCTCAGATCCTTGATTCAAGAATGAACACC
```

-continued

```
AAGTACGATGAAAACGACAAGTTGATCAGAGAGGTTAAAGTGATTACTCTTAAGAGTAAGTTGG

TTTCCGATTTCAGAAAGGACTTCCAATTCTACAAAGTGAGGGAAATTAATAACTATCATCACGC

TCACGATGCATACTTGAATGCTGTTGTGGGTACTGCATTGATCAAAAAGTACCCAAAGTTAGAA

TCTGAGTTCGTTTATGGAGATTACAAGGTTTACGACGTGAGAAAGATGATTGCTAAGTCAGAAC

AGGAGATTGGTAAAGCTACAGCAAAGTACTTTTTCTATAGTAACATCATGAACTTTTTCAAGAC

TGAAATCACATTGGCTAACGGAGAGATCAGAAAAAGGCCTTTAATAGAAACAAACGGTGAAACC

GGAGAGATTGTTTGGGATAAGGGAAGAGACTTTGCAACTGTTAGGAAGGTGTTGTCCATGCCAC

AAGTTAATATCGTGAAAAAGACTGAAGTTCAGACAGGTGGATTCAGTAAGGAGTCCATACTTCC

TAAAAGAAACAGTGATAAGTTGATTGCTAGGAAAAAGGATTGGGACCCAAAGAAATATGGTGGA

TTTGATAGTCCTACAGTTGCTTACTCCGTGCTTGTTGTGGCAAAGGTTGAAAAGGGTAAATCTA

AAAAGTTGAAGTCAGTGAAGGAGTTGTTAGGAATTACCATCATGGAAAGATCTTCATTTGAGAA

AAATCCAATTGATTTCTTAGAAGCTAAGGGTTACAAGGAGGTTAAAAAGGACTTAATTATCAAA

CTTCCTAAGTACAGTTTGTTCGAATTAGAGAACGGAAGAAAAAGGATGTTAGCTTCCGCAGGTG

AACTTCAAAAGGGAAATGAGCTTGCTTTGCCATCTAAGTACGTTAACTTCTTATATCTTGCATC

TCATTACGAAAAATTGAAGGGTTCACCTGAAGATAATGAGCAAAAGCAGCTTTTCGTTGAACAA

CATAAGCACTATCTTGACGAAATCATAGAGCAGATATCTGAATTCTCAAAGAGAGTTATCCTTG

CTGATGCAAATTTGGACAAAGTGTTATCAGCTTACAACAAACATAGAGATAAGCCAATTAGGGA

ACAAGCAGAGAATATCATACACCTTTTTACCTTGACTAACTTAGGAGCTCCTGCTGCTTTTAAA

TACTTCGATACTACAATCGACAGAAAGAGGTACACATCTACCAAAGAAGTTCTTGATGCAACAT

TGATACACCAGAGTATCACAGGACTTTATGAGACCAGAATAGACCTTTCCCAGTTAGGAGGAGA

TGGATCCACTAGTGGTCCAAAGAAAAAGAGAAAAGTGGCAGCAGCAGCTCCTAAAAAGAAAAGA

AAGGTTGGTGGCAGCAGCGACCCAGCATTCCTTTACAAAGTTGTCTGAGGATCCCTAACTAGGA

TGAGCTAAGCTAGCTATATCATCAATTTATGTATTACACATAATATCGCACTCAGTCTTTCATC

TACGGCAATGTACCAGCTGATATAATCAGTTATTGAAATATTTCTGAATTTAAACTTGCATCAA

TAAATTTATGTTTTTGCTTGGACTATAATACCTGACTTGTTATTTTATCAATAAATATTTAAAC

TATATTTCTTTCAAGATGGGAATTAACATCTACAAATTGCCTTTTCTTATCGACCATGTACCCT

AGGTACCAAGCTTCTCGAGAGCTTTCGTTGAACAACGGAAACTCGACTTGCCTTCCGCACAATA

CATCATTTCTTCTTAGCTTTTTTTCTTCTTCTTCGTTCATACAGTTTTTTTTTGTTTATCAGCT

TACATTTTCTTGAACCGTAGCTTTCGTTTTCTTCTTTTTAACTTTCCATTCGGAGTTTTTGTAT

CTTGTTTCATAGTTTGTCCCAGGATTAGAATGATTAGGCATCGAACCTTCAAGAATTTGATTGA

ATAAAACATCTTCATTCTTAAGATATGAAGATAATCTTCAAAAGGCCCCTGGGAATCTGAAAGA

AGAGAAGCAGGCCCATTTATATGGGAAAGAACAATAGTATTTCTTATATAGGCCCATTTAAGTT

GAAAACAATCTTCAAAAGTCCCACATCGCTTAGATAAGAAAACGAAGCTGAGTTTATATACAGC

TAGAGTCGAAGTAGTGATTGTCGATTACGCTAAGAAATTGTTTTAGAGCTAGAAATAGCAAGTT

AAAATAAGGCTAGTCCGTTATCAACTTGAAAAAGTGGCACCGAGTCGGTGCCTAGGTTCAAACA

TTTGGCAATAAAGTTTCTTAAGATTGAATCCTGTTGCCGGTCTTGCGATGATTATCATATAATT

TCTGTTGAATTACGTTAAGCATGTAATAATTAACATGTAATGCATGACGTTATTTATGAGATGG

GTTTTTATGATTAGAGTCCCGCAATTATACATTTAATACGCGCACGTGCTCGAGGACCCAGCTT

TCTTGTACAAAGTGGT
```

>Dual-C4H-loci-target (figure Bioediting
constructs B)
(SEQ ID NO: 32)
GTACCGAGCTCGGATCCACTAGTAACGGCCGCCAGTGTGCTGGAATTCAGGCGGCCGCGTTTGT

AGAGTTGGATCAGCATCCAGATTTAAACCCTTATTTTTGTTTTTGCCAAGCATCCAGACTTAAT

CCTATATTAGATACTGTATATGCATCTTGATGGAATATAGACTATATAGAAAGACCAAAAATGG

AAGAGTACGAATAAAAATGCATAATATACCTTGGAAATTATTCTTGGTTATTGTGAAACTTAAA

ACATTTCAACGAAGTCATATACTATTATTTAATCATTGATTTAAAATTGCTAATCAAATCACGT

GTTGTTGTTATATATGGATAAAGAGTTAAACTATAACACAACTGAGAAAAAAATAAAGTTATCA

ATTTTGTTAAGAATCAATGAAGGTTTCACAAGACTGGGAAGAAAAAAAAATAGATATATGGAGT

ACATAAAACATTAAAATTTTGCTAAATTTTACTTTTGAACTCTATTGATTCGGGTTGACATGAT

GATAATGTTACATTCGTACAATTTCACAATGAAAAAAACGAGTACTAAATATTGTCAATCAAAC

ATATGAATGTACAAAAATCCATAAACTCTACCAAAATAGAATGAAGATTCTGAAATCAAACCTA

CTTTTTCTTTTAATTATAAATTCAACTATATTATAAATTTATTTATCACAAATAATAGAGGAG

TGAGAATATTTTAGACAACGCAAATTTCTTTTATTTAGTTCTTATACTTTATTTTTTACCAAAC

GTTAATTAAAAAAATCACACATACATAATTTCTAAAAAAAATGTATTCTTCAAGTAATATATCT

TTCTGAGTACTAGTTTATCTATTTATCTCCGTATTTAATAATCAAAAGTTACGTTTAAAATAGA

AACAACTTTTATCAAACAAAATATATTAGAAAACGCATGGTACTGGCTACTGGAAAGAATCATG

ACCTGTAAATTTCTACAGTTTTCCCGTTTTATATAGTACTTAGAAACTTTGGATTTTCATAGCG

CAACCAATAAACACATGGACTTAAGACACAAAAAAAGTTGGGTGCAATGTCATTAATCAAACTA

AAAAAATAATGATTAAAAGCATGGAATTCCGAAAACGCAACAAAATGATTCTGTGTTTAGACAA

ATGCAGAAAGGCCTCTTAACTAATCTTAAATAAAGTCTTAGTTCCAACCACATAAACACTCCTT

AGCTCCATTAATTTTGGTTTTCTTAATTACGTTTCTACACAAGTACACGTACTTACACATACAA

TTCCACAGTCTAAATGATAAAACTATGTGGTTTTTGACGTCATCGTTACCTTTCTGTCGTCTCA

CCTTTATATAGTGTCTCTAACAGAACGTAACAACCAAATGTTTAAAAAAATAAAAACAGCACCC

CTTAATTAGGCTCATTCGTTTTGCACTAACCATACTACAAATCATCTCGAACGATCGAGCAAAG

ATTTGAAAAATAAATAAACGTATAACTCTAGAGATTTTCATTAGCTAAGAAAAGTGAAATCGAT

TGTTAATCCTATTTCAGACGGGACAGGAACACTCATTACCCAACTCTATCATCTCTCGAACACC

AAACTATATCTACCGTTTGGGGCATTATTTCCCACTTTCTTTCGAAGACAATTTCCCATATATA

ACATATACACATTATTACTAATATATTTTTATAAATTTTCGTCACATCCCAAAAAAAAACACTC

TTTGTCACATCAACTAGTTTTTTTGTAACGATCAAACCTTTTCGTTTAAAAAAAAAAACTTTT

GTAGTGTAAACGTTTATTTATCGATGAAAAAAGCCACATCTTCCGGAGGGAAACTTTTTAAGAC

ACCCTATTTCGACTTTATTTTGTAAATACAGTGTGCATGTGCATATAAAGAGAGATATCATTTG

TATAAATATCAAGAATTAGAAGAGAAAAAGAGAGAAGAAGACAATCTATTACTATTACGATGTG

TGGGTTGTTAATTTGTTTAAAGGGAGCTTTTCTATAGAGATTTTAAGGTCAAGGGTCATCGTT

CGATGTGGGCTTGCTTCCTACAATCTAGTTGCCTTACGGGGCCTACTCTTTTTCTTTTGATAAC

TACATCACCTTTTTTTTCTCCGACAACTATATATCACTTTTTTTATGTTTTCCTTTTTTTCTTC

ACAATAATTCTTTACTCGTTGCAAATGTAAAGATACACAAAGTTACTTATTTTGTTTACGATGG

TTCTTAGTAGTTTAAAGAATTAATGAATAAGATAAACCTAAACTTTGAAAAGACTAAAAAAAAT

GTATAACAACATACATTATACGTATTTGAAATAGTCCAAGTGATATTATGTCATTGATATTAGC

ACAAATAATTACGATGCCTGATATTGTCACATTTGATGATTTTAAGTTCTTGTAAAAGATAAGT

GTAACTAAATCACTATAGTGAGGCCCACGTTTTAATTTCTAAACTAATTACAATGACAATAAAA

-continued

```
TAGCAAAACTATTTAAAACTAGACGCCAAAAAAAATTGAAACTAATAATTGTGAAAAAAGAACA

AGAGAATAATAATCATTAATAATTGACAAGTGAAATTAATATATTGCTCTTGGAGGGTTATATT

TTAATTTTCAAACTAAATAATGAATACAAATGGAAAAGCTAATGATAAGAGTTGAATTTTAATA

ATTAAGAAAAACAAAAAAAGGTGTACAAGGAGACACATGCGTTTTCCTCATGCATCTTGTTTTT

ATACAACAATATATATATATATATTGAGTCATTCTCTGCTAGCTCTCTCATCTCCAACTTTCAG

TATGATATATAGTTACAATTAAATAAACCTCACATGCTCTATTCTTGCTTGATTTTTGAGTTAA

TCTTGAATCTCTTTGCCTAGCCTGTTATCAACAAGTTTGTACAAAAAAGCAGGCTTCATGGATA

AGAAATACTCAATAGGTTTGGACATAGGAACTAACTCCGTTGGTTGGGCAGTGATAACAGACGA

ATATAAAGTGCCATCTAAAAAGTTCAAAGTTTTAGGTAATACAGATAGACATTCTATTAAGAAA

AATTTGATTGGTGCTTTGTTATTTGATTCCGGAGAAACCGCTGAGGCAACTAGATTGAAGAGGA

CTGCAAGAAGGAGATACACAAGGAGAAAGAATAGAATCTGTTATTTGCAAGAAATCTTTTCTAA

TGAGATGGCTAAAGTTGATGACTCTTTCTTTCATAGGCTTGAAGAGTCATTTTTGGTGGAAGAG

GATAAAAAGCATGAAAGACACCCAATCTTCGGTAATATAGTTGATGAAGTGGCTTATCATGAGA

AGTACCCTACCATCTATCACTTAAGAAAGAAATTGGTTGATTCTACTGACAAGGCAGATTTGAG

GTTAATATACCTTGCTTTGGCACATATGATAAAGTTTAGAGGTCACTTCTTAATCGAAGGAGAC

CTTAATCCAGATAACTCAGACGTTGATAAATTGTTTATTCAACTTGTGCAGACATACAACCAAT

TGTTCGAAGAGAATCCTATCAACGCTAGTGGTGTTGATGCTAAGGCAATACTTTCCGCAAGATT

GTCTAAGTCAAGGAGATTAGAAAATCTTATAGCTCAGTTGCCAGGAGAGAAAAAGAATGGTTTA

TTCGGAAACCTTATCGCATTATCTCTTGGATTGACCCCTAATTTTAAATCAAACTTCGACTTGG

CTGAAGATGCAAAGTTACAACTTTCAAAGGATACTTACGATGACGATTTGGACAATCTTTTGGC

TCAGATTGGAGACCAATATGCAGATTTGTTTTTAGCTGCAAAGAACTTGAGTGATGCTATCCTT

CTTTCCGACATCCTTAGAGTTAACACTGAAATAACAAAGGCTCCACTTAGTGCATCCATGATCA

AAAGATACGATGAACATCACCAAGACTTGACTTTGTTAAAAGCATTGGTTAGACAACAGCTTCC

TGAAAAGTACAAGGAGATCTTTTTCGATCAGTCTAAGAACGGTTATGCTGGATACATAGATGGT

GGAGCATCACAAGAAGAGTTCTACAAATTCATCAAGCCAATCTTGGAAAAGATGGATGGTACAG

AAGAGCTTTTGGTTAAGTTAAACAGAGAAGATTTGCTTAGAAAACAGAGGACCTTCGACAATGG

TTCTATTCCACATCAAATCCACTTGGGAGAATTACATGCTATTCTTAGGAGACAAGAGGATTTT

TATCCTTTCTTGAAGGACAATAGAGAAAAGATTGAGAAGATCCTTACTTTTAGAATTCCATACT

ACGTTGGTCCTTTGGCTAGAGGAAACAGTAGGTTCGCATGGATGACCAGAAAGTCCGAAGAGAC

CATAACTCCATGGAATTTTGAAGAGGTTGTGGATAAAGGTGCTTCTGCACAATCTTTTATTGAA

AGAATGACAAACTTCGATAAGAATTTGCCAAACGAAAAGGTTCTTCCTAAGCATTCTTTGCTTT

ACGAATACTTCACCGTGTACAACGAGCTTACTAAGGTTAAGTACGTGACAGAGGGTATGAGAAA

ACCTGCTTTTCTTTCAGGAGAGCAGAAAAAGGCAATTGTTGATCTTTTGTTCAAGACAAACAGA

AAGGTTACCGTGAAGCAATTGAAGGAAGATTACTTCAAAAAGATAGAGTGCTTCGATAGTGTTG

AAATTTCCGGTGTGGAGGATAGATTCAATGCTTCTTTGGGAACTTACCATGATTTGCTTAAGAT

TATCAAAGACAAGGATTTTCTTGATAATGAAGAGAACGAAGACATATTGGAGGATATTGTTCTT

ACATTGACCTTATTCGAAGATAGAGAGATGATTGAAGAGAGGCTTAAGACTTACGCTCACTTGT

TTGACGATAAAGTGATGAAGCAATTGAAAAGGAGAAGGTATACAGGTTGGGGAAGATTGTCTAG

GAAATTGATTAATGGTATTAGAGATAAGCAGTCTGGAAAAACTATACTTGATTTCTTGAAGTCA

GACGGTTTCGCTAACAGAAACTTCATGCAACTTATCCATGACGATAGTCTTACTTTTAAAGAAG
```

-continued

```
ATATCCAAAAGGCTCAGGTTTCTGGTCAGGGAGATTCATTGCATGAACACATTGCTAATTTGGC

AGGTTCTCCAGCAATCAAAAAGGGAATATTACAAACTGTTAAGGTTGTGGATGAACTTGTTAAA

GTTATGGGTAGACACAAACCTGAGAATATAGTGATTGAAATGGCTAGGGAGAACCAAACTACAC

AGAAGGGACAAAAGAATTCTAGAGAAAGGATGAAGAGAATTGAAGAGGGTATCAAAGAGCTTGG

TTCTCAAATTTTGAAGGAACATCCAGTTGAGAATACCCAACTTCAGAACGAAAAACTTTACTTG

TACTACCTTCAGAACGGTAGAGACATGTATGTGGATCAAGAATTAGACATCAATAGGCTTTCAG

ACTATGATGTTGACCACATAGTGCCTCAATCTTTCTTGAAGGACGATTCAATTGATAATAAGGT

TCTTACTAGAAGTGATAAGAATAGGGGAAAATCCGACAACGTGCCTAGTGAGGAGGTGGTTAAA

AAGATGAAAAATTATTGGAGACAGTTATTGAACGCAAAGCTTATTACACAGAGGAAGTTCGACA

ATTTGACTAAGGCTGAGAGGGGAGGTTTATCTGAGTTGGACAAGGCTGGATTCATTAAGAGACA

ACTTGTTGAAACCAGACAAATAACTAAGCATGTGGCTCAGATCCTTGATTCAAGAATGAACACC

AAGTACGATGAAAACGACAAGTTGATCAGAGAGGTTAAAGTGATTACTCTTAAGAGTAAGTTGG

TTTCCGATTTCAGAAAGGACTTCCAATTCTACAAAGTGAGGGAAATTAATAACTATCATCACGC

TCACGATGCATACTTGAATGCTGTTGTGGGTACTGCATTGATCAAAAAGTACCCAAAGTTAGAA

TCTGAGTTCGTTTATGGAGATTACAAGGTTTACGACGTGAGAAAGATGATTGCTAAGTCAGAAC

AGGAGATTGGTAAAGCTACAGCAAAGTACTTTTTCTATAGTAACATCATGAACTTTTTCAAGAC

TGAAATCACATTGGCTAACGGAGAGATCAGAAAAAGGCCTTTAATAGAAACAAACGGTGAAACC

GGAGAGATTGTTTGGGATAAGGGAAGAGACTTTGCAACTGTTAGGAAGGTGTTGTCCATGCCAC

AAGTTAATATCGTGAAAAAGACTGAAGTTCAGACAGGTGGATTCAGTAAGGAGTCCATACTTCC

TAAAAGAAACAGTGATAAGTTGATTGCTAGGAAAAAGGATTGGGACCCAAAGAAATATGGTGGA

TTTGATAGTCCTACAGTTGCTTACTCCGTGCTTGTTGTGGCAAAGGTTGAAAAGGGTAAATCTA

AAAAGTTGAAGTCAGTGAAGGAGTTGTTAGGAATTACCATCATGGAAAGATCTTCATTTGAGAA

AAATCCAATTGATTTCTTAGAAGCTAAGGGTTACAAGGAGGTTAAAAAGGACTTAATTATCAAA

CTTCCTAAGTACAGTTTGTTCGAATTAGAGAACGGAAGAAAAAGGATGTTAGCTTCCGCAGGTG

AACTTCAAAAGGGAAATGAGCTTGCTTTGCCATCTAAGTACGTTAACTTCTTATATCTTGCATC

TCATTACGAAAAATTGAAGGGTTCACCTGAAGATAATGAGCAAAAGCAGCTTTTCGTTGAACAA

CATAAGCACTATCTTGACGAAATCATAGAGCAGATATCTGAATTCTCAAAGAGAGTTATCCTTG

CTGATGCAAATTTGGACAAAGTGTTATCAGCTTACAACAAACATAGAGATAAGCCAATTAGGGA

ACAAGCAGAGAATATCATACACCTTTTTACCTTGACTAACTTAGGAGCTCCTGCTGCTTTTAAA

TACTTCGATACTACAATCGACAGAAAGAGGTACACATCTACCAAAGAAGTTCTTGATGCAACAT

TGATACACCAGAGTATCACAGGACTTTATGAGACCAGAATAGACCTTTCCCAGTTAGGAGGAGA

TGGATCCACTAGTGGTCCAAAGAAAAAGAGAAAAGTGGCAGCAGCAGCTCCTAAAAAGAAAAGA

AAGGTTGGTGGCAGCAGCGACCCAGCATTCCTTTACAAAGTTGTCTGAGGATCCCTAACTAGGA

TGAGCTAAGCTAGCTATATCATCAATTTATGTATTACACATAATATCGCACTCAGTCTTTCATC

TACGGCAATGTACCAGCTGATATAATCAGTTATTGAAATATTTCTGAATTTAAACTTGCATCAA

TAAATTTATGTTTTTGCTTGGACTATAATACCTGACTTGTTATTTTATCAATAAATATTTAAAC

TATATTTCTTTCAAGATGGGAATTAACATCTACAAATTGCCTTTTCTTATCGACCATGTACCCT

AGGTACCAAGCTTCTCGAGCACGTGCAATGACACTCACAAATCTAGTAGTGGCTGAATTGGCTC

GATGTTAAATGCAAACTAACGAAGTCTCATCAAATAATAACTCTTCTTCTTGCATTTGCTTTCT

TTGCCCCTTTCTCTCTTCTTCCATCTCAAATCTGTCTCTTCAATATTACTATTGGGCTTTTGGT

TAGTCTATAATGGGACTCAAAATAAGGCTTTGGCCCACATCATAAAAGATAAATTCACAAATCA
```

```
AAACTAATTTTCAGAGTCTTTTGTCCCACATCGGTCAATCTACTCGTTTTGTGTTTGTTTATAT
ATTACACGAAACGATGTATTCAACGAATCCAGATTCTGCTACGAAGTTTTAGAGCTAGAAATAG
CAAGTTAAAATAAGGCTAGTCCGTTATCAACTTGAAAAAGTGGCACCGAGTCGGTGCCTAGGTT
TTTTTTCTAGACCCAGCTTTCTTGTACAAAGTTGGCATTACGCTGCACGTGAGCTTTCGTTGAA
CAACGGAAACTCGACTTGCCTTCCGCACAATACATCATTTCTTCTTAGCTTTTTTTCTTCTTCT
TCGTTCATACAGTTTTTTTTGTTTATCAGCTTACATTTTCTTGAACCGTAGCTTTCGTTTTCT
TCTTTTTAACTTTCCATTCGGAGTTTTTGTATCTTGTTTCATAGTTTGTCCCAGGATTAGAATG
ATTAGGCATCGAACCTTCAAGAATTTGATTGAATAAAACATCTTCATTCTTAAGATATGAAGAT
AATCTTCAAAAGGCCCCTGGGAATCTGAAAGAAGAGAAGCAGGCCCATTTATATGGGAAAGAAC
AATAGTATTTCTTATATAGGCCCATTTAAGTTGAAAACAATCTTCAAAAGTCCCACATCGCTTA
GATAAGAAAACGAAGCTGAGTTTATATACAGCTAGAGTCGAAGTAGTGATTGTCGATTACGCTA
AGAAATTGTTTTAGAGCTAGAAATAGCAAGTTAAAATAAGGCTAGTCCGTTATCAACTTGAAAA
AGTGGCACCGAGTCGGTGCCTAGGTTCAAACATTTGGCAATAAAGTTTCTTAAGATTGAATCCT
GTTGCCGGTCTTGCGATGATTATCATATAATTTCTGTTGAATTACGTTAAGCATGTAATAATTA
ACATGTAATGCATGACGTTATTTATGAGATGGGTTTTTATGATTAGAGTCCCGCAATTATACAT
TTAATACGCGCACGTGCTCGAGGACCCAGCTTTCTTGTACAAAGTGGT
>Dual-C4H-IRX7-loci-target (figure Bioediting
constructs C)
                                                         (SEQ ID NO: 33)
GTACCGAGCTCGGATCCACTAGTAACGGCCGCCAGTGTGCTGGAATTCAGGCGGCCGCGTTTGT
AGAGTTGGATCAGCATCCAGATTTAAACCCTTATTTTTGTTTTTGCCAAGCATCCAGACTTAAT
CCTATATTAGATACTGTATATGCATCTTGATGGAATATAGACTATATAGAAAGACCAAAAATGG
AAGAGTACGAATAAAAATGCATAATATACCTTGGAAATTATTCTTGGTTATTGTGAAACTTAAA
ACATTTCAACGAAGTCATATACTATTATTTAATCATTGATTTAAAATTGCTAATCAAATCACGT
GTTGTTGTTATATATGGATAAAGAGTTAAACTATAACACAACTGAGAAAAAAATAAAGTTATCA
ATTTTGTTAAGAATCAATGAAGGTTTCACAAGACTGGGAAGAAAAAAAAATAGATATATGGAGT
ACATAAAACATTAAAATTTTGCTAAATTTTACTTTTGAACTCTATTGATTCGGGTTGACATGAT
GATAATGTTACATTCGTACAATTTCACAATGAAAAAAACGAGTACTAAATATTGTCAATCAAAC
ATATGAATGTACAAAAATCCATAAACTCTACCAAAATAGAATGAAGATTCTGAAATCAAACCTA
CTTTTTCTTTTTAATTATAAATTCAACTATATTATAAATTTATTTATCACAAATAATAGAGGAG
TGAGAATATTTTAGACAACGCAAATTTCTTTTATTTAGTTCTTATACTTTATTTTTTACCAAAC
GTTAATTAAAAAAAATCACACATACATAATTTCTAAAAAAAATGTATTCTTCAAGTAATATATCT
TTCTGAGTACTAGTTTATCTATTTATCTCCGTATTTAATAATCAAAAGTTACGTTTAAAATAGA
AACAACTTTTATCAAACAAAATATATTAGAAAACGCATGGTACTGGCTACTGGAAAGAATCATG
ACCTGTAAATTTCTACAGTTTTCCCGTTTTATATAGTACTTAGAAACTTTGGATTTTCATAGCG
CAACCAATAAACACATGGACTTAAGACACAAAAAAAGTTGGGTGCAATGTCATTAATCAAACTA
AAAAAATAATGATTAAAAGCATGGAATTCCGAAAACGCAACAAAATGATTCTGTGTTTAGACAA
ATGCAGAAAGGCCTCTTAACTAATCTTAAATAAAGTCTTAGTTCCAACCACATAAACACTCCTT
AGCTCCATTAATTTTGGTTTTCTTAATTACGTTTCTACACAAGTACACGTACTTACACATACAA
TTCCACAGTCTAAATGATAAAACTATGTGGTTTTTGACGTCATCGTTACCTTTCTGTCGTCTCA
CCTTTATATAGTGTCTCTAACAGAACGTAACAACCAAATGTTTAAAAAAATAAAAACAGCACCC
CTTAATTAGGCTCATTCGTTTTGCACTAACCATACTACAAATCATCTCGAACGATCGAGCAAAG
```

-continued

```
ATTTGAAAAATAAATAAACGTATAACTCTAGAGATTTTCATTAGCTAAGAAAAGTGAAATCGAT

TGTTAATCCTATTTCAGACGGGACAGGAACACTCATTACCCAACTCTATCATCTCTCGAACACC

AAACTATATCTACCGTTTGGGGCATTATTTCCCACTTTCTTTCGAAGACAATTTCCCATATATA

ACATATACACATTATTACTAATATATTTTTATAAATTTTCGTCACATCCCAAAAAAAAACACTC

TTTGTCACATCAACTAGTTTTTTTGTAACGATCAAACCTTTTCGTTTAAAAAAAAAAAACTTTT

GTAGTGTAAACGTTTATTTATCGATGAAAAAAGCCACATCTTCCGGAGGGAAACTTTTTAAGAC

ACCCTATTTCGACTTTATTTTGTAAATACAGTGTGCATGTGCATATAAAGAGAGATATCATTTG

TATAAATATCAAGAATTAGAAGAGAAAAAGAGAGAAGAAGACAATCTATTACTATTACGATGTG

TGGGTTGTTAATTTGTTTAAAGGGAGCTTTTCTATAGAGATTTTTAAGGTCAAGGGTCATCGTT

CGATGTGGGCTTGCTTCCTACAATCTAGTTGCCTTACGGGGCCTACTCTTTTTCTTTTGATAAC

TACATCACCTTTTTTTTCTCCGACAACTATATATCACTTTTTTTATGTTTTCCTTTTTTTCTTC

ACAATAATTCTTTACTCGTTGCAAATGTAAAGATACACAAAGTTACTTATTTTGTTTACGATGG

TTCTTAGTAGTTTAAAGAATTAATGAATAAGATAAACCTAAACTTTGAAAAGACTAAAAAAAAT

GTATAACAACATACATTATACGTATTTGAAATAGTCCAAGTGATATTATGTCATTGATATTAGC

ACAAATAATTACGATGCCTGATATTGTCACATTTGATGATTTTAAGTTCTTGTAAAGATAAGT

GTAACTAAATCACTATAGTGAGGCCCACGTTTTAATTTCTAAACTAATTACAATGACAATAAAA

TAGCAAAACTATTTAAAACTAGACGCCAAAAAAAATTGAAACTAATAATTGTGAAAAAGAACA

AGAGAATAATAATCATTAATAATTGACAAGTGAAATTAATATATTGCTCTTGGAGGGTTATATT

TTAATTTTCAAACTAAATAATGAATACAAATGGAAAAGCTAATGATAAGAGTTGAATTTTAATA

ATTAAGAAAACAAAAAAAGGTGTACAAGGAGACACATGCGTTTTCCTCATGCATCTTGTTTTT

ATACAACAATATATATATATATATTGAGTCATTCTCTGCTAGCTCTCTCATCTCCAACTTTCAG

TATGATATATAGTTACAATTAAATAAACCTCACATGCTCTATTCTTGCTTGATTTTTGAGTTAA

TCTTGAATCTCTTTGCCTAGCCTGTTATCAACAAGTTTGTACAAAAAAGCAGGCTTCATGGATA

AGAAATACTCAATAGGTTTGGACATAGGAACTAACTCCGTTGGTTGGGCAGTGATAACAGACGA

ATATAAAGTGCCATCTAAAAAGTTCAAAGTTTTAGGTAATACAGATAGACATTCTATTAAGAAA

AATTTGATTGGTGCTTTGTTATTTGATTCCGGAGAAACCGCTGAGGCAACTAGATTGAAGAGGA

CTGCAAGAAGGAGATACACAAGGAGAAAGAATAGAATCTGTTATTTGCAAGAAATCTTTTCTAA

TGAGATGGCTAAAGTTGATGACTCTTTCTTTCATAGGCTTGAAGAGTCATTTTTGGTGGAAGAG

GATAAAAAGCATGAAAGACACCCAATCTTCGGTAATATAGTTGATGAAGTGGCTTATCATGAGA

AGTACCCTACCATCTATCACTTAAGAAAGAAATTGGTTGATTCTACTGACAAGGCAGATTTGAG

GTTAATATACCTTGCTTTGGCACATATGATAAAGTTTAGAGGTCACTTCTTAATCGAAGGAGAC

CTTAATCCAGATAACTCAGACGTTGATAAATTGTTTATTCAACTTGTGCAGACATACAACCAAT

TGTTCGAAGAGAATCCTATCAACGCTAGTGGTGTTGATGCTAAGGCAATACTTTCCGCAAGATT

GTCTAAGTCAAGGAGATTAGAAAATCTTATAGCTCAGTTGCCAGGAGAGAAAAGAATGGTTTA

TTCGGAAACCTTATCGCATTATCTCTTGGATTGACCCCTAATTTTAAATCAAACTTCGACTTGG

CTGAAGATGCAAAGTTACAACTTTCAAAGGATACTTACGATGACGATTTGGACAATCTTTTGGC

TCAGATTGGAGACCAATATGCAGATTTGTTTTTAGCTGCAAAGAACTTGAGTGATGCTATCCTT

CTTTCCGACATCCTTAGAGTTAACACTGAAATAACAAAGGCTCCACTTAGTGCATCCATGATCA

AAAGATACGATGAACATCACCAAGACTTGACTTTGTTAAAAGCATTGGTTAGACAACAGCTTCC

TGAAAAGTACAAGGAGATCTTTTTCGATCAGTCTAAGAACGGTTATGCTGGATACATAGATGGT
```

-continued

```
GGAGCATCACAAGAAGAGTTCTACAAATTCATCAAGCCAATCTTGGAAAAGATGGATGGTACAG

AAGAGCTTTTGGTTAAGTTAAACAGAGAAGATTTGCTTAGAAAACAGAGGACCTTCGACAATGG

TTCTATTCCACATCAAATCCACTTGGGAGAATTACATGCTATTCTTAGGAGACAAGAGGATTTT

TATCCTTTCTTGAAGGACAATAGAGAAAAGATTGAGAAGATCCTTACTTTTAGAATTCCATACT

ACGTTGGTCCTTTGGCTAGAGGAAACAGTAGGTTCGCATGGATGACCAGAAAGTCCGAAGAGAC

CATAACTCCATGGAATTTTGAAGAGGTTGTGGATAAAGGTGCTTCTGCACAATCTTTTATTGAA

AGAATGACAAACTTCGATAAGAATTTGCCAAACGAAAAGGTTCTTCCTAAGCATTCTTTGCTTT

ACGAATACTTCACCGTGTACAACGAGCTTACTAAGGTTAAGTACGTGACAGAGGGTATGAGAAA

ACCTGCTTTTCTTTCAGGAGAGCAGAAAAAGGCAATTGTTGATCTTTTGTTCAAGACAAACAGA

AAGGTTACCGTGAAGCAATTGAAGGAAGATTACTTCAAAAAGATAGAGTGCTTCGATAGTGTTG

AAATTTCCGGTGTGGAGGATAGATTCAATGCTTCTTTGGGAACTTACCATGATTTGCTTAAGAT

TATCAAAGACAAGGATTTTCTTGATAATGAAGAGAACGAAGACATATTGGAGGATATTGTTCTT

ACATTGACCTTATTCGAAGATAGAGAGATGATTGAAGAGAGGCTTAAGACTTACGCTCACTTGT

TTGACGATAAAGTGATGAAGCAATTGAAAAGGAGAAGGTATACAGGTTGGGGAAGATTGTCTAG

GAAATTGATTAATGGTATTAGAGATAAGCAGTCTGGAAAAACTATACTTGATTTCTTGAAGTCA

GACGGTTTCGCTAACAGAAACTTCATGCAACTTATCCATGACGATAGTCTTACTTTTAAAGAAG

ATATCCAAAAGGCTCAGGTTTCTGGTCAGGGAGATTCATTGCATGAACACATTGCTAATTTGGC

AGGTTCTCCAGCAATCAAAAAGGGAATATTACAAACTGTTAAGGTTGTGGATGAACTTGTTAAA

GTTATGGGTAGACACAAACCTGAGAATATAGTGATTGAAATGGCTAGGGAGAACCAAACTACAC

AGAAGGGACAAAAGAATTCTAGAGAAAGGATGAAGAGAATTGAAGAGGGTATCAAAGAGCTTGG

TTCTCAAATTTTGAAGGAACATCCAGTTGAGAATACCCAACTTCAGAACGAAAAACTTTACTTG

TACTACCTTCAGAACGGTAGAGACATGTATGTGGATCAAGAATTAGACATCAATAGGCTTTCAG

ACTATGATGTTGACCACATAGTGCCTCAATCTTTCTTGAAGGACGATTCAATTGATAATAAGGT

TCTTACTAGAAGTGATAAGAATAGGGGAAAATCCGACAACGTGCCTAGTGAGGAGGTGGTTAAA

AAGATGAAAAATTATTGGAGACAGTTATTGAACGCAAAGCTTATTACACAGAGGAAGTTCGACA

ATTTGACTAAGGCTGAGAGGGGAGGTTTATCTGAGTTGGACAAGGCTGGATTCATTAAGAGACA

ACTTGTTGAAACCAGACAAATAACTAAGCATGTGGCTCAGATCCTTGATTCAAGAATGAACACC

AAGTACGATGAAAACGACAAGTTGATCAGAGAGGTTAAAGTGATTACTCTTAAGAGTAAGTTGG

TTTCCGATTTCAGAAAGGACTTCCAATTCTACAAAGTGAGGGAAATTAATAACTATCATCACGC

TCACGATGCATACTTGAATGCTGTTGTGGGTACTGCATTGATCAAAAAGTACCCAAAGTTAGAA

TCTGAGTTCGTTTATGGAGATTACAAGGTTTACGACGTGAGAAAGATGATTGCTAAGTCAGAAC

AGGAGATTGGTAAAGCTACAGCAAAGTACTTTTTCTATAGTAACATCATGAACTTTTTCAAGAC

TGAAATCACATTGGCTAACGGAGAGATCAGAAAAAGGCCTTTAATAGAAACAAACGGTGAAACC

GGAGAGATTGTTTGGGATAAGGGAAGAGACTTTGCAACTGTTAGGAAGGTGTTGTCCATGCCAC

AAGTTAATATCGTGAAAAAGACTGAAGTTCAGACAGGTGGATTCAGTAAGGAGTCCATACTTCC

TAAAAGAAACAGTGATAAGTTGATTGCTAGGAAAAAGGATTGGGACCCAAAGAAATATGGTGGA

TTTGATAGTCCTACAGTTGCTTACTCCGTGCTTGTTGTGGCAAAGGTTGAAAAGGGTAAATCTA

AAAAGTTGAAGTCAGTGAAGGAGTTGTTAGGAATTACCATCATGGAAAGATCTTCATTTGAGAA

AAATCCAATTGATTTCTTAGAAGCTAAGGGTTACAAGGAGGTTAAAAAGGACTTAATTATCAAA

CTTCCTAAGTACAGTTTGTTCGAATTAGAGAACGAAGAAAAGGATGTTAGCTTCCGCAGGTG

AACTTCAAAAGGGAAATGAGCTTGCTTTGCCATCTAAGTACGTTAACTTCTTATATCTTGCATC
```

-continued

```
TCATTACGAAAAATTGAAGGGTTCACCTGAAGATAATGAGCAAAAGCAGCTTTTCGTTGAACAA

CATAAGCACTATCTTGACGAAATCATAGAGCAGATATCTGAATTCTCAAAGAGAGTTATCCTTG

CTGATGCAAATTTGGACAAAGTGTTATCAGCTTACAACAAACATAGAGATAAGCCAATTAGGGA

ACAAGCAGAGAATATCATACACCTTTTTACCTTGACTAACTTAGGAGCTCCTGCTGCTTTTAAA

TACTTCGATACTACAATCGACAGAAAGAGGTACACATCTACCAAAGAAGTTCTTGATGCAACAT

TGATACACCAGAGTATCACAGGACTTTATGAGACCAGAATAGACCTTTCCCAGTTAGGAGGAGA

TGGATCCACTAGTGGTCCAAAGAAAAAGAGAAAAGTGGCAGCAGCAGCTCCTAAAAAGAAAAGA

AAGGTTGGTGGCAGCAGCGACCCAGCATTCCTTTACAAAGTTGTCTGAGGATCCCTAACTAGGA

TGAGCTAAGCTAGCTATATCATCAATTTATGTATTACACATAATATCGCACTCAGTCTTTCATC

TACGGCAATGTACCAGCTGATATAATCAGTTATTGAAATATTTCTGAATTTAAACTTGCATCAA

TAAATTTATGTTTTTGCTTGGACTATAATACCTGACTTGTTATTTTATCAATAAATATTTAAAC

TATATTTCTTTCAAGATGGGAATTAACATCTACAAATTGCCTTTTCTTATCGACCATGTACCCT

AGGTACCAAGCTTCTCGAGCACGTGCAATGACACTCACAAATCTAGTAGTGGCTGAATTGGCTC

GATGTTAAATGCAAACTAACGAAGTCTCATCAAATAATAACTCTTCTTCTTGCATTTGCTTTCT

TTGCCCCTTTCTCTCTTCTTCCATCTCAAATCTGTCTCTTCAATATTACTATTGGGCTTTTGGT

TAGTCTATAATGGGACTCAAAATAAGGCTTTGGCCCACATCATAAAAGATAAATTCACAAATCA

AAACTAATTTTCAGAGTCTTTTGTCCCACATCGGTCAATCTACTCGTTTTGTGTTTGTTTATAT

ATTACACGAAACGATGTATTCAACGACAGGGACAAAGAAGAAATGTTTTAGAGCTAGAAATAGC

AAGTTAAAATAAGGCTAGTCCGTTATCAACTTGAAAAAGTGGCACCGAGTCGGTGCCTAGGTTT

TTTTTCTAGACCCAGCTTTCTTGTACAAAGTTGGCATTACGCTGCACGTGAGCTTTCGTTGAAC

AACGGAAACTCGACTTGCCTTCCGCACAATACATCATTTCTTCTTAGCTTTTTTCTTCTTCTT

CGTTCATACAGTTTTTTTTGTTTATCAGCTTACATTTTCTTGAACCGTAGCTTTCGTTTTCTT

CTTTTTAACTTTCCATTCGGAGTTTTTGTATCTTGTTTCATAGTTTGTCCCAGGATTAGAATGA

TTAGGCATCGAACCTTCAAGAATTTGATTGAATAAAACATCTTCATTCTTAAGATATGAAGATA

ATCTTCAAAAGGCCCCTGGGAATCTGAAAGAAGAGAAGCAGGCCCATTTATATGGGAAAGAACA

ATAGTATTTCTTATATAGGCCCATTTAAGTTGAAAACAATCTTCAAAAGTCCCACATCGCTTAG

ATAAGAAAACGAAGCTGAGTTTATATACAGCTAGAGTCGAAGTAGTGATTGTCGATTACGCTAA

GAAATTGTTTTAGAGCTAGAAATAGCAAGTTAAAATAAGGCTAGTCCGTTATCAACTTGAAAAA

GTGGCACCGAGTCGGTGCCTAGGTTCAAACATTTGGCAATAAAGTTTCTTAAGATTGAATCCTG

TTGCCGGTCTTGCGATGATTATCATATAATTTCTGTTGAATTACGTTAAGCATGTAATAATTAA

CATGTAATGCATGACGTTATTTATGAGATGGGTTTTTATGATTAGAGTCCCGCAATTATACATT

TAATACGCGCACGTGCTCGAGGACCCAGCTTTCTTGTACAAAGTGGT
```

It is understood that the examples and embodiments described herein are for illustrative purposes only and that various modifications or changes in light thereof will be suggested to persons skilled in the art and are to be included within the spirit and purview of this application and scope of the appended claims. All publications, patents, accession number, and patent applications cited herein are hereby incorporated by reference in their entirety for all purposes.

What is claimed is:

1. A method of engineering a plant having reduced lignin content, the method comprising:
introducing a nucleic acid construct into a plant, wherein the construct encodes a gene editing nuclease and comprises a polynucleotide encoding (i) a nuclear-targeted Cas9 domain operably linked to a fiber-specific NST3 promoter, and (ii) a sequence encoding at least a first chimeric RNA comprising a targeting region that selectively hybridizes to a target site in a hydroxycinnamoyl-CoA:shikimate hydroxycinnamoyltransferase (HCT) gene linked to a Cas9 handle;
culturing the plant under conditions in which the nucleic acid construct is expressed and the Cas9 domain cleaves the gene at the target site and reduces or inactivates expression of the HCT gene; and
evaluating lignin content in plant fibers and selecting a plant that has reduced lignin content and does not exhibit reduction in biomass yield compared to wild-type plants.

2. The method of claim 1, wherein the fiber-specific NST3 promoter comprises SEQ ID NO:24.

3. The method of claim 1, wherein the nucleic acid construct further comprises a sequence encoding a second chimeric RNA that comprises a targeting region that selectively hybridizes to a second site in the HCT gene different from the site targeted by the first chimeric RNA.

4. The method of claim 1, wherein the nucleic acid construct further comprises a sequence encoding a second chimeric RNA that comprises a targeting region that selectively hybridizes to a site in a cinnamate 4-hydroxylase (C4H) gene, a coumaryol shikimate 3-hydroxylase (C3H) gene, a cinnamoyl-CoA reductase 1 (CCR1) gene, an irregular xylem 8 (IRX8) gene, an IRX14 gene, an IRX9 gene, an IRX gene7, an IRX10 gene, an IRX15 gene, an F8H gene, a PARVUS gene, a Myb gene, an RWA gene or a TBL gene.

5. The method of claim 4, wherein the nucleic acid construct further comprises a sequence encoding a second chimeric RNA that comprises a targeting region that selectively hybridizes to a site in a C4H gene, a C3H gene, a CCR gene, a Myb63 gene, an IRX7 gene or an IRX8 gene.

6. A plant generated by the method of claim 1.

7. A method of obtaining an increased amount of soluble sugars from a plant in a saccharification reaction, the method comprising:

subjecting the plant of claim 6 to a saccharification reaction, thereby increasing the amount of soluble sugars that can be obtained from the plant as compared to a wild-type plant.

8. Seedlings obtained from a plant of claim 6, wherein the seedlings have fiber-specific reduction in lignin content.

* * * * *

SEQUENCE LISTING

<160> NUMBER OF SEQ ID NOS: 37

<210> SEQ ID NO 1
<211> LENGTH: 95
<212> TYPE: DNA

```
<213> ORGANISM: Artificial Sequence
<220> FEATURE:
<223> OTHER INFORMATION: synthetic sequence encoding chimeric guide RNA
      targeting C4H gene

<400> SEQUENCE: 1
gtcgattacg ctaagaaatt gttttagagc tagaaatagc aagttaaaat aaggctagtc    60
cgttatcaac ttgaaaaagt ggcaccgagt cggtg                              95

<210> SEQ ID NO 2
<211> LENGTH: 95
<212> TYPE: DNA
<213> ORGANISM: Artificial Sequence
<220> FEATURE:
<223> OTHER INFORMATION: synthetic sequence encoding chimeric guide RNA
      targeting C4H gene

<400> SEQUENCE: 2
gatctcttcc tcctccgtat gttttagagc tagaaatagc aagttaaaat aaggctagtc    60
cgttatcaac ttgaaaaagt ggcaccgagt cggtg                              95

<210> SEQ ID NO 3
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting C4H gene

<400> SEQUENCE: 3
gaatccagat tctgctacga agttttagag ctagaaatag caagttaaaa taaggctagt    60
ccgttatcaa cttgaaaaag tggcaccgag tcggtg                             96

<210> SEQ ID NO 4
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting C3H gene

<400> SEQUENCE: 4
gtaacctcta cgacataaaa cgttttagag ctagaaatag caagttaaaa taaggctagt    60
ccgttatcaa cttgaaaaag tggcaccgag tcggtg                             96

<210> SEQ ID NO 5
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting C3H gene

<400> SEQUENCE: 5
gatcttatat gggccgatta tgttttagag ctagaaatag caagttaaaa taaggctagt    60
ccgttatcaa cttgaaaaag tggcaccgag tcggtg                             96

<210> SEQ ID NO 6
<211> LENGTH: 97
<212> TYPE: DNA
<213> ORGANISM: Artificial Sequence
<220> FEATURE:
<223> OTHER INFORMATION: synthetic sequence encoding chimeric guide RNA
      targeting C3H gene
```

```
<400> SEQUENCE: 6
gattatgggc ctcattacgt gagttttaga gctagaaata gcaagttaaa ataaggctag     60
tccgttatca acttgaaaaa gtggcaccga gtcggtg                              97

<210> SEQ ID NO 7
<211> LENGTH: 97
<212> TYPE: DNA
<213> ORGANISM: Artificial Sequence
<220> FEATURE:
<223> OTHER INFORMATION: synthetic sequence encoding chimeric guide RNA
      targeting HCT gene

<400> SEQUENCE: 7
gtcgcttgaa gagagacgat gagttttaga gctagaaata gcaagttaaa ataaggctag     60
tccgttatca acttgaaaaa gtggcaccga gtcggtg                              97

<210> SEQ ID NO 8
<211> LENGTH: 95
<212> TYPE: DNA
<213> ORGANISM: Artificial Sequence
<220> FEATURE:
<223> OTHER INFORMATION: synthetic sequence encoding chimeric guide RNA
      targeting HCT gene

<400> SEQUENCE: 8
gtctacttct acagacccac gttttagagc tagaaatagc aagttaaaat aaggctagtc     60
cgttatcaac ttgaaaaagt ggcaccgagt cggtg                                95

<210> SEQ ID NO 9
<211> LENGTH: 95
<212> TYPE: DNA
<213> ORGANISM: Artificial Sequence
<220> FEATURE:
<223> OTHER INFORMATION: synthetic sequence encoding chimeric guide RNA
      targeting HCT gene

<400> SEQUENCE: 9
gtcccttttt accctatggc gttttagagc tagaaatagc aagttaaaat aaggctagtc     60
cgttatcaac ttgaaaaagt ggcaccgagt cggtg                                95

<210> SEQ ID NO 10
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting CCR gene

<400> SEQUENCE: 10
gttgcgacgg cgtctttcac agttttagag ctagaaatag caagttaaaa taaggctagt     60
ccgttatcaa cttgaaaaag tggcaccgag tcggtg                               96

<210> SEQ ID NO 11
<211> LENGTH: 97
<212> TYPE: DNA
<213> ORGANISM: Artificial Sequence
<220> FEATURE:
<223> OTHER INFORMATION: synthetic sequence encoding chimeric guide RNA
      targeting CCR gene

<400> SEQUENCE: 11
gcttctcctg tcaccgacga tcgttttaga gctagaaata gcaagttaaa ataaggctag     60
```

```
tccgttatca acttgaaaaa gtggcaccga gtcggtg                              97
```

<210> SEQ ID NO 12
<211> LENGTH: 94
<212> TYPE: DNA
<213> ORGANISM: Artificial Sequence
<220> FEATURE:
<223> OTHER INFORMATION: synthetic sequence encoding chimeric guide RNA
      targeting CCR gene

<400> SEQUENCE: 12

```
gacttctgca aaacaccag ttttagagct agaaatagca agttaaaata aggctagtcc     60
gttatcaact tgaaaaagtg gcaccgagtc ggtg                                94
```

<210> SEQ ID NO 13
<211> LENGTH: 95
<212> TYPE: DNA
<213> ORGANISM: Artificial Sequence
<220> FEATURE:
<223> OTHER INFORMATION: synthetic sequence encoding chimeric guide RNA
      targeting Myb gene

<400> SEQUENCE: 13

```
ggaagagttg tcgtctaagg gttttagagc tagaaatagc aagttaaaat aaggctagtc    60
cgttatcaac ttgaaaaagt ggcaccgagt cggtg                               95
```

<210> SEQ ID NO 14
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting Myb gene

<400> SEQUENCE: 14

```
gtggcaactt cacttcagag ggttttagag ctagaaatag caagttaaaa taaggctagt    60
ccgttatcaa cttgaaaaag tggcaccgag tcggtg                              96
```

<210> SEQ ID NO 15
<211> LENGTH: 96
<212> TYPE: DNA
<213> ORGANISM: Artificial Sequence
<220> FEATURE:
<223> OTHER INFORMATION: synthetic sequence encoding chimeric guide RNA
      targeting Myb gene

<400> SEQUENCE: 15

```
gataacgaga tcaagaatgt ggttttagag ctagaaatag caagttaaaa taaggctagt    60
ccgttatcaa cttgaaaaag tggcaccgag tcggtg                              96
```

<210> SEQ ID NO 16
<211> LENGTH: 95
<212> TYPE: DNA
<213> ORGANISM: Artificial Sequence
<220> FEATURE:
<223> OTHER INFORMATION: synthetic sequence encoding chimeric guide RNA
      targeting IRX7 gene

<400> SEQUENCE: 16

```
gacagggaca aagaagaaat gttttagagc tagaaatagc aagttaaaat aaggctagtc    60
cgttatcaac ttgaaaaagt ggcaccgagt cggtg                               95
```

<210> SEQ ID NO 17
<211> LENGTH: 97
<212> TYPE: DNA
<213> ORGANISM: Artificial Sequence
<220> FEATURE:
<223> OTHER INFORMATION: synthetic sequence encoding chimeric guide RNA targeting IRX7 gene

<400> SEQUENCE: 17

```
gaagttgcaa gagacataga cagttttaga gctagaaata gcaagttaaa ataaggctag    60
tccgttatca acttgaaaaa gtggcaccga gtcggtg                             97
```

<210> SEQ ID NO 18
<211> LENGTH: 96
<212> TYPE: DNA
<213> ORGANISM: Artificial Sequence
<220> FEATURE:
<223> OTHER INFORMATION: synthetic sequence encoding chimeric guide RNA targeting IRX7 gene

<400> SEQUENCE: 18

```
ggatgaagtt ccatcttgcc agttttagag ctagaaatag caagttaaaa taaggctagt    60
ccgttatcaa cttgaaaaag tggcaccgag tcgtg                               96
```

<210> SEQ ID NO 19
<211> LENGTH: 95
<212> TYPE: DNA
<213> ORGANISM: Artificial Sequence
<220> FEATURE:
<223> OTHER INFORMATION: synthetic sequence encoding chimeric guide RNA targeting IRX8 gene

<400> SEQUENCE: 19

```
gatggaacag agaacaagaa gttttagagc tagaaatagc aagttaaaat aaggctagtc    60
cgttatcaac ttgaaaaagt ggcaccgagt cggtg                               95
```

<210> SEQ ID NO 20
<211> LENGTH: 97
<212> TYPE: DNA
<213> ORGANISM: Artificial Sequence
<220> FEATURE:
<223> OTHER INFORMATION: synthetic sequence encoding chimeric guide RNA targeting IRX8 gene

<400> SEQUENCE: 20

```
gaagctgagc ttgtccctat gtgttttaga gctagaaata gcaagttaaa ataaggctag    60
tccgttatca acttgaaaaa gtggcaccga gtcggtg                             97
```

<210> SEQ ID NO 21
<211> LENGTH: 94
<212> TYPE: DNA
<213> ORGANISM: Artificial Sequence
<220> FEATURE:
<223> OTHER INFORMATION: synthetic sequence encoding chimeric guide RNA targeting IRX8 gene

<400> SEQUENCE: 21

```
gacaatattc ttgcagcttg ttttagagct agaaatagca agttaaaata aggctagtcc    60
gttatcaact tgaaaaagtg gcaccgagtc ggtg                                94
```

<210> SEQ ID NO 22
<211> LENGTH: 2837
<212> TYPE: DNA
<213> ORGANISM: Arabidopsis thaliana
<220> FEATURE:
<221> NAME/KEY: promoter

<400> SEQUENCE: 22

```
gtttgtagag ttggatcagc atccagattt aaacccttat ttttgttttt gccaagcatc      60
cagacttaat cctatattag atactgtata tgcatcttga tggaatatag actatataga     120
aagaccaaaa atggaagagt acgaataaaa atgcataata taccttggaa attattcttg     180
gttattgtga aacttaaaac atttcaacga agtcatatac tattatttaa tcattgattt     240
aaaattgcta atcaaatcac gtgttgttgt tatatatgga taaagagtta aactataaca     300
caactgagaa aaaaataaag ttatcaattt tgttaagaat caatgaaggt ttcacaagac     360
tgggaagaaa aaaaaataga tatatggagt acataaaaca ttaaaatttt gctaaatttt     420
acttttgaac tctattgatt cgggttgaca tgatgataat gttacattcg tacaatttca     480
caatgaaaaa aacgagtact aaatattgtc aatcaaacat atgaatgtac aaaaatccat     540
aaactctacc aaaatagaat gaagattctg aaatcaaacc tacttttttct ttttaattat     600
aaattcaact atattataaa tttatttatc acaaataata gaggagtgag aatattttag     660
acaacgcaaa tttcttttat ttagttctta tactttattt tttaccaaac gttaattaaa     720
aaaatcacac atacataatt tctaaaaaaa atgtattctt caagtaatat atctttctga     780
gtactagttt atctatttat ctccgtattt aataatcaaa agttacgttt aaaatagaaa     840
caacttttat caaacaaaat atattagaaa acgcatggta ctggctactg gaaagaatca     900
tgacctgtaa atttctacag ttttcccgtt ttatatagta cttagaaact ttggattttc     960
atagcgcaac caataaacac atggacttaa gacacaaaaa aagttgggtg caatgtcatt    1020
aatcaaacta aaaaaataat gattaaaagc atggaattcc gaaaacgcaa caaaatgatt    1080
ctgtgtttag acaaatgcag aaaggcctct taactaatct taaataaagt cttagttcca    1140
accacataaa cactccttag ctccattaat tttggttttc ttaattacgt ttctacacaa    1200
gtacacgtac ttacacatac aattccacag tctaaatgat aaaactatgt ggttttttgac   1260
gtcatcgtta cctttctgtc gtctcacctt tatatagtgt ctctaacaga acgtaacaac    1320
caaatgttta aaaaaataaa aacagcaccc cttaattagg ctcattcgtt ttgcactaac    1380
catactacaa atcatctcga acgatcgagc aaagatttga aaaataaata aacgtataac    1440
tctagagatt tcattagct aagaaaagtg aaatcgattg ttaatcctat ttcagacggg     1500
acaggaacac tcattaccca actctatcat ctctcgaaca ccaaactata tctaccgttt    1560
ggggcattat ttcccacttt ctttcgaaga caatttccca tatataacat atacacatta    1620
ttactaatat attttttataa attttcgtca catcccaaaa aaaaacactc tttgtcacat    1680
caactagttt ttttgtaacg atcaaacctt ttcgtttaaa aaaaaaaaac ttttgtagtg    1740
taaacgttta tttatcgatg aaaaaagcca catcttccgg agggaaactt tttaagacac    1800
cctatttcga ctttatttg taaatacagt gtgcatgtgc atataaagag agatatcatt    1860
tgtataaata tcaagaatta gaagagaaaa agagagaaga agacaatcta ttactattac    1920
gatgtgtggg ttgttaattt gtttaaaggg agcttttcta tagagatttt taaggtcaag    1980
ggtcatcgtt cgatgtgggc ttgcttccta caatctagtt gccttacggg gcctactctt    2040
tttcttttga taactacatc accttttttt tctccgacaa ctatatatca cttttttttat   2100
gttttccttt ttttcttcac aataattctt tactcgttgc aaatgtaaag atacacaaag    2160
ttacttattt tgtttacgat ggttcttagt agtttaaaga attaatgaat aagataaacc    2220
```

```
taaactttga aaagactaaa aaaaatgtat aacaacatac attatacgta tttgaaatag    2280
tccaagtgat attatgtcat tgatattagc acaaataatt acgatgcctg atattgtcac    2340
atttgatgat tttaagttct tgtaaaagat aagtgtaact aaatcactat agtgaggccc    2400
acgttttaat ttctaaacta attacaatga caataaaata gcaaaactat ttaaaactag    2460
acgccaaaaa aaattgaaac taataattgt gaaaaaagaa caagagaata ataatcatta    2520
ataattgaca agtgaaatta atatattgct cttggagggt tatattttaa ttttcaaact    2580
aaataatgaa tacaaatgga aaagctaatg ataagagttg aattttaata attaagaaaa    2640
acaaaaaaag gtgtacaagg agacacatgc gttttcctca tgcatcttgt ttttatacaa    2700
caatatatat atatatattg agtcattctc tgctagctct ctcatctcca actttcagta    2760
tgatatatag ttacaattaa ataaacctca catgctctat tcttgcttga tttttgagtt    2820
aatcttgaat ctctttg                                                   2837

<210> SEQ ID NO 23
<211> LENGTH: 2710
<212> TYPE: DNA
<213> ORGANISM: Arabadopsis thaliana
<220> FEATURE:
<221> NAME/KEY: promoter

<400> SEQUENCE: 23
aacggtggcg tgatggagct tcatcctccc atcttcgccg aattcatcac caacgaattt      60
cccggccatg tcatccacga ctctttaagc ctccgccact catctccacc gcttctccac     120
ggcgaagaac tctttcccgg taacatctac tacctccttc ctctttcttc ttccgcagcc     180
gcgaccgctc aactggattc ctccgaccaa ctatcaacgc cgtacagaat gtctttcggg     240
aagacgccga taatggcggc tttgagtggc ggtggttgtg gagtgtggaa ggtgaggctt     300
gtgataagtc cggagcagtt ggcggaaatt cttgcggagg atgtggaaac ggaagcgttg     360
gtggaaagtg tgaggacggt ggcgaagtgt ggcggttacg gctgcggcgg aggagttcat     420
tcgagagcga attcagacca gctaagcgtt acgagtagct ttaaagggaa attgtggtaa     480
aatttcgaat tatgaataaa ctacgttat gttttaatct gtttcacgat ttaagcattt      540
aaattagtat gttgatttcc gtattcattg aagacttgga acgattatat aagtttatca     600
acgtagatat atttgaaata tcattgttat ctctcatgaa acaattaatt tatgaagtcg     660
tagactcgta gttagagatt attaatctt ccctattcaa tgccaaaagt ctagaagagc      720
aaaacaaaag ggagaaactc ttttatttca ggcccaatga cacaaagctg ccagaaaca     780 gtttaagatt aggctaaagt tataagtccg acaagcacga gtgctaatat atatagttat     840
atgacgtctc accattaagg gtttaataaa ttttgaaaca cctcaaatta agattgcttc     900
ccatgcaaac ttccttcatc ttctagaaaa attacgattt gtaatacttc aattatatca     960 ttttagttttt tgtcactaa ttatcatcaa tttatcatag ctccgtgccg caacaacgtt    1020
cgttttaatc agattatata ttactctgct ataaactcag aaccatgtta gaaaatgaa    1080 aaagacattt cagaatattc attaactcaa aattttaatc tcatgattta atttttatt    1140 aacaatgtta tcctatagca catggcaaat ttgaacggcc cttgcgtatt aatctattat    1200
aatctcaaaa ccatgtgtaa gaaaaggaa attcagaaaa taacctttg taaataggcc     1260 cccacaaaat ctacaacata cgtagatacc tcctcgctta cagttgtaaa caactgttca    1320
tctagattca tgccgtcatt caagtttaaa ttaatacaat aatttaaaat ttaatttgg    1380 atgaatcgaa tccaccgtcg tttcctgaat accagatagg ttaactttat gattagttcg    1440
```

```
agtgaaccac atgcacaata ttcgaatctt agacattcgt tgcaatgtta acttcacata    1500
tatttgataa acgcttcttg aatcagatct taatctcttt ctttctctcc atcttctaag    1560
gaggttgtgg attatcatgt agtatatcat tatcttcgca tcaccttcaa caagaacaag    1620
ctacgagctt taaagtcgta tttaacacaa taatgtataa agtctttctt catcacatca    1680
catacatttt ttgttgccat caccctttcat tcactttttt tgttaacact attcgtttct    1740
atataaaata aaaataaaat gaggaatgtc ttgtccatag agattttaa ggtcgagggt    1800 catcggagcg atgtgggctt gcttcctaca ttatagttga tatgtggatc ccgcgtggac    1860 catatttta cccaatagct acgtgcatgg tcccaccgct ctctctcacg cactattccg    1920
aaattgccat aaacaatttc accggacaaa aagagcaaat aatttcgatg tttaataaag    1980
agaccattag tatatttgac ccaaaaaaaa ataaaaaaaa aagagagaca ttactataac    2040
ttttattaga tgaaatattg caacattgta tttataacgg atctaattta ctgaatcata    2100 tttttttct tgttaaaga gatactgaat catgcagaaa aatagataga ttttaaata    2160 ctaggtgaac tcatgacgaa tcaaccatta cgagagattt ctggataaaa gcaaaaacaa    2220
aacaaaacta acatgctaat ctaggcaatt agtagagcga aaagtcggca aaaccaaagg    2280
ccgaagaagc ttgatcgata tactttttt ttttgtttt ggctggatat acttggtatg    2340
aactaagaat taagtaaaaa ctcataggga gtaattttc gagaagtgca ttcactatga    2400
gtataaaaca gacattttca aattattaaa acaagctctt agaggctcat atgtttaatt    2460
gtaagtggcg gctcatgcga acttataatg aaaacatcaa atattcggaa aaataatact    2520
ccactgttaa aaagaaaact taacaaagga attaaaaata tgagagcaaa agaacacatg    2580
cattttctca tgcatgtact attatttatt ttttgcaga gttgatgtaa aaaatataca    2640
catatatata gacatacttt ggttagttat aaactcgttc tattttcttc tccttttct    2700 atctttagca                                                           2710
```

<210> SEQ ID NO 24
<211> LENGTH: 3027
<212> TYPE: DNA
<213> ORGANISM: Arabadopsis thaliana

<400> SEQUENCE: 24

```
attctacaca ttcacaaagt ttactacact atatataatt tacccaacaa acacttattt      60
tactgcatta ttcagtatat tatcttacct ataaatgtgt atcatcatca tcaataacgc    120
gattatttgt gctgaaggat tatatattca aaatgatcta gttatatatg tcacatgatt    180
gccgttaaca agacacattt gaagaagcta agcaagaaaa acggacactt ttgcgacttg    240
ttacataatt taacttatag gtcaaaagaa tttgattagt cattgcaact acgtgtggat    300
gtcactttct attcaaccaa aactcacaat attatatgat ctagttttgt cgtattactg    360
atttgtatta taaatgtta tttaatttga attctacgta gatattgctc atgcatgata    420
gtatgtatct aaactattca ataactaac tacgtggata ttttataatc caagtaaaaa    480
gcagaaagtg ggtaactacg tcagtatgac tatactttta tcggaattgc ttgacatcca    540 aactttgct atgcttcacc aaccaatgca gtttcactta attattaact attgactatg    600
tcttattaag ttagcactaa ttcgttaatc attcaaaacg ttatttgatt gaattacata    660
ttacactctc tttctgcatc accactcaca ccatatgcaa ctataaccaa ctcatcacat    720
tcaaatgtat taattggatt ttggtgcgag attaaaaatt gaaggaaac aaaatatgat    780
```

```
aatgggataa aatcttgaac ggaaactcaa actaatcctc ataaggtata acaaaataac      840
aatttaagct aagcacaaca acatacaagt tcgacctttt cctttgatga tccagcccaa      900
cagttctctt atatctcaaa ccattcgacc atttgagcca aactagctaa acctgcagga      960
atcaaaacca acaaagattc agattagcta aaccggtttc atcccttgt cacatgactc     1020 acatccgtct tctacataac gatttctaat gatgtgagct cttaacttgc tccagcaaga     1080
tcatcaactt tggagcacct tcaatgattt agttaacatg ttagataaat taaatattct     1140
tgtttcaata tatatcaact ttagtgtaaa agccttaaca ttctcttgaa tatttaattt     1200
atttctcctt atttcgattt aatgacaaat gtgaattaat ttttgtgata ttttttgttcg     1260 aaattagttt tcagttaata acatacatgt gagcatggga cacacatgat ttaacaaaag     1320
ggaatgacga aatgatatat caaaatatta gtatgggaac aaattacgag gtgaaacttc     1380
acactcaact caattaaaac tagaataaag aaatggaaaa agtgaaagaa tgagaggtca     1440
aatgtggtta atcattatgt ggtattagtt aatccatcaa ttgtgtaccc aaaagcatga     1500
ttaagcatag aatttagaga aacaaaacat cattattaat gttgaaacac aaagatccca     1560
tcaacagaca aatgataagt acagtgcatg tagggtaaca acttttatgt acatgttata     1620
tacttatatt atataataag aaaacgatta aagtgtcatt gctccagcct ctatttgtaa     1680
atcatattat atcagtatgc ttaattccaa taattaagtc cataactaaa atatatacac     1740
atatatgtat gttaaatggt tgaatatata catatatttt cataaacaaa tattgctaat     1800
taattcagtt atttgtgtac ataatccaac tatcacctttt ttagctggaa gtggatattc     1860
caacatgtca gtcctgtcact cccacattca tactctctat tcttttttagc tatttcaata     1920 tctacggtta aatattaatg gctatatagc cttaccctctc attttagttt tttttttggta     1980 ttcgcataac catcgaatac tcaaacttac tatgtaagat ggtctgaata actatttccg     2040
atttaagatg aatagctaga ttgaaatata catgcactaa ttggacatgc actaaaggca     2100
gaggtgaatt aaatgatgaa atgaagatga agtgtcacac ttgtgcaaaa agcatgtccc     2160
ctgctcttct ccgcttgttt caatttcttt gactttcatc acgttttttgt cacttaaata     2220 caccaaaaaa tatagtacaa ttaaacatcg aaaatcgtcc aaaaagaaga aaaaaaatca     2280
tggaaagttc tttcgttaat gttacacaca ttatcttgat taggtgacac cagatattag     2340
aataaaaatg atagattatg aaaagaaaaa aaaaattgat gtattttttag gatacatcga     2400 aaggaatgaa cataccaaaa acatgggaaa aaatagataa ctaattaaca tggtagaatg     2460
tagatgacgt agatcatgaa acgagtgtgt gatatattaa tgaaaattat tttaatatac     2520
gtagctatat tagaaaataa tttacatttta tttttcttcta aacaaatcta tactttatat     2580
ttacatacat tagtaaagac caaaacacat ggaattcaaa ttctgcaata agtaattgca     2640
agaaaacaca aagattaatc ccccactaaa cccgtttatt tacgttagta ttttttccgtt     2700 ttatacatta cacatgacat gacattacac gtcaaaagaa atatgtctta cgtcagaact     2760
tacgtatgat caaactcgat ttaaacatag aaacatctgt ttactaaatt atactaattt     2820
cataaagaca ctttaatgca tgaacttctt tgtttaaata acaatttccc ccttttgggg     2880
gctatgtctc gtcgagtcct accaccatta taaattatct catcgtttgc tttcttttttt     2940 ttaagttgta accatttcca ctcgtaatca tacaacttct ctactcttct agagcaaaaa     3000
cccaaaaata tattgctatc ttcgtta                                         3027
```

<210> SEQ ID NO 25
<211> LENGTH: 449

<212> TYPE: DNA
<213> ORGANISM: Arabadopsis thaliana

<400> SEQUENCE: 25

```
agctttcgtt gaacaacgga aactcgactt gccttccgca caatacatca tttcttctta    60
gctttttttc ttcttcttcg ttcatacagt ttttttttgt ttatcagctt acattttctt   120
gaaccgtagc tttcgttttc ttcttttttaa ctttccattc ggagttttg tatcttgttt    180
catagtttgt cccaggatta gaatgattag gcatcgaacc ttcaagaatt tgattgaata   240
aaacatcttc attcttaaga tatgaagata atcttcaaaa ggcccctggg aatctgaaag   300
aagagaagca ggcccattta tatgggaaag aacaatagta tttcttatat aggcccattt   360
aagttgaaaa caatcttcaa aagtcccaca tcgcttagat aagaaaacga agctgagttt   420
atatacagct agagtcgaag tagtgattg                                     449
```

<210> SEQ ID NO 26
<211> LENGTH: 519
<212> TYPE: DNA
<213> ORGANISM: Oryza sativa
<220> FEATURE:
<221> NAME/KEY: promoter

<400> SEQUENCE: 26

```
ggtttgtgaa agttgaatta cggcatagcc gaaggaataa cagaatcgtt tcacactttc    60
gtaacaaagg tcttcttatc atgtttcaga cgatggaggc aaggctgatc aaagtgatca   120
agcacataaa cgcatttttt taccatgttt cactccataa gcgtctgaga ttatcacaag   180
tcacgtctag tagtttgatg gtacactagt gacaatcagt tcgtgcagac agagctcata   240
cttgactact tgagcgatta caggcgaaag tgtgaaacgc atgtgatgtg ggctgggagg   300
aggagaatat atactaatgg gccgtatcct gatttgggct gcgtcggaag gtgcagccca   360
cgcgcgccgt accgcgcggg tggcgctgct acccacttta gtccgttgga tggggatccg   420
atggtttgcg cggtggcgtt gcggggatg tttagtacca catcggaaac cgaaagacga    480
tggaaccagc ttataaaccc gcgcgctgta gtcagcttg                          519
```

<210> SEQ ID NO 27
<211> LENGTH: 320
<212> TYPE: DNA
<213> ORGANISM: Arabadopsis thaliana
<220> FEATURE:
<221> NAME/KEY: promoter

<400> SEQUENCE: 27

```
caatgacact cacaaatcta gtagtggctg aattggctcg atgttaaatg caaactaacg    60
aagtctcatc aaataataac tcttcttctt gcatttgctt tctttgcccc tttctctctt   120
cttccatctc aaatctgtct cttcaatatt actattgggc ttttggttag tctataatgg   180
gactcaaaat aaggctttgg cccacatcat aaaagataaa ttcacaaatc aaaactaatt   240
ttcagagtct tttgtcccac atcggtcaat ctactcgttt tgtgtttgtt tatatattac   300
acgaaacgat gtattcaacg                                               320
```

<210> SEQ ID NO 28
<211> LENGTH: 315
<212> TYPE: DNA
<213> ORGANISM: Arabidopsis thaliana
<220> FEATURE:
<221> NAME/KEY: promoter
```

<400> SEQUENCE: 28

```
atgttgttac cagaaagtaa ataaatgttc aatctctgat gttctcaagt aagtgagtct      60
tattgggaat aatttaaact catgttcttc ttgcatttga tttctttgcc actctcttct     120
tctatctcaa atctgtctat actatctcac tactgggctt tttattagtc tacaatggga     180
ctcaaaataa ggctttggcc aacatcaaaa agataagtca caaaccaaaa ctaaattcag     240
agtcttttct cccacatcgg tcactgtact cattttgtgt ttgtttatat attacacgaa     300
ccgatctttg ttacg                                                      315
```

<210> SEQ ID NO 29
<211> LENGTH: 313
<212> TYPE: DNA
<213> ORGANISM: Arabidopsis thaliana
<220> FEATURE:
<221> NAME/KEY: promoter

<400> SEQUENCE: 29

```
ttcttatggc tcagcctgtg atggataact gaatcaaaca aatggcgtct gggtttaaga      60
agatctgttt tggctatgtt ggacgaaaca agtgaacttt taggatcaac ttccgtttat     120
atacggagct tatatcgagc aataagataa gtgggctttt tatgtaattt aatgggctat     180
cgtccatata ttcactaata cccatgccca gtacccatgt atgcgtttca tataagctcc     240
taatttctcc cacatcgctc aaatctaaac aaatcttgtt gtatatataa cactgaggga     300
gcaccattgg tca                                                        313
```

<210> SEQ ID NO 30
<211> LENGTH: 325
<212> TYPE: DNA
<213> ORGANISM: Arabadopsis thaliana
<220> FEATURE:
<221> NAME/KEY: promoter

<400> SEQUENCE: 30

```
tttactttaa attttttctt atgcagcctg tgatggataa ctgaatcaaa caaatggcgt      60
ctgggtttaa gaagatctgt tttggctatg ttggacgaaa caagtgaact tttaggatca     120
acttcagttt atatatggag cttatatcga gcaataagat aagtgggctt tttatgtaat     180
ttaatgggct atcgtccata gattcactaa tacccatgcc cagtacccat gtatgcgttt     240
catataagct cctaatttct cccacatcgc tcaaatctaa acaaatcttg ttgtatatat     300
aacactgagg gagcaacatt ggtca                                           325
```

<210> SEQ ID NO 31
<211> LENGTH: 8208
<212> TYPE: DNA
<213> ORGANISM: Artificial Sequence
<220> FEATURE:
<223> OTHER INFORMATION: synthetic Cas9 construct that targets a CH4
      gene

<400> SEQUENCE: 31

```
gtaccgagct cggatccact agtaacggcc gccagtgtgc tggaattcag gcggccgcgt      60
tgtagagtt ggatcagcat ccagatttaa acccttattt tgttttttgc caagcatcca     120
gacttaatcc tatattagat actgtatatg catcttgatg gaatatagac tatatagaaa     180
gaccaaaaat ggaagagtac gaataaaaat gcataatata ccttggaaat tattcttggt     240
tattgtgaaa cttaaaacat ttcaacgaag tcatatacta ttatttaatc attgatttaa     300
```

```
aattgctaat caaatcacgt gttgttgtta tatatggata aagagttaaa ctataacaca    360
actgagaaaa aaataaagtt atcaattttg ttaagaatca atgaaggttt cacaagactg    420
ggaagaaaaa aaaatagata tatggagtac ataaaacatt aaaattttgc taaattttac    480
ttttgaactc tattgattcg ggttgacatg atgataatgt tacattcgta caatttcaca    540
atgaaaaaaa cgagtactaa atattgtcaa tcaaacatat gaatgtacaa aaatccataa    600
actctaccaa aatagaatga agattctgaa atcaaaccta cttttctctt ttaattataa    660
attcaactat attataaatt tatttatcac aaataataga ggagtgagaa tattttagac    720
aacgcaaatt tcttttattt agttcttata ctttatttttt taccaaacgt taattaaaaa    780
aatcacacat acataatttc taaaaaaaat gtattcttca agtaatatat ctttctgagt    840
actagtttat ctatttatct ccgtatttaa taatcaaaag ttacgtttaa aatagaaaca    900
acttttatca aacaaaatat attagaaaac gcatggtact ggctactgga aagaatcatg    960
acctgtaaat ttctacagtt ttcccgtttt atatagtact tagaaacttt ggattttcat    1020
agcgcaacca ataaacacat ggacttaaga cacaaaaaaa gttgggtgca atgtcattaa    1080
tcaaactaaa aaaataatga ttaaaagcat ggaattccga aaacgcaaca aaatgattct    1140
gtgtttagac aaatgcagaa aggcctctta actaatctta aataaagtct tagttccaac    1200
cacataaaca ctccttagct ccattaattt tggttttctt aattacgttt ctacacaagt    1260
acacgtactt acacatacaa ttccacagtc taaatgataa aactatgtgg ttttttgacgt    1320 catcgttacc tttctgtcgt ctcacccttta tatagtgtct ctaacagaac gtaacaacca    1380
aatgtttaaa aaaataaaaa cagcacccct taattaggct cattcgtttt gcactaacca    1440
tactacaaat catctcgaac gatcgagcaa agatttgaaa aataaataaa cgtataactc    1500
tagagatttt cattagctaa gaaaagtgaa atcgattgtt aatcctattt cagacgggac    1560
aggaacactc attacccaac tctatcatct ctcgaacacc aaactatatc taccgtttgg    1620
ggcattattt cccactttct ttcgaagaca atttcccata taacatat acacattatt     1680 actaatatat ttttataaat tttcgtcaca tcccaaaaaa aaacactctt tgtcacatca    1740
actagttttt ttgtaacgat caaacctttt cgtttaaaaa aaaaaaactt tgtagtgta    1800 aacgtttatt tatcgatgaa aaaagccaca tcttccggag ggaaacttttt taagacaccc    1860 tatttcgact ttattttgta aatacagtgt gcatgtgcat ataaagagag atatcatttg    1920
tataaatatc aagaattaga agagaaaaag agagaagaag acaatctatt actattacga    1980
tgtgtgggtt gttaatttgt ttaaagggag cttttctata gagatttta aggtcaaggg      2040 tcatcgttcg atgtgggctt gcttcctaca atctagttgc cttacggggc ctactctttt    2100
tcttttgata actacatcac cttttttttc tccgacaact atatatcact tttttttatgt   2160 tttccttttt ttcttcacaa taattcttta ctcgttgcaa atgtaaagat acacaaagtt    2220
acttattttg tttacgatgg ttcttagtag tttaaagaat taatgaataa gataaaccta    2280
aactttgaaa agactaaaaa aaatgtataa caacatacat tatacgtatt tgaaatagtc    2340
caagtgatat tatgtcattg atattagcac aaataattac gatgcctgat attgtcacat    2400
ttgatgattt taagttcttg taaaagataa gtgtaactaa atcactatag tgaggcccac    2460
gttttaattt ctaaactaat tacaatgaca ataaaatagc aaaactatttt aaaactagac   2520 gccaaaaaaa attgaaacta ataattgtga aaaaagaaca agagaataat aatcattaat    2580
aattgacaag tgaaattaat atattgctct tggagggtta tattttaatt ttcaaactaa    2640
ataatgaata caaatggaaa agctaatgat aagagttgaa ttttaataat taagaaaaac    2700
```

```
aaaaaaaggt gtacaaggag acacatgcgt tttcctcatg catcttgttt ttatacaaca    2760
atatatatat atatattgag tcattctctg ctagctctct catctccaac tttcagtatg    2820
atatatagtt acaattaaat aaacctcaca tgctctattc ttgcttgatt tttgagttaa    2880
tcttgaatct ctttgcctag cctgttatca acaagtttgt acaaaaaagc aggcttcatg    2940
gataagaaat actcaatagg tttggacata ggaactaact ccgttggttg ggcagtgata    3000
acagacgaat ataaagtgcc atctaaaaag ttcaaagttt taggtaatac agatagacat    3060
tctattaaga aaaatttgat tggtgctttg ttatttgatt ccggagaaac cgctgaggca    3120
actagattga agaggactgc aagaaggaga tacacaagga gaaagaatag aatctgttat    3180
ttgcaagaaa tcttttctaa tgagatggct aaagttgatg actctttctt tcataggctt    3240
gaagagtcat ttttggtgga agaggataaa aagcatgaaa gacacccaat cttcggtaat    3300
atagttgatg aagtggctta tcatgagaag taccctacca tctatcactt aagaaagaaa    3360
ttggttgatt ctactgacaa ggcagatttg aggttaatat accttgcttt ggcacatatg    3420
ataaagttta gaggtcactt cttaatcgaa ggagacctta atccagataa ctcagacgtt    3480
gataaattgt ttattcaact tgtgcagaca tacaaccaat tgttcgaaga gaatcctatc    3540
aacgctagtg gtgttgatgc taaggcaata ctttccgcaa gattgtctaa gtcaaggaga    3600
ttagaaaatc ttatagctca gttgccagga gagaaaaaga atggtttatt cggaaacctt    3660
atcgcattat ctcttggatt gaccectaat tttaaatcaa acttcgactt ggctgaagat    3720
gcaaagttac aactttcaaa ggatacttac gatgacgatt tggacaatct tttggctcag    3780
attggagacc aatatgcaga tttgttttta gctgcaaaga acttgagtga tgctatcctt    3840
ctttccgaca tccttagagt taacactgaa ataacaaagg ctccacttag tgcatccatg    3900
atcaaaagat acgatgaaca tcaccaagac ttgactttgt taaaagcatt ggttagacaa    3960
cagcttcctg aaaagtacaa ggagatcttt ttcgatcagt ctaagaacgg ttatgctgga    4020
tacatagatg gtggagcatc acaagaagag ttctacaaat tcatcaagcc aatcttggaa    4080
aagatggatg gtacagaaga gcttttggtt aagttaaaca gagaagattt gcttagaaaa    4140
cagaggacct tcgacaatgg ttctattcca catcaaatcc acttgggaga attacatgct    4200
attcttagga gacaagagga ttttttatcct ttcttgaagg acaatagaga aaagattgag    4260
aagatcctta cttttagaat tccatactac gttggtcctt tggctagagg aaacagtagg    4320
ttcgcatgga tgaccagaaa gtccgaagag accataactc catggaattt tgaagaggtt    4380
gtggataaag gtgcttctgc acaatctttt attgaaagaa tgacaaactt cgataagaat    4440
ttgccaaacg aaaaggttct tcctaagcat tctttgcttt acgaatactt caccgtgtac    4500
aacgagctta ctaaggttaa gtacgtgaca gagggtatga gaaaacctgc ttttctttca    4560
ggagagcaga aaaaggcaat tgttgatctt ttgttcaaga caaacagaaa ggttaccgtg    4620
aagcaattga aggaagatta cttcaaaaag atagagtgct tcgatagtgt tgaaatttcc    4680
ggtgtggagg atagattcaa tgcttctttg gaacttacc atgatttgct taagattatc    4740
aaagacaagg atttttcttga taatgaagag aacgaagaca tattggagga tattgttctt    4800
acattgacct tattcgaaga tagagagatg attgaagaga ggcttaagac ttacgctcac    4860
ttgtttgacg ataaagtgat gaagcaattg aaaaggagaa ggtatacagg ttggggaaga    4920
ttgtctagga aattgattaa tggtattaga gataagcagt ctggaaaaac tatacttgat    4980
ttcttgaagt cagacggttt cgctaacaga aacttcatgc aacttatcca tgacgatagt    5040
```

| | |
|---|---|
| cttactttta aagaagatat ccaaaaggct caggtttctg gtcaggaga ttcattgcat | 5100 |
| gaacacattg ctaatttggc aggttctcca gcaatcaaaa agggaatatt acaaactgtt | 5160 |
| aaggttgtgg atgaacttgt taaagttatg ggtagacaca aacctgagaa tatagtgatt | 5220 |
| gaaatggcta gggagaacca aactacacag aagggacaaa agaattctag agaaaggatg | 5280 |
| aagagaattg aagagggtat caaagagctt ggttctcaaa ttttgaagga acatccagtt | 5340 |
| gagaataccc aacttcagaa cgaaaaactt tacttgtact accttcagaa cggtagagac | 5400 |
| atgtatgtgg atcaagaatt agacatcaat aggctttcag actatgatgt tgaccacata | 5460 |
| gtgcctcaat ctttcttgaa ggacgattca attgataata aggttcttac tagaagtgat | 5520 |
| aagaataggg gaaaatccga caacgtgcct agtgaggagg tggttaaaaa gatgaaaaat | 5580 |
| tattggagac agttattgaa cgcaaagctt attacacaga ggaagttcga caatttgact | 5640 |
| aaggctgaga ggggaggttt atctgagttg acaaggctg gattcattaa gagacaactt | 5700 |
| gttgaaacca gacaaataac taagcatgtg gctcagatcc ttgattcaag aatgaacacc | 5760 |
| aagtacgatg aaaacgacaa gttgatcaga gaggttaaag tgattactct taagagtaag | 5820 |
| ttggtttccg atttcagaaa ggacttccaa ttctacaaag tgagggaaat taataactat | 5880 |
| catcacgctc acgatgcata cttgaatgct gttgtgggta ctgcattgat caaaaagtac | 5940 |
| ccaaagttag aatctgagtt cgtttatgga gattacaagg tttacgacgt gagaaagatg | 6000 |
| attgctaagt cagaacagga gattggtaaa gctacagcaa agtacttttt ctatagtaac | 6060 |
| atcatgaact ttttcaagac tgaaatcaca ttggctaacg gagagatcag aaaaaggcct | 6120 |
| ttaatagaaa caaacggtga aaccggagag attgtttggg ataagggaag agactttgca | 6180 |
| actgttagga aggtgttgtc catgccacaa gttaatatcg tgaaaaagac tgaagttcag | 6240 |
| acaggtggat tcagtaagga gtccatactt cctaaaagaa acagtgataa gttgattgct | 6300 |
| aggaaaaagg attgggaccc aaagaaatat ggtggatttg atagtcctac agttgcttac | 6360 |
| tccgtgcttg ttgtggcaaa ggttgaaaag ggtaaatcta aaagttgaa gtcagtgaag | 6420 |
| gagttgttag gaattaccat catggaaaga tcttcatttg agaaaaatcc aattgatttc | 6480 |
| ttagaagcta aggggtacaa ggaggttaaa aaggacttaa ttatcaaact tcctaagtac | 6540 |
| agtttgttcg aattagagaa cggaagaaaa aggatgttag cttccgcagg tgaacttcaa | 6600 |
| aagggaaatg agcttgcttt gccatctaag tacgttaact tcttatatct tgcatctcat | 6660 |
| tacgaaaaat tgaagggttc acctgaagat aatgagcaaa agcagctttt cgttgaacaa | 6720 |
| cataagcact atcttgacga aatcatagag cagatatctg aattctcaaa gagagttatc | 6780 |
| cttgctgatg caaatttgga caaagtgtta tcagcttaca caaacatag agataagcca | 6840 |
| attagggaac aagcagagaa tatcatacac cttttttacct tgactaactt aggagctcct | 6900 |
| gctgctttta aatacttcga tactacaatc gacagaaaga ggtacacatc taccaaagaa | 6960 |
| gttcttgatg caacattgat acaccagagt atcacaggac tttatgagac cagaatagac | 7020 |
| cttttcccagt taggaggaga tggatccact agtggtccaa agaaaaagag aaaagtggca | 7080 |
| gcagcagctc ctaaaaagaa aagaaaggtt ggtggcagca gcgacccagc attcctttac | 7140 |
| aaagttgtct gaggatccct aactaggatg agctaagcta gctatatcat caatttatgt | 7200 |
| attacacata atatcgcact cagtctttca tctacggcaa tgtaccagct gatataatca | 7260 |
| gttattgaaa tatttctgaa tttaaacttg catcaataaa tttatgtttt tgcttggact | 7320 |
| ataatacctg acttgttatt ttatcaataa atatttaaac tatatttctt tcaagatggg | 7380 |
| aattaacatc tacaaattgc cttttcttat cgaccatgta ccctaggtac caagcttctc | 7440 |

-continued

```
gagagctttc gttgaacaac ggaaactcga cttgccttcc gcacaataca tcatttcttc    7500 ttagctttt ttcttcttct tcgttcatac agttttttt tgtttatcag cttacatttt    7560
cttgaaccgt agcttcgtt ttcttctttt taactttcca ttcggagttt tgtatcttg    7620 tttcatagtt tgtcccagga ttagaatgat taggcatcga accttcaaga atttgattga    7680
ataaaacatc ttcattctta agatatgaag ataatcttca aaaggcccct gggaatctga    7740
aagaagagaa gcaggcccat ttatatggga aagaacaata gtatttctta tataggccca    7800
tttaagttga aaacaatctt caaaagtccc acatcgctta gataagaaaa cgaagctgag    7860
tttatataca gctagagtcg aagtagtgat tgtcgattac gctaagaaat tgttttagag    7920
ctagaaatag caagttaaaa taaggctagt ccgttatcaa cttgaaaaag tggcaccgag    7980
tcggtgccta ggttcaaaca tttggcaata agtttctta agattgaatc ctgttgccgg    8040
tcttgcgatg attatcatat aatttctgtt gaattacgtt aagcatgtaa taattaacat    8100
gtaatgcatg acgttattta tgagatgggt ttttatgatt agagtcccgc aattatacat    8160
ttaatacgcg cacgtgctcg aggacccagc tttcttgtac aaagtggt               8208
```

<210> SEQ ID NO 32
<211> LENGTH: 8688
<212> TYPE: DNA
<213> ORGANISM: Artificial Sequence
<220> FEATURE:
<223> OTHER INFORMATION: synthetic Cas9 construct that targets two sites of a CH4 gene

<400> SEQUENCE: 32

```
gtaccgagct cggatccact agtaacggcc gccagtgtgc tggaattcag gcggccgcgt      60
ttgtagagtt ggatcagcat ccagatttaa acccttattt tgttttttgc caagcatcca     120
gacttaatcc tatattagat actgtatatg catcttgatg gaatatagac tatatagaaa     180
gaccaaaaat ggaagagtac gaataaaaat gcataatata ccttggaaat tattcttggt     240
tattgtgaaa cttaaaacat ttcaacgaag tcatatacta ttatttaatc attgatttaa     300
aattgctaat caaatcacgt gttgttgtta tatatggata aagagttaaa ctataacaca     360
actgagaaaa aaataaagtt atcaatttg ttaagaatca atgaaggttt cacaagactg     420
ggaagaaaaa aaaatagata tatggagtac ataaaacatt aaaattttgc taaatttac     480 ttttgaactc tattgattcg ggttgacatg atgataatgt tacattcgta caatttcaca     540
atgaaaaaaa cgagtactaa atattgtcaa tcaaacatat gaatgtacaa aaatccataa     600
actctaccaa aatagaatga agattctgaa atcaaaccta ctttttcttt taattataa     660 attcaactat attataaatt tatttatcac aaataataga ggagtgagaa tattttagac     720
aacgcaaatt tcttttattt agttcttata ctttatttt taccaaacgt taattaaaaa     780
aatcacacat acataatttc taaaaaaaat gtattcttca agtaatatat ctttctgagt     840 actagttat ctatttatct ccgtatttaa taatcaaaag ttacgtttaa aatagaaaca     900 actttatca aacaaaatat attagaaaac gcatggtact ggctactgga aagaatcatg     960
acctgtaaat ttctacagtt ttcccgtttt atatagtact tagaaacttt ggattttcat    1020
agcgcaacca ataaacacat ggacttaaga cacaaaaaaa gttgggtgca atgtcattaa    1080
tcaaactaaa aaaataatga ttaaaagcat ggaattccga aaacgcaaca aaatgattct    1140
gtgtttagac aaatgcagaa aggcctctta actaatctta aataaagtct tagttccaac    1200
cacataaaca ctccttagct ccattaattt tggttttctt aattacgttt ctacacaagt    1260
```

```
acacgtactt acacatacaa ttccacagtc taaatgataa aactatgtgg tttttgacgt   1320
catcgttacc tttctgtcgt ctcacctta tatagtgtct ctaacagaac gtaacaacca   1380
aatgtttaaa aaaataaaaa cagcacccct taattaggct cattcgtttt gcactaacca   1440
tactacaaat catctcgaac gatcgagcaa agatttgaaa aataaataaa cgtataactc   1500
tagagatttt cattagctaa gaaaagtgaa atcgattgtt aatcctattt cagacgggac   1560
aggaacactc attacccaac tctatcatct ctcgaacacc aaactatatc taccgtttgg   1620
ggcattattt cccactttct ttcgaagaca atttcccata tataacatat acacattatt   1680
actaatatat ttttataaat tttcgtcaca tcccaaaaaa aaacactctt tgtcacatca   1740
actagttttt ttgtaacgat caaacctttt cgtttaaaaa aaaaaaactt ttgtagtgta   1800
aacgtttatt tatcgatgaa aaaagccaca tcttccggag ggaaacttttt taagacaccc   1860 tatttcgact ttattttgta aatacagtgt gcatgtgcat ataaagagag atatcatttg   1920
tataaatatc aagaattaga agagaaaaag agagaagaag acaatctatt actattacga   1980
tgtgtgggtt gttaatttgt ttaaagggag cttttctata gagatttta aggtcaaggg   2040 tcatcgttcg atgtgggctt gcttcctaca atctagttgc cttacggggc ctactctttt   2100
tcttttgata actcatcac cttttttttc tccgacaact atatatcact tttttatgt    2160 tttccttttt ttcttcacaa taattcttta ctcgttgcaa atgtaaagat acacaaagtt   2220 acttatttg tttacgatgg ttcttagtag tttaaagaat taatgaataa gataaaccta   2280
aactttgaaa agactaaaaa aaatgtataa caacatacat tatacgtatt tgaaatagtc   2340
caagtgatat tatgtcattg atattagcac aaataattac gatgcctgat attgtcacat   2400
ttgatgattt taagttcttg taaaagataa gtgtaactaa atcactatag tgaggcccac   2460
gttttaattt ctaaactaat tacaatgaca ataaaatagc aaaactattt aaaactagac   2520
gccaaaaaaa attgaaacta ataattgtga aaaagaaca agagaataat aatcattaat   2580
aattgacaag tgaaattaat atattgctct tggagggtta tatttaattt ttcaaactaa   2640
ataatgaata caaatggaaa agctaatgat aagagttgaa ttttaataat taagaaaaac   2700
aaaaaaaggt gtacaaggag acacatgcgt tttcctcatg catcttgttt ttatacaaca   2760
atatatatat atatattgag tcattctctg ctagctctct catctccaac tttcagtatg   2820
atatatagtt acaattaaat aaacctcaca tgctctattc ttgcttgatt tttgagttaa   2880
tcttgaatct ctttgcctag cctgttatca acaagtttgt acaaaaaagc aggcttcatg   2940
gataagaaat actcaatagg tttggacata ggaactaact ccgttggttg ggcagtgata   3000
acagacgaat ataaagtgcc atctaaaaag ttcaaagttt taggtaatac agatagacat   3060
tctattaaga aaaatttgat tggtgctttg ttatttgatt ccggagaaac cgctgaggca   3120
actagattga gaggactgc aagaaggaga tacacaagga gaaagaatag aatctgttat   3180
ttgcaagaaa tcttttctaa tgagatggct aaagttgatg actctttctt tcataggctt   3240
gaagagtcat ttttggtgga agaggataaa aagcatgaaa gacacccaat cttcggtaat   3300
atagttgatg aagtggctta tcatgagaag taccctacca tctatcactt aagaaagaaa   3360
ttggttgatt ctactgacaa ggcagatttg aggttaatat accttgcttt ggcacatatg   3420
ataaagttta gaggtcactt cttaatcgaa ggagacctta atccagataa ctcagacgtt   3480
gataaattgt ttattcaact tgtgcagaca tacaaccaat tgttcgaaga gaatcctatc   3540
aacgctagtg gtgttgatgc taaggcaata cttttccgcaa gattgtctaa gtcaaggaga   3600
```

```
ttagaaaatc ttatagctca gttgccagga gagaaaaaga atggtttatt cggaaacctt    3660
atcgcattat ctcttggatt gacccctaat tttaaatcaa acttcgactt ggctgaagat    3720
gcaaagttac aactttcaaa ggatacttac gatgacgatt tggacaatct tttggctcag    3780
attggagacc aatatgcaga tttgttttta gctgcaaaga acttgagtga tgctatcctt    3840
ctttccgaca tccttagagt taacactgaa ataacaaagg ctccacttag tgcatccatg    3900
atcaaaagat acgatgaaca tcaccaagac ttgactttgt taaaagcatt ggttagacaa    3960
cagcttcctg aaaagtacaa ggagatcttt ttcgatcagt ctaagaacgg ttatgctgga    4020
tacatagatg tggagcatc acaagaagag ttctacaaat tcatcaagcc aatcttggaa    4080
aagatggatg gtacagaaga gcttttggtt aagttaaaca gagaagattt gcttagaaaa    4140
cagaggacct tcgacaatgg ttctattcca catcaaatcc acttgggaga attacatgct    4200
attcttagga gacaagagga ttttatcct ttcttgaagg acaatagaga aaagattgag    4260
aagatcctta cttttagaat tccatactac gttggtcctt tggctagagg aaacagtagg    4320
ttcgcatgga tgaccagaaa gtccgaagag accataactc catggaattt tgaagaggtt    4380
gtggataaag tgcttctgc acaatctttt attgaaagaa tgacaaactt cgataagaat    4440
ttgccaaacg aaaaggttct tcctaagcat tctttgcttt acgaatactt caccgtgtac    4500
aacgagctta ctaaggttaa gtacgtgaca gagggtatga aaaacctgc ttttctttca    4560 ggagagcaga aaaaggcaat tgttgatctt ttgttcaaga caaacagaaa ggttaccgtg    4620
aagcaattga aggaagatta cttcaaaaag atagagtgct tcgatagtgt tgaaatttcc    4680
ggtgtggagg atagattcaa tgcttctttg ggaacttacc atgatttgct taagattatc    4740
aaagacaagg attttcttga taatgaagag aacgaagaca tattggagga tattgttctt    4800
acattgacct tattcgaaga tagagagatg attgaagaga ggcttaagac ttacgctcac    4860
ttgtttgacg ataaagtgat gaagcaattg aaaaggagaa ggtatacagg ttggggaaga    4920
ttgtctagga aattgattaa tggtattaga gataagcagt ctggaaaaac tatacttgat    4980
ttcttgaagt cagacggttt cgctaacaga aacttcatgc aacttatcca tgacgatagt    5040
cttactttta aagaagatat ccaaaaggct caggtttctg tcagggaga ttcattgcat    5100 gaacacattg ctaatttggc aggttctcca gcaatcaaaa agggaatatt acaaactgtt    5160
aaggttgtgg atgaacttgt taaagttatg ggtagacaca aacctgagaa tatagtgatt    5220
gaaatggcta gggagaacca aactacacag aagggacaaa agaattctag agaaaggatg    5280
aagagaattg aagagggtat caagagctt ggttctcaaa ttttgaagga acatccagtt    5340
gagaataccc aacttcagaa cgaaaaactt tacttgtact accttcagaa cggtagagac    5400
atgtatgtgg atcaagaatt agacatcaat aggctttcag actatgatgt tgaccacata    5460
gtgcctcaat cttcttgaa ggacgattca attgataata aggttcttac tagaagtgat    5520
aagaataggg gaaatccga caacgtgcct agtgaggagg tggttaaaaa gatgaaaaat    5580
tattggagac agttattgaa cgcaaagctt attacacaga ggaagttcga caatttgact    5640
aaggctgaga ggggaggttt atctgagttg acaaggctg gattcattaa gagacaactt    5700
gttgaaacca gacaaataac taagcatgtg gctcagatcc ttgattcaag aatgaacacc    5760
aagtacgatg aaaacgacaa gttgatcaga gaggttaaag tgattactct taagagtaag    5820 ttggttccg atttcagaaa ggacttccaa ttctacaaag tgagggaaat taataactat    5880
catcacgctc acgatgcata cttgaatgct gttgtgggta ctgcattgat caaaagtac    5940 ccaaagttag aatctgagtt cgtttatgga gattacaagg tttacgacgt gagaaagatg    6000
```

```
attgctaagt cagaacagga gattggtaaa gctacagcaa agtactttt ctatagtaac    6060
atcatgaact ttttcaagac tgaaatcaca ttggctaacg gagagatcag aaaaaggcct    6120
ttaatagaaa caaacggtga aaccggagag attgtttggg ataagggaag agactttgca    6180
actgttagga aggtgttgtc catgccacaa gttaatatcg tgaaaaagac tgaagttcag    6240
acaggtggat tcagtaagga gtccatactt cctaaaagaa acagtgataa gttgattgct    6300
aggaaaaagg attgggaccc aaagaaatat ggtggatttg atagtcctac agttgcttac    6360
tccgtgcttg ttgtggcaaa ggttgaaaag ggtaaatcta aaagttgaa gtcagtgaag    6420
gagttgttag gaattaccat catggaaaga tcttcatttg agaaaaatcc aattgatttc    6480
ttagaagcta agggttacaa ggaggttaaa aaggacttaa ttatcaaact tcctaagtac    6540
agtttgttcg aattagagaa cggaagaaaa aggatgttag cttccgcagg tgaacttcaa    6600
aagggaaatg agcttgcttt gccatctaag tacgttaact tcttatatct tgcatctcat    6660
tacgaaaaat tgaagggttc acctgaagat aatgagcaaa agcagctttt cgttgaacaa    6720
cataagcact atcttgacga aatcatagag cagatatctg aattctcaaa gagagttatc    6780
cttgctgatg caaatttgga caaagtgtta tcagcttaca caaacatag agataagcca    6840
attagggaac aagcagagaa tatcatacac cttttacct tgactaactt aggagctcct    6900
gctgcttta aatacttcga tactacaatc gacagaaaga ggtacacatc taccaaagaa    6960
gttcttgatg caacattgat acaccagagt atcacaggac tttatgagac cagaatagac    7020
cttttcccagt taggaggaga tggatccact agtggtccaa agaaaaagag aaaagtggca    7080
gcagcagctc ctaaaaagaa aagaaaggtt ggtggcagca gcgacccagc attcctttac    7140
aaagttgtct gaggatccct aactaggatg agctaagcta gctatatcat caatttatgt    7200
attacacata atatcgcact cagtctttca tctacggcaa tgtaccagct gatataatca    7260
gttattgaaa tatttctgaa tttaaacttg catcaataaa tttatgtttt tgcttggact    7320
ataatacctg acttgttatt ttatcaataa atatttaaac tatatttctt tcaagatggg    7380
aattaacatc tacaaattgc cttttcttat cgaccatgta ccctaggtac caagcttctc    7440
gagcacgtgc aatgacactc acaaatctag tagtggctga attggctcga tgttaaatgc    7500
aaactaacga agtctcatca aataataact cttcttcttg catttgcttt ctttgcccct    7560
ttctctcttc ttccatctca aatctgtctc ttcaatatta ctattgggct tttggttagt    7620
ctataatggg actcaaaata aggctttggc ccacatcata aaagataaat tcacaaatca    7680
aaactaattt tcagagtctt ttgtcccaca tcggtcaatc tactcgtttt gtgtttgttt    7740
atatattaca cgaaacgatg tattcaacga atccagattc tgctacgaag ttttagagct    7800
agaaatagca agttaaaata aggctagtcc gttatcaact tgaaaaagtg gcaccgagtc    7860
ggtgcctagg tttttttct agacccagct ttcttgtaca agttggcat tacgctgcac    7920
gtgagctttc gttgaacaac ggaaactcga cttgccttcc gcacaataca tcatttcttc    7980
ttagcttttt ttcttcttct tcgttcatac agtttttttt tgtttatcag cttacatttt    8040
cttgaaccgt agctttcgtt ttcttctttt taacttccca ttcggagttt ttgtatcttg    8100
tttcatagtt tgtcccagga ttagaatgat taggcatcga accttcaaga atttgattga    8160
ataaaacatc ttcattctta agatatgaag ataatcttca aaaggcccct gggaatctga    8220
aagaagagaa gcaggcccat ttatatggga agaacaata gtatttctta tataggccca    8280
tttaagttga aacaatctt caaaagtccc acatcgctta gataagaaaa cgaagctgag    8340
```

```
tttatataca gctagagtcg aagtagtgat tgtcgattac gctaagaaat tgttttagag      8400
ctagaaatag caagttaaaa taaggctagt ccgttatcaa cttgaaaaag tggcaccgag      8460
tcggtgccta ggttcaaaca tttggcaata aagtttctta agattgaatc ctgttgccgg      8520
tcttgcgatg attatcatat aatttctgtt gaattacgtt aagcatgtaa taattaacat      8580
gtaatgcatg acgttattta tgagatgggt ttttatgatt agagtcccgc aattatacat      8640
ttaatacgcg cacgtgctcg aggacccagc tttcttgtac aaagtggt                  8688

<210> SEQ ID NO 33
<211> LENGTH: 8687
<212> TYPE: DNA
<213> ORGANISM: Artificial Sequence
<220> FEATURE:
<223> OTHER INFORMATION: synthetic Cas9 construct that targets a site in
      an IRX7 gene and a second site in a CH4 gene

<400> SEQUENCE: 33
gtaccgagct cggatccact agtaacggcc gccagtgtgc tggaattcag gcggccgcgt        60
ttgtagagtt ggatcagcat ccagatttaa acccttattt ttgttttttgc caagcatcca      120 gacttaatcc tatattagat actgtatatg catcttgatg gaatatagac tatatagaaa      180
gaccaaaaat ggaagagtac gaataaaaat gcataatata ccttggaaat tattcttggt      240
tattgtgaaa cttaaaacat ttcaacgaag tcatatacta ttatttaatc attgatttaa      300
aattgctaat caaatcacgt gttgttgtta tatatggata aagagttaaa ctataacaca      360
actgagaaaa aaataaagtt atcaatttttg ttaagaatca atgaaggttt cacaagactg      420
ggaagaaaaa aaaatagata tatggagtac ataaaacatt aaaattttgc taaatttttac     480 ttttgaactc tattgattcg ggttgacatg atgataatgt tacattcgta caatttcaca      540
atgaaaaaaa cgagtactaa atattgtcaa tcaaacatat gaatgtacaa aaatccataa      600
actctaccaa aatagaatga agattctgaa atcaaaccta ctttttcttt ttaattataa      660
attcaactat attataaatt tatttatcac aaataataga ggagtgagaa tattttagac      720
aacgcaaatt tcttttattt agttcttata ctttattttt taccaaacgt taattaaaaa      780
aatcacacat acataatttc taaaaaaaat gtattcttca agtaatatat ctttctgagt      840
actagtttat ctatttatct ccgtatttaa taatcaaaag ttacgtttaa aatagaaaca      900
acttttatca aacaaaatat attagaaaac gcatggtact ggctactgga aagaatcatg      960
acctgtaaat ttctacagtt ttcccgtttt atatagtact tagaaacttt ggattttcat     1020
agcgcaacca ataaacacat ggacttaaga cacaaaaaaa gttgggtgca atgtcattaa     1080
tcaaactaaa aaaataatga ttaaaagcat ggaattccga aaacgcaaca aaatgattct     1140
gtgtttagac aaatgcagaa aggcctctta actaatctta ataaagtct tagttccaac      1200 cacataaaca ctccttagct ccattaattt tggttttctt aattacgttt ctacacaagt     1260
acacgtactt acacatacaa ttccacagtc taaatgataa aactatgtgg ttttgacgt      1320 catcgttacc tttctgtcgt ctcaccttta tatagtgtct ctaacagaac gtaacaacca     1380
aatgtttaaa aaaataaaaa cagcaccccct taattaggct cattcgtttt gcactaacca    1440
tactacaaat catctcgaac gatcgagcaa agatttgaaa aataaataaa cgtataactc     1500
tagagatttt cattagctaa gaaaagtgaa atcgattgtt aatcctattt cagacgggac     1560
aggaacactc attcccaac tctatcatct ctcgaacacc aaactatatc taccgtttgg     1620
ggcattattt cccactttct ttcgaagaca atttcccata tataacatat acacattatt     1680
```

```
actaatatat ttttataaat tttcgtcaca tcccaaaaaa aaacactctt tgtcacatca    1740
actagttttt ttgtaacgat caaacctttt cgtttaaaaa aaaaaaactt ttgtagtgta    1800
aacgtttatt tatcgatgaa aaaagccaca tcttccggag ggaaactttt taagacaccc    1860
tatttcgact ttattttgta aatacagtgt gcatgtgcat ataaagagag atatcatttg    1920
tataaatatc aagaattaga agagaaaaag agagaagaag acaatctatt actattacga    1980
tgtgtgggtt gttaatttgt ttaaagggag cttttctata gagatttta aggtcaaggg    2040 tcatcgttcg atgtgggctt gcttcctaca atctagttgc cttacggggc ctactctttt    2100
tcttttgata actacatcac cttttttttc tccgacaact atatatcact tttttatgt    2160 tttcctttt ttcttcacaa taattcttta ctcgttgcaa atgtaaagat acacaaagtt    2220
acttattttg tttacgatgg ttcttagtag tttaaagaat taatgaataa gataaaccta    2280
aactttgaaa agactaaaaa aaatgtataa caacatacat tatacgtatt tgaaatagtc    2340
caagtgatat tatgtcattg atattagcac aaataattac gatgcctgat attgtcacat    2400
ttgatgattt taagttcttg taaaagataa gtgtaactaa atcactatag tgaggcccac    2460
gttttaattt ctaaactaat tacaatgaca ataaaatagc aaaactattt aaaactagac    2520
gccaaaaaaa attgaaacta ataattgtga aaaaagaaca agagaataat aatcattaat    2580
aattgacaag tgaaattaat atattgctct tggagggtta tattttaatt ttcaaactaa    2640
ataatgaata caaatggaaa agctaatgat aagagttgaa ttttaataat taagaaaaac    2700 aaaaaaggt gtacaaggag acacatgcgt tttcctcatg catcttgttt ttatacaaca    2760
atatatatat atatattgag tcattctctg ctagctctct catctccaac tttcagtatg    2820
atatatagtt acaattaaat aaacctcaca tgctctattc ttgcttgatt tttgagttaa    2880
tcttgaatct ctttgcctag cctgttatca acaagtttgt acaaaaaagc aggcttcatg    2940
gataagaaat actcaatagg tttggacata ggaactaact ccgttggttg ggcagtgata    3000
acagacgaat ataagtgcc atctaaaaag ttcaaagttt taggtaatac agatagacat    3060
tctattaaga aaaatttgat tggtgctttg ttatttgatt ccggagaaac cgctgaggca    3120
actagattga agaggactgc aagaaggaga tacacaagga gaaagaatag aatctgttat    3180
ttgcaagaaa tcttttctaa tgagatggct aaagttgatg actcttctt tcataggctt    3240 gaagagtcat ttttggtgga agaggataaa aagcatgaaa gacacccaat cttcggtaat    3300
atagttgatg aagtggctta tcatgagaag taccctacca tctatcactt aagaaagaaa    3360
ttggttgatt ctactgacaa ggcagatttg aggttaatat accttgcttt ggcacatatg    3420
ataaagttta gaggtcactt cttaatcgaa ggagacctta atccagataa ctcagacgtt    3480
gataaattgt ttattcaact tgtgcagaca tacaaccaat tgttcgaaga gaatcctatc    3540
aacgctagtg gtgttgatgc taaggcaata ctttccgcaa gattgtctaa gtcaaggaga    3600
ttagaaaatc ttatagctca gttgccagga gagaaaaaga atggtttatt cggaaacctt    3660
atcgcattat ctcttggatt gaccctaat tttaaatcaa acttcgactt ggctgaagat    3720
gcaaagttac aactttcaaa ggatacttac gatgacgatt tggacaatct tttggctcag    3780
attggagacc aatatgcaga tttgttttta gctgcaaaga acttgagtga tgctatcctt    3840 cttttccgaca tccttagagt taacactgaa ataacaaagg ctccacttag tgcatccatg    3900
atcaaaagat acgatgaaca tcaccaagac ttgactttgt taaaagcatt ggttagacaa    3960
cagcttcctg aaaagtacaa ggagatcttt ttcgatcagt ctaagaacgg ttatgctgga    4020
tacatagatg gtggagcatc acaagaagag ttctacaaat tcatcaagcc aatcttggaa    4080
```

```
aagatggatg gtacagaaga gcttttggtt aagttaaaca gagaagattt gcttagaaaa    4140
cagaggacct tcgacaatgg ttctattcca catcaaatcc acttgggaga attacatgct    4200
attcttagga gacaagagga tttttatcct ttcttgaagg acaatagaga aaagattgag    4260
aagatcctta cttttagaat tccatactac gttggtcctt tggctagagg aaacagtagg    4320
ttcgcatgga tgaccagaaa gtccgaagag accataactc catggaattt tgaagaggtt    4380
gtggataaag gtgcttctgc acaatctttt attgaaagaa tgacaaactt cgataagaat    4440
ttgccaaacg aaaaggttct tcctaagcat tctttgcttt acgaatactt caccgtgtac    4500
aacgagctta ctaaggttaa gtacgtgaca gagggtatga gaaaacctgc ttttcttttca    4560 ggagagcaga aaaaggcaat tgttgatctt ttgttcaaga caaacagaaa ggttaccgtg    4620
aagcaattga aggaagatta cttcaaaaag atagagtgct tcgatagtgt tgaaatttcc    4680
ggtgtggagg atagattcaa tgcttctttg gaacttacc atgatttgct taagattatc    4740
aaagacaagg attttcttga taatgaagag aacgaagaca tattggagga tattgttctt    4800
acattgacct tattcgaaga tagagagatg attgaagaga ggcttaagac ttacgctcac    4860
ttgtttgacg ataaagtgat gaagcaattg aaaaggagaa ggtatacagg ttggggaaga    4920
ttgtctagga aattgattaa tggtattaga gataagcagt ctggaaaaac tatacttgat    4980
ttcttgaagt cagacggttt cgctaacaga aacttcatgc aacttatcca tgacgatagt    5040
cttactttta aagaagatat ccaaaaggct caggtttctg gtcagggaga ttcattgcat    5100
gaacacattg ctaatttggc aggttctcca gcaatcaaaa agggaatatt acaaactgtt    5160
aaggttgtgg atgaacttgt taaagttatg ggtagacaca aacctgagaa tatagtgatt    5220
gaaatggcta gggagaacca aactacacag aagggacaaa agaattctag agaaaggatg    5280
aagagaattg aagagggtat caaagagctt ggttctcaaa ttttgaagga acatccagtt    5340
gagaataccc aacttcagaa cgaaaaactt tacttgtact accttcagaa cggtagagac    5400
atgtatgtgg atcaagaatt agacatcaat aggctttcag actatgatgt tgaccacata    5460
gtgcctcaat cttcttgaa ggacgattca attgataata aggttcttac tagaagtgat    5520
aagaataggg gaaaatccga caacgtgcct agtgaggagg tggttaaaaa gatgaaaaat    5580
tattggagac agttattgaa cgcaaagctt attacacaga ggaagttcga caatttgact    5640
aaggctgaga ggggaggttt atctgagttg acaaggctg gattcattaa gagacaactt    5700 gttgaaaacca gacaaataac taagcatgtg gctcagatcc ttgattcaag aatgaacacc    5760
aagtacgatg aaaacgacaa gttgatcaga gaggttaaag tgattactct taagagtaag    5820
ttggtttccg atttcagaaa ggacttccaa ttctacaaag tgagggaaat taataactat    5880
catcacgctc acgatgcata cttgaatgct gttgtgggta ctgcattgat caaaaagtac    5940
ccaaagttag aatctgagtt cgtttatgga gattacaagg tttacgacgt gagaaagatg    6000
attgctaagt cagaacagga gattggtaaa gctacagcaa agtactttt ctatagtaac    6060 atcatgaact ttttcaagac tgaaatcaca ttggctaacg agagatcag aaaaaggcct    6120 ttaatagaaa caaacggtga aaccggagag attgttggg ataagggaag agactttgca    6180
actgttagga aggtgttgtc catgccacaa gttaatatcg tgaaaagac tgaagttcag    6240 acaggtggat tcagtaagga gtccatactt cctaaaagaa acagtgataa gttgattgct    6300
aggaaaaagg attgggaccc aaagaaatat ggtggatttg atagtcctac agttgcttac    6360
tccgtgcttg ttgtggcaaa ggttgaaaag ggtaaatcta aaaagttgaa gtcagtgaag    6420
```

```
gagttgttag gaattaccat catggaaaga tcttcatttg agaaaaatcc aattgatttc      6480
ttagaagcta agggttacaa ggaggttaaa aaggacttaa ttatcaaact tcctaagtac      6540
agtttgttcg aattagagaa cggaagaaaa aggatgttag cttccgcagg tgaacttcaa      6600
aagggaaatg agcttgcttt gccatctaag tacgttaact tcttatatct tgcatctcat      6660
tacgaaaaat tgaagggttc acctgaagat aatgagcaaa agcagctttt cgttgaacaa      6720
cataagcact atcttgacga aatcatagag cagatatctg aattctcaaa gagagttatc      6780
cttgctgatg caaatttgga caaagtgtta tcagcttaca acaaacatag agataagcca      6840
attagggaac aagcagagaa tatcatacac ctttttacct tgactaactt aggagctcct      6900
gctgctttta aatacttcga tactacaatc gacagaaaga ggtacacatc taccaaagaa      6960
gttcttgatg caacattgat acaccagagt atcacaggac tttatgagac cagaatagac      7020
cttctcccagt taggaggaga tggatccact agtggtccaa agaaaaagag aaaagtggca     7080
gcagcagctc ctaaaaagaa agaaaaggtt ggtggcagca gcgacccagc attcctttac      7140
aaagttgtct gaggatccct aactaggatg agctaagcta gctatatcat caatttatgt      7200
attacacata atatcgcact cagtctttca tctacggcaa tgtaccagct gatataatca      7260
gttattgaaa tatttctgaa tttaaacttg catcaataaa tttatgtttt tgcttggact      7320
ataatacctg acttgttatt ttatcaataa atatttaaac tatatttctt tcaagatggg      7380
aattaacatc tacaaattgc cttttcttat cgaccatgta ccctaggtac caagcttctc      7440
gagcacgtgc aatgacactc acaaatctag tagtggctga attggctcga tgttaaatgc      7500
aaactaacga agtctcatca aataataact cttcttcttg catttgcttt ctttgccct       7560
ttctctcttc ttccatctca aatctgtctc ttcaatatta ctattgggct tttggttagt      7620
ctataatggg actcaaaata aggctttggc ccacatcata aaagataaat tcacaaatca      7680
aaactaattt tcagagtctt ttgtcccaca tcggtcaatc tactcgtttt gtgtttgttt      7740
atatattaca cgaaacgatg tattcaacga cagggacaaa aagagaaatgt tttagagcta     7800
gaaatagcaa gttaaaataa ggctagtccg ttatcaactt gaaaaagtgg caccgagtcg      7860
gtgcctaggt ttttttttcta gacccagctt tcttgtacaa agttggcatt acgctgcacg      7920
tgagctttcg ttgaacaacg gaaactcgac ttgccttccg cacaatacat catttcttct      7980
tagcttttt tcttcttctt cgttcataca gttttttttt gtttatcagc ttacatttc       8040
ttgaaccgta gctttcgttt tcttcttttt aactttccat tcggagtttt tgtatcttgt      8100
ttcatagttt gtcccaggat tagaatgatt aggcatcgaa ccttcaagaa tttgattgaa      8160
taaaacatct tcattcttaa gatatgaaga taatcttcaa aaggcccctg ggaatctgaa      8220
agaagagaag caggcccatt tatatgggaa agaacaatag tatttcttat ataggcccat      8280
ttaagttgaa aacaatcttc aaaagtccca catcgcttag ataagaaaac gaagctgagt      8340
ttatatacag ctagagtcga agtagtgatt gtcgattacg ctaagaaatt gttttagagc      8400
tagaaatagc aagttaaaat aaggctagtc cgttatcaac ttgaaaaagt ggcaccgagt      8460
cggtgcctag gttcaaacat ttggcaataa agtttcttaa gattgaatcc tgttgccggt      8520
cttgcgatga ttatcatata atttctgttg aattacgtta agcatgtaat aattaacatg      8580
taatgcatga cgttatttat gagatgggtt tttatgatta gagtcccgca attatacatt      8640
taatacgcgc acgtgctcga ggacccagct ttcttgtaca aagtggt                    8687

<210> SEQ ID NO 34
<211> LENGTH: 7
```

```
<212> TYPE: PRT
<213> ORGANISM: Artificial Sequence
<220> FEATURE:
<223> OTHER INFORMATION: synthetic nuclear localization signal

<400> SEQUENCE: 34

Gly Pro Lys Lys Arg Lys Val
1               5

<210> SEQ ID NO 35
<211> LENGTH: 9
<212> TYPE: PRT
<213> ORGANISM: Artificial Sequence
<220> FEATURE:
<223> OTHER INFORMATION: synthetic nuclear localization signal

<400> SEQUENCE: 35

Ala Pro Lys Lys Lys Ala Lys Val Gly
1               5

<210> SEQ ID NO 36
<211> LENGTH: 20
<212> TYPE: PRT
<213> ORGANISM: Artificial Sequence
<220> FEATURE:
<223> OTHER INFORMATION: synthetic nuclear localization signal

<400> SEQUENCE: 36

Gly Pro Lys Lys Lys Arg Lys Val Ala Ala Ala Ala Pro Lys Lys Lys
1               5                   10                  15

Arg Lys Val Gly
            20

<210> SEQ ID NO 37
<211> LENGTH: 7
<212> TYPE: PRT
<213> ORGANISM: Artificial Sequence
<220> FEATURE:
<223> OTHER INFORMATION: synthetic nuclear localization signal

<400> SEQUENCE: 37

Pro Lys Lys Lys Arg Lys Val
1               5
```